United States Patent [19]
Rosenberg

[11] Patent Number: 5,258,362
[45] Date of Patent: Nov. 2, 1993

[54] RENIN INHIBITING COMPOUNDS

[75] Inventor: Saul H. Rosenberg, Libertyville, Ill.

[73] Assignee: Abbott Laboratories, Abbott Park, Ill.

[21] Appl. No.: 880,250

[22] Filed: May 13, 1992

Related U.S. Application Data

[63] Continuation-in-part of Ser. No. 713,475, Jun. 11, 1991, abandoned.

[51] Int. Cl.$^5$ .................... A21K 37/00; C07K 5/06; C07K 5/08
[52] U.S. Cl. .................................. 514/19; 514/18; 530/328; 530/329; 530/330; 530/331; 530/332; 544/369; 544/370; 544/400; 546/280; 548/204; 548/300.7; 548/304.7; 548/311.1; 548/365.7; 549/510; 549/512
[58] Field of Search .............. 530/300, 328, 329, 331, 530/332, 330; 514/18, 19; 544/369, 370, 400; 546/280; 548/204, 342; 549/510, 512

[56] References Cited

U.S. PATENT DOCUMENTS

| | | | |
|---|---|---|---|
| 4,725,583 | 2/1988 | Luly et al. | 514/18 |
| 4,826,815 | 5/1989 | Luly et al. | 514/18 |
| 4,837,204 | 6/1989 | Rosenberg et al. | 514/18 |
| 4,855,286 | 8/1989 | Wagner et al. | 514/18 |
| 4,895,834 | 1/1990 | Hudspeth et al. | 514/19 |
| 5,049,548 | 9/1991 | Greenlee et al. | 514/19 |
| 5,059,589 | 10/1991 | Stein et al. | 514/19 |
| 5,063,208 | 11/1991 | Rosenberg et al. | 514/19 |
| 5,106,835 | 4/1992 | Albright et al. | 514/19 |
| 5,134,123 | 7/1992 | Branca et al. | 514/19 |
| 5,149,692 | 9/1992 | Doherty et al. | 514/19 |

FOREIGN PATENT DOCUMENTS 230266  7/1987  European Pat. Off. .
307837  3/1989  European Pat. Off. .

*Primary Examiner*—Cecilia Tsang
*Attorney, Agent, or Firm*—Steven R. Crowley

[57] ABSTRACT

A renin inhibiting compound of the formula:

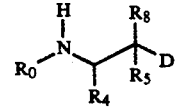

wherein $R_0$ is a mimic of the Phe-His dipeptide sequence of angiotensinogen which preceeds the renin cleavage site;
$R_4$ is loweralkyl, cycloalkylalkyl or arylalkyl;
$R_5$ is hydrogen, loweralkyl, hydroxyalkyl, loweralkenyl or formyl;
$R_6$ is —OH or —NH$_2$; and
D is

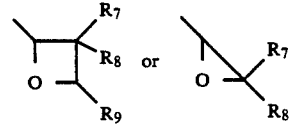

wherein $R_7$ is hydrogen or loweralkyl and $R_8$ is hydrogen, loweralkyl, hydroxyalkyl, alkoxyalkyl, thioalkoxyalkyl, haloalkyl, aminoalkyl, alkylaminoalkyl, dialkylaminoalkyl, cycloalkyl, cycloalkylalkyl, loweralkenyl, alkynyl, aryl, arylalkyl, heterocyclic or heterocyclicalkyl; or $R_7$ and $R_8$ taken together —(CH$_2$)$_n$— wherein n is 3–6; and $R_9$ is loweralkyl; or a pharmaceutically acceptable salt, ester or prodrug thereof.

26 Claims, No Drawings

RENIN INHIBITING COMPOUNDS

This is a continuation-in-part of U.S. Pat. application Ser. No. 713,475, filed Jun. 11, 1991 now abandoned.

TECHNICAL FIELD

The present invention relates to novel compounds and compositions which inhibit renin, processes for making the compounds and a method of treating hypertension or congestive heart failure, glaucoma, vascular disease, renal failure or psoriasis with a compound of the invention. In addition, the present invention relates to a method for inhibiting a retroviral protease or treating a retroviral infection with a compound of the invention.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. Renin acts on a circulating protein, angiotensinogen, to cleave out a fragment called angiotensin I (AI). AI itself has only slight pharamacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. Sodium retention causes blood volume to increase, which leads to hypertension. AII is cleaved by an aminopeptidase to form angiotensin III (AIII), which, compared to AII, is a less potent vasoconstrictor but a more potent inducer of aldosterone release.

The renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavorial and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

Inhibitors of renin have been sought as agents for control of hypertension and as diagnostic agents for identification of cases of hypertension due to renin excess.

In efforts to identify compounds which inhibit renin, compounds have been prepared which mimic angiotensinogen, the natural substrate for renin. In particular, compounds have been prepared which incorporate mimics of the dipeptide sequence of angiotensinogen preceeding the renin cleavage site (i.e., mimics of Phe-His) and which also incorporate non-cleavable mimics of the renin cleavage site of angiotensinogen (i.e., Leu-Val). Compounds comprising mimics of both portions of angiotensinogen bind to renin, but are not cleaved. Thus, renin is inhibited from acting on its natural substrate.

DISCLOSURE OF THE INVENTION

In accordance with the present invention, there are compounds of the formula:

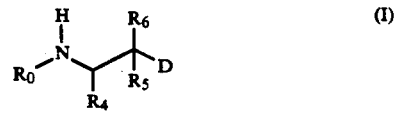
(I)

wherein $R_0$ is a mimic of the Phe-His dipeptide sequence of angiotensinogen which preceeds the renin cleavage site;

$R_4$ is loweralkyl, cycloalkylalkyl or arylalkyl;

$R_5$ is hydrogen, loweralkyl, hydroxyalkyl, loweralkenyl or formyl;

$R_6$ is —OH or —NH$_2$; and

D is

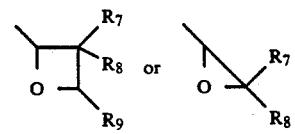

wherein $R_7$ is hydrogen or loweralkyl and $R_8$ is hydrogen, loweralkyl, hydroxyalkyl, alkoxyalkyl, thioalkoxyalkyl, haloalkyl, aminoalkyl, alkylaminoalkyl, dialkylaminoalkyl, cycloalkyl, cycloalkylalkyl, loweralkenyl, alkynyl, aryl, arylalkyl, heterocyclic or heterocyclicalkyl; or $R_7$ and $R_8$ taken together are —(CH$_2$)$_n$— wherein n is 3–6; and $R_9$ is hydrogen or loweralkyl; or a pharmaceutically acceptable salt, ester or prodrug thereof.

Preferred compounds of the invention are compounds of the formula:

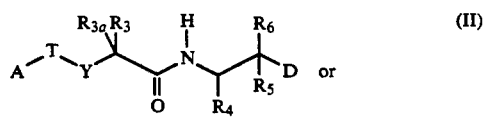
(II)

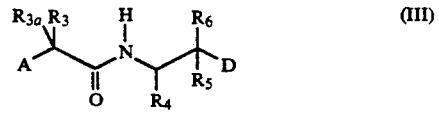
(III)

wherein A is
(1) hydrogen,
(2) loweralkyl,
(3) aryl,
(4) arylalkyl,
(5) heterocyclic,
(6) (heterocyclic)alkyl,
(7) —OR$_{10}$ or —SR$_{10}$ wherein R$_{10}$ is hydrogen, loweralkyl or aminoalkyl,
(8) —NR$_{11}$R$_{12}$ wherein R$_{11}$ and R$_{12}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected- )amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkylamino)alkoxycarbonylalkyl, ((N-protected)alkylamino)alkoxycarbonylalkyl and (dialkylamino)alkoxycarbonylalkyl, (9) (alkoxy)(alkyl)aminoalkyl,
(10) (alkoxy)aminoalkyl,
(11) (alkoxyalkoxy)aminoalkyl,
(12) (alkoxyalkoxy)(alkyl)aminoalkyl or
(13) $R_{13}$—Q—B— wherein
  B is
  (i) —N($R_9$)— wherein $R_{19}$ is hydrogen or loweralkyl,
  (ii) —NHCH$_2$—
  (iii) —S—,
  (iv) —O—,
  (v) —(CH$_2$)$_b$— wherein b is 0–4 or
  (vi) —CH(O$R_{20}$)— wherein $R_{20}$ is hydrogen, loweralkyl or —C(O)$R_{21}$; wherein $R_{21}$ is loweralkyl or haloalkyl,
  Q is
  (i) —C(O)—,
  (ii) —(O)—,
  (iii) —(O)$_2$— or
  (iv) —CH(O$R_4$)— wherein $R_{14}$ is hydrogen, loweralkyl or —C(O)$R_{15}$ wherein $R_{15}$ is loweralkyl or haloalkyl and
  $R_{13}$ is
  (i) loweralkyl,
  (ii) cycloalkyl,
  (iii) cycloalkylalkyl,
  (iv) cycloalkenyl,
  (v) cycloalkenylalkyl,
  (vi) amino,
  (vii) di-(alkoxyalkyl)amino,
  (viii) di-(alkoxyalkoxyalkyl)amino,
  (ix) di-(hydroxyalkyl)amino,
  (x) aminoalkyl,
  (xi) (N-protected)aminoalkyl,
  (xii) (N-protected)(alkyl)aminoalkyl,
  (xiii) aryl,
  (xiv) arylalkyl,
  (xv) heterocyclic,
  (xvi) (heterocyclic)alkyl,
  (xvii) carboxyalkyl,
  (xviii) (amino)carboxyalkyl,
  (xix) ((N-protected)amino)carboxyalkyl,
  (xx) (alkylamino)carboxyalkyl,
  (xxi) ((N-protected)(alkyl)amino)carboxyalkyl,
  (xxii) (dialkylamino)carboxyalkyl,
  (xxiii) alkoxycarbonylalkyl,
  (xxiv) (amino)alkoxycarbonylalkyl,
  (xxv) ((N-protected)amino)alkoxycarbonylalkyl,
  (xxvi) (alkylamino)alkoxycarbonylalkyl,
  (xxvii) (((N-protected)(alkyl)amino)alkoxycarbonylalkyl,
  (xxviii) (dialkylamino)alkoxycarbonylalkyl,
  (xxix) —N=C(N$R_aR_b$)hd  wherein at each occurrence $R_a$ and $R_b$ are independently selected from loweralkyl or
  (xxx) $R_{16}$—G—$R_{17}$— wherein $R_{16}$ is
    (a) loweralkyl,
    (b) loweralkenyl,
    (c) cycloalkyl
    (d) cycloalkenyl,
    (e) cycloalkyalkyl,
    (f) cycloalkenyalkyl,
    (g) hydroxyalkyl,
    (h) dihydroxyalkyl,
    (i) alkoxyalkyl,
    (j) alkoxyalkoxyalkyl,
    (k) polyalkoxyalkyl,
    (l) aryl,
    (m) arylalkyl,
    (n) heterocyclic,
    (o) (heterocyclic)alkyl,
    (p) carboxyalkyl,
    (q) (amino)carboxyalkyl,
    (r) ((N-protected)amino)carboxyalkyl,
    (s) (alkylamino)carboxyalkyl,
    (t) ((N-protected)alkylamino)carboxyalkyl,
    (u) (dialkylamino)carboxyalkyl,
    (v) alkoxycarbonylalkyl,
    (w) (amino)alkoxycarbonylalkyl,
    (x) ((N-protected)amino)alkoxycarbonylalkyl,
    (y) (alkylamino)alkoxycarbonylalkyl,
    (z) ((N-protected)alkylamino)alkoxycarbonylalkyl,
    (aa) (dialkylamino)alkoxycarbonylalkyl,
    (bb) alkylsulfonyl,
    (cc) alkylsulfonylalkyl,
    (dd) arylsulfonyl,
    (ee) arylsulfonylalkyl,
    (ff) (heterocyclic)sulfonyl,
    (gg) (heterocyclic)sulfonylalkyl,
    (hh) aminoalkyl,
    (ii) (N-protected)aminoalkyl,
    (jj) alkylaminoalkyl,
    (kk) (N-protected)(alkyl)aminoalkyl or
    (ll) dialkylaminoalkyl,
  $R_{17}$ is absent or alkylene and G is —S—, —S(O)—, —S(O)$_2$—, —O— or —N($R_{22}$)— wherein $R_{22}$ is hydrogen or loweralkyl;
T is —CH($R_1$)— or —C(=CH$R_{1a}$)— wherein $R_1$ is
  (1) loweralkyl,
  (2) loweralkenyl,
  (3) cycloalkylalkyl,
  (4) cycloalkenylalkyl,
  (5) alkoxyalkyl,
  (6) thioalkoxyalkyl,
  (7) arylalkyl,
  (8) (heterocyclic)alkyl,
  (9) aryloxyalkyl,
  (10) thioaryloxyalkyl,
  (11) arylaminoalkyl,
  (12) aryloxy,
  (13) thioaryloxy,
  (14) arylalkoxyalkyl,
  (15) arylthioalkoxyalkyl or
  (16) arylamino; and
  $R_{1a}$ is aryl or arylalkyl;
Y is
  (1) —CH$_2$—,
  (2) —CH(OH)—,
  (3) —C(O)—,
  (5) —O—,
  (6) —S—,
  (7) —(O)—,
  (8) —(O)$_2$—,
  (9) —N(O)—,
  (10) —P(O)O— or
  (11) —W—U— wherein W is —C(O)— or —CH(OH)— and U is —CH$_2$— or —N($R_2$)— wherein $R_2$ is hydrogen or loweralkyl, with the proviso that W is —C(O)— when U is —N($R_2$)—;
$R_3$ is (1) loweralkyl,
(2) loweralkenyl,
(3) alkynyl,
(4) haloalkyl,
(5) cycloalkyalky,
(6) cycloalkenylalkyl,
(7) alkoxyalkyl,
(8) thioalkoxyalkyl,
(9) ((alkoxy)alkoxy)alkyl,
(10) hydroxyalkyl,
(11) —(CH$_2$)$_d$NHR$_{18}$ wherein d is 1 to 3 and R$_{18}$ is hydrogen, loweralkyl or an N-protecting group,
(12) arylalkyl or
(13) (heterocyclic)alkyl;

R$_{3a}$ is hydrogen or fluoro;
R$_4$ is loweralkyl, cycloalkylalkyl or arylalkyl;
R$_5$ is hydrogen, loweralkyl, hydroxyalkyl, loweralkenyl or formyl;
R$_6$ is —OH or —NH$_2$; and
D is

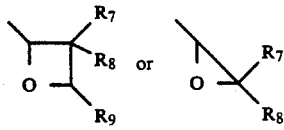

wherein R$_7$ is hydrogen or loweralkyl and R$_8$ is hydrogen, loweralkyl, hydroxyalkyl, alkoxyalkyl, thioalkoxyalkyl, haloalkyl, aminoalkyl, alkylaminoalkyl, dialkylaminoalkyl, cycloalkyl, cycloalkylalkyl, loweralkenyl, alkynyl, aryl, arylalkyl, heterocyclic or heterocyclicalkyl; or R$_7$ and R$_8$ L taken together are —(CH$_2$)$_n$— wherein n is 3–6; and R$_9$ is hydrogen or loweralkyl; or a pharmaceutically acceptable salt, ester or prodrug thereof.

More preferred compounds of the invention are compounds of the formula (II) wherein
A is (heterocyclic)alkyl or R$_{13}$—Q—CH$_2$— wherein Q is —C(O)— or —(O)$_2$— and R$_{13}$ is heterocyclic or R$_{16}$—G— wherein G is —N(R$_{22}$)— wherein R$_{22}$ is hydrogen or loweralkyl and R$_{16}$ is (heterocyclic)alkyl;
T is —CH(R$_1$)— wherein R$_1$ is arylalkyl;
Y is —W—U— wherein W is —C(O)— and U is —NH—;
R$_{3a}$ is hydrogen;
R$_3$ is (heterocyclic)alkyl;
R$_4$ is cycloalkylalkyl;
R$_5$ is hydrogen;
R$_6$ is —OH—; and D is

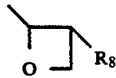

wherein R$_8$ is loweralkyl.

The compounds of formula I contain two or more asymmetric carbon atoms and thus can exist as pure diastereomers, mixtures of diastereomers, diastereomeric racemates or mixtures of diastereomeric racemates. The present invention includes within its scope all of the isomeric forms. The terms "R" and "S" configuration used herein are as defined by IUPAC 1974 Recommendations for Section E, Fundamental Stereochemistry, Pure Appl. Chem (1976) 45, 13–30.

In addition, in the compounds of the invention, combinations of substitutents and/or variables (i.e., R$_0$, R$_1$, R$_2$, etc.) are permissible only if such combinations result in stable compounds.

The term "mimic of the Phe-His dipeptide sequence of angiotensinogen which preceeds the renin cleavage site" as used herein refers to the substituent R$_0$ having the formula

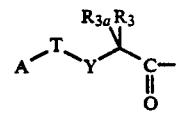

wherein A, T, Y, R$_{3a}$ and R$_3$ are defined as above.

The term "mimic of the Phe-His dipeptide sequence of angiotensinogen which preceeds the renin cleavage site" as used herein also refers to the substituents corresponding to R$_0$ which are disclosed in the following references: German Patent Application No. DE3841319, published Jun. 29, 1989, discloses mimics of the Phe-His dipeptide sequence of angiotensinogen which preceeds the renin cleavage site having the formula A—NHCH(CH$_2$Si(R$_1$)$_3$)C(O)—B— wherein A, R$_1$ and B are as defined therein;

European Patent Application No. EP275480, published Jul. 27, 1988, discloses mimics of the Phe-His dipeptide sequence of angiotensinogen which preceeds the renin cleavage site having the formula ACYL—X—Y— wherein ACYL, X and Y are as defined therein;

European Patent Application No. EP310918, published Apr. 12, 1989, discloses mimics of the Phe-His dipeptide sequence of angiotensinogen which preceeds the renin cleavage site having the formula A—N(R$_1$)—CH(CH$_2$R$_2$)—C(O)— wherein A, R$_1$ and R$_2$ are as defined therein;

European Patent Application No. EP315815, published May 17, 1989, discloses mimics of the Phe-His dipeptide sequence of angiotensinogen which preceeds the renin cleavage site having the formula ACYL—X—Y(B)— wherein ACYL, X, Y and B are as defined therein;

European Patent Application No. EP321192, published Jun. 21, 1989, discloses mimics of the Phe-His dipeptide sequence of angiotensinogen which preceeds the renin as defined therein;

European Patent Application No. EP328978, published Aug. 23, 1989, discloses mimics of the Phe-His dipeptide sequence of angiotensinogen which preceeds the renin cleavage site having the formula R$^1$—Z—(CH$_2$)$_m$—C(O)— wherein R$_1$, Z and m are as defined therein;

European Patent Application No. EP337295, published Oct. 18, 1989, discloses mimics of the Phe-His dipeptide sequence of angiotensinogen which preceeds the renin cleavage site having the formula X—Y—CH(R$_5$)—C(O)NH—CH(R$_4$)—C(O)— wherein X, Y, R$_5$ and R$_4$ are as defined therein;

European Patent Application No. EP337334, published Oct. 18, 1989, discloses mimics of the Phe-His dipeptide sequence of angiotensinogen which preceeds the renin cleavage site having the formula R$^1$—C$_p$H$_{2p}$—(NH)$_y$—C(O)—NH—CH(R$_2$)—C(O)—Z—C$_m$H$_{2m}$—C(O)— wherein R$_1$, p, y, R$_2$, Z and m are as defined therein;

European Patent Application No. EP343654, published Nov. 29, 1989, discloses mimics of the Phe-His dipeptide sequence of angiotensinogen which preceeds the renin cleavage site having the formula A—X—Y— wherein A, X and Y are as defined therein;

European Patent Application No. EP353211, published Jan. 31, 1990, discloses mimics of the Phe-His dipeptide sequence of angiotensinogen which preceeds the renin cleavage site having the formula A—N(R$^1$)—CH(R$^2$)—C(O)— wherein A, R$^1$ and R$^2$ are as defined therein;

European Patent Application No. EP369743, published May, 23 1990, discloses mimics of the Phe-His dipeptide sequence of angiotensinogen which preceeds the renin cleavage site having the formula

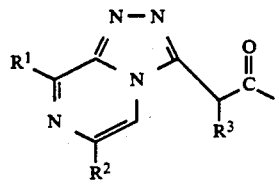

wherein R$^1$, R$^2$ and R$^3$ are as defined therein;

European Patent Application No. EP37771393, published Jul. 11, 1990, discloses mimics of the Phe-His dipeptide sequence of angiotensinogen which preceeds the renin cleavage site having the formula R$^1$—S(O)$_m$—(CH$_2$)$_n$—CH(R$^2$)—C(O)—N(R$^3$)—CH(R$^4$)—C(O)— wherein R$^1$, m, n, R$^2$, R$^3$ and R$^4$ are as defined therein;

European Patent Application No. EP385593, published Sep. 5, 1990, discloses mimics of the Phe-His dipeptide sequence of angiotensinogen which preceeds the renin cleavage site having the formula R$_1$NH—CH(CH$_2$—(p—R$_2$—C$_6$H$_4$))—C(O)N-H—CH(R$_3$)—C(O)— wherein R$_1$, R$_2$ and R$_3$ are as defined therein;

U.S. Pat. No. 4,719,288, issued Jan. 12, 1988, which is hereby incorporated by reference, discloses mimics of the Phe-His dipeptide sequence of angiotensinogen which preceeds the renin cleavage site having the formula R$_1$—X$_1$—X$_2$— wherein R$_1$, X$_1$ and X$_2$ are as defined therein; U.S. Pat. No. 4,743,585, issued May 10, 1988, which is hereby incorporated by reference, discloses mimics of the Phe-His dipeptide sequence of angiotensinogen which preceeds the renin cleavage site having the formula A—B—D—NHCH(CH$_2$R$^2$)-C(O)NH—CH(CH$_2$R$^1$)C(O)— wherein A, B, D, R$_2$ and R$^1$ are as defined therein;

U.S. Pat. No. 4,839,357, issued Jun. 13, 1989, which is hereby incorporated by reference, discloses mimics of the Phe-His dipeptide sequence of angiotensinogen which preceeds the renin cleavage site having the formula A—B— wherein A and B are as defined therein;

U.S. Pat. No. 4,855,286, issued Aug. 8, 1989, which is hereby incorporated by reference, discloses mimics of the Phe-His dipeptide sequence of angiotensinogen which preceeds the renin cleavage site having the formula R$^1$—A—B— wherein R$^1$, A and B are as defined therein;

U.S. Pat. No. 4,863,904, issued Sep. 5, 1989, which is hereby incorporated by reference, discloses mimics of the Phe-His dipeptide sequence of angiotensinogen which preceeds the renin cleavage site having the formula Ar$_1$—(CH$_2$)$_m$—X—(CH$_2$)$_n$—C(R$_1$)(Z—Y—Ar$_2$)—C(O)—His— wherein Ar$_1$, m, X, n, R$_1$, Z, Y and Ar$_2$ are as defined therein;

U.S Pat. No. 4,889,869, issued Dec. 26, 1989, which is hereby incorporated by reference, discloses mimics of the Phe-His dipeptide sequence of angiotensinogen which preceeds the renin cleavage site having the formula R$_1$—A— wherein R$_1$ and A are as defined therein;

U.S Pat. No. 4,894,437, issued Jan. 16, 1990, which is hereby incorporated by reference, discloses mimics of the Phe-His dipeptide sequence of angiotensinogen which preceeds the renin cleavage site having the formula X—A$_6$—B$_7$—C$_8$—D$_9$— wherein X, A$_6$, B$_7$, C$_8$ and D$_9$ are as defined therein;

U.S. Pat. No. 4,895,834, issued Jan. 23, 1990, which is hereby incorporated by reference, discloses mimics of the Phe-His dipeptide sequence of angiotensinogen which preceeds the renin cleavage site having the formula ACYL—X— wherein ACYL and X are as defined therein;

U.S. Pat. No. 4,900,745, issued Feb. 13, 1990, which is hereby incorporated by reference, discloses mimics of the Phe-His dipeptide sequence of angiotensinogen which preceeds the renin cleavage site having the formula (R$_9$)(R$_1$)NCH(R$_{12}$)(CH$_2$)$_p$CH(R$_{14}$)N(R$_1$)CH(R$_{11}$)(CH$_2$)$_n$CH(R$_{15}$)—N(R$_2$(C(O)—X—CH(R$_3$)-C(O)N(R$_9$)(CH$_2$)$_m$CH(R$_5$)C(O)— wherein R$_3$, R$_{10}$, R$_{12}$, p, R$_{14}$, R$_1$, R$_{11}$, n, R$_{15}$, R$_2$, X, R$_3$, R$_9$, m and R$_5$ are as defined therein;

U.S Pat. No. 4,931,429, issued Jun. 5, 1990, which is hereby incorporated by reference, discloses mimics of the Phe-His dipeptide sequence of angiotensinogen which preceeds the renin cleavage site having the formula R$_9$C(O)N(R$_8$)CH(R$_3$)C(O)N(R$_4$)CH(R$_6$)CH(R$_2$)-C(O)— wherein R$_9$, R$_8$, R$_3$, R$_4$, R$_6$, and R$_2$ are as defined therein;

U.S. Pat. No. 4,935,405, issued Jun. 19, 1990, which is hereby incorporated by reference, discloses mimics of the Phe-His dipeptide sequence of angiotensinogen which preceeds the renin cleavage site having the formula ZCH(CH$_2$M)C(O)N(Q)CH(R$_2$)C(O)— or

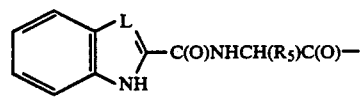

wherein Z, M, Q, R$_2$, L and R$_5$ are as defined therein;

PCT Patent Application No. WO88/07053, published Sep. 22, 1988, discloses mimics of the Phe-His dipeptide sequence of angiotensinogen which preceeds the renin cleavage site having the formula X—A$_6$—B$_7$—C$_8$—D$_9$— wherein X, A$_6$, B$_7$, C$_8$ and D$_9$ are as defined therein;

PCT Patent Application No. WO87/05909, published Sep. 8, 1987, discloses mimics of the Phe-His dipeptide sequence of angiotensinogen which preceeds the renin cleavage site having the formula X—A$_6$—B$_7$—C$_8$—D$_9$— wherein X, A$_6$, B$_7$, C$_8$ and D$_9$ are as defined therein;

PCT Patent Application No. WO89/01488, published Feb. 23, 1989, discloses mimics of the Phe-His dipeptide sequence of angiotensinogen which preceeds the renin cleavage site having the formula X—A$_6$—B$_7$—C$_8$—D$_9$— wherein X, A$_6$, B$_7$, C$_8$ and D$_9$ are as defined therein;

PCT Patent Application No. WO89/04833, published Jun. 1, 1989, discloses mimics of the Phe-His dipeptide sequence of angiotensinogen which preceeds the renin cleavage site having the formula A—B—D—V—CH- $(CO_2H)(CH_2)_mC(O)$— wherein A, B, D, V and m are as defined therein;

PCT Patent Application No. WO90/03389, published May 5, 1990, discloses mimics of the Phe-His dipeptide sequence of angiotensinogen which preceeds the renin cleavage site having the formula $A_6$ wherein $A_6$ is as defined therein;

The term "loweralkyl" as used herein refers to straight or branched chain alkyl radicals containing from 1 to 7 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkylene" as used herein refers to a straight or branched chain carbon diradical containing from 1 to 7 carbon atoms including, but not limited to, $-CH_2-$, $-CH_2CH_2-$, $-CH(CH_3)CH_2-$, $-CH_2CH_2CH_2$' and the like.

The term "loweralkenyl" as used herein refers to a loweralkyl radical having 2-7 carbon atoms which contains at least one carbon-carbon double bond including, but not limited to, propenyl, butenyl and the like. Alkenyl groups can be unsubstituted or substituted with one or two substituents independently selected from loweralkyl, haloalkyl, cycloalkyl, aryl, heterocyclic, alkoxy, thioalkoxy, amino, alkylamino, dialkylamino, hydroxy, halo, mercapto, nitro, carboxaldehyde, carboxy, alkoxycarbonyl and carboxamide.

The term "alkynyl" as used herein refers to a loweralkyl radical having 2-7 carbon atoms and which contains a carbon-carbon triple bond.

The term "cycloalkyl" as used herein refers to an aliphatic ring having 3 to 7 carbon atoms including, but not limited to, cyclopropyl, cyclopentyl, cyclohexyl and the like. Cycloalkyl groups can be unsubstituted or substituted with one or two substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide.

The term "cycloalkylalkyl" as used herein refers to a loweralkyl radical to which is appended a cycloalkyl group including, but not limited to, cyclohexylmethyl, cyclopentylmethyl and the like.

The term "cycloalkenyl" as used herein refers to a cycloalkyl radical which contains a carbon-carbon double bond including, but not limited to, cyclohexenyl, cyclopentenyl and the like.

The term "cycloalkenylalkyl" as used herein refers to a loweralkyl radical to which is appended a cycloalkenyl group.

The term "aminoalkyl" as used herein refers to a loweralkyl radical to which is appended an $-NH_2$ group.

The term "hydroxyalkyl" as used herein refers to a loweralkyl radical to which is appended an $-OH$ group.

The term "dihydroxyalkyl" as used herein refers to a loweralkyl radical disubstituted with $-OH$ groups.

The term "cyanoalkyl" as used herein refers to a loweralkyl radical to which is appended a $-CN$ group.

The term "halo" or "halogen" as used herein refers to $-Cl$, $-Br$, $-I$ or $-F$.

The term "haloalkyl" as used herein refers to a loweralkyl radical in which one or more of the hydrogen atoms are replaced by halogen including, but not limited to, chloromethyl, trifluoromethyl, 1-chloro-2-fluoroethyl and the like.

The terms "alkoxy" and "thioalkoxy" as used herein refer to $R_{30}-$ and $R_{30}S-$, respectively, wherein $R_{30}$ is a loweralkyl group or benzyl.

The term "alkoxyalkyl" as used herein refers to a loweralkyl radical to which is appended an alkoxy group.

The term "thioalkoxyalkyl" as used herein refers to a loweralkyl radical to which is appended a thioalkoxy group.

The term "alkoxyalkoxy" as used herein refers to $R_{31}OR_{32}O-$ wherein $R_{31}$ is a loweralkyl group and $R_{32}$ is an alkylene group including, but not limited to, methoxymethoxy, ethoxymethoxy and the like.

The term "alkoxyalkoxyalkyl" as used herein refers to a loweralkyl radical to which is appended an alkoxyalkoxy group including, but not limited to, methoxyethoxymethyl and the like.

The term "polyalkoxy" as used herein refers to $-OR_{33}$ wherein $R_{33}$ is a straight or branched chain containing 2-5, $C_{n'}-O-C_{n''}$ linkages wherein n' and n'' are independently selected from 1 to 3 including, but not limited to, methoxyethoxymethoxy and the like.

The term "polyalkoxyalkyl" as used herein refers to a loweralkyl radical to which is appended a polyalkoxy group.

The term "carboxyalkyl" as used herein refers to a loweralkyl radical to which is appended a carboxylic acid group ($-COOH$).

The term "alkoxycarbonyl" as used herein refers to $R_{34}C(O)-$ wherein $R_{34}$ is an alkoxy group.

The term "alkoxycarbonylalkyl" as used herein refers to a loweralkyl radical to which is appended an alkoxycarbonyl group.

The term "aryl" as used herein refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, carboalkoxy and carboxamide.

The term "arylalkyl" as used herein refers to a loweralkyl radical to which is appended an aryl group including, but not limited to, benzyl, 4-hydroxybenzyl, 1-naphthylmethyl and the like.

The term "alkoxyaminoalkyl" as used herein refers to a loweralkyl radical to which is appended $-NHR_{35}$ wherein $R_{35}$ is an alkoxy group.

The term "(alkoxy)(alkyl)aminoalkyl" as used herein refers to a loweralkyl radical to which is appended $(R_{36})(R_{37})N-$ wherein $R_{36}$ is an alkoxy group and $R_{37}$ is a loweralkyl group.

The term "alkylamino" as used herein refers to $-NHR_{38}$ wherein $R_{38}$ is a loweralkyl group.

The term "dialkylamino" as used herein refers to $-NR_{39}R_{40}$ wherein $R_{39}$ and $R_{40}$ are independently selected from loweralkyl groups.

The term "(alkoxyalkoxy)amino" as used herein refers to $-NHR_{41}$ wherein $R_{41}$ is an alkoxyalkoxy group.

The term "(alkoxyalkoxy)aminoalkyl" as used herein refers to a loweralkyl radical to which is appended an (alkoxyalkoxy)amino group.

The term "(alkoxyalkoxy)(alkyl)amino" as used herein refers to —NR$_{42}$R$_{43}$ wherein R$_{42}$ is an alkoxyalkoxy group and R$_{43}$ is a loweralkyl group.

The term "(alkoxyalkoxy)(alkyl)aminoalkyl" as used herein refers to a loweralkyl radical to which is appended an (alkoxyalkoxy)(alkyl)amino group.

The term "di-(alkoxyalkyl)amino" as used herein refers to —NR$_{44}$R$_{45}$ wherein R$_{44}$ and R$_{45}$ are independently selected from alkoxyalkyl.

The term "di-(alkoxyalkoxyalkyl)amino" as used herein refers to —NR$_{46}$R$_{47}$ wherein R$_{46}$ and R$_{47}$ are independently selected from alkoxyalkoxyalkyl.

The term "di-(hydroxyalkyl)amino" as used herein refers to —NR$_{48}$R$_{49}$ wherein R$_{48}$ and R$_{49}$ are independently selected from hydroxyalkyl.

The term "arylalkoxy" as used herein refers R$_{50}$O— wherein R$_{50}$ is a arylalkyl group as defined above.

The term "arylalkoxyalkyl" as used herein refers to a loweralkyl radical to which is appended an arylalkoxy group.

The term "aryloxy" as used herein refers to R$_{51}$O— wherein R$_{51}$ is an aryl group.

The term "aryloxyalkyl" as used herein refers to a loweralkyl radical to which is appended an aryloxy group.

The term "arylthioalkoxy" as used herein refers to a R$_{52}$S— wherein R$_{52}$ is an arylalkyl group.

The term "arylthioalkoxyalkyl" as used herein refers to a loweralkyl radical to which is appended an arylthioalkoxy group.

The term "thioaryloxy" as used herein refers to R$_{53}$S— wherein R$_{53}$ is an aryl group.

The term "thioaryloxyalkyl" as used herein refers to a loweralkyl radical to which is appended a thioaryloxy group.

The term "arylamino" as used herein refers to —NHR$_{54}$ wherein R$_{54}$ is an aryl group.

The term "arylaminoalkyl" as used herein refers to a loweralkyl radical to which is appended an arylamino group.

The term "(N-protected)aminoalkyl" as used herein refers to a loweralkyl radical to which is appended an —NHR$_{55}$ group wherein R$_{55}$ is an N-protecting group.

The term "alkylaminoalkyl" as used herein refers to a loweralkyl radical to which is appended an NHR$_{56}$ group wherein R$_{56}$ is a loweralkyl group.

The term "(N-protected)(alkyl)aminoalkyl" as used herein refers to a loweralkyl radical to which is appended an —NR$_{55}$R$_{56}$ group wherein R$_{55}$ and R$_{56}$ are as defined above.

The term "dialkylaminoalkyl" as used herein refers to a loweralkyl radical to which is appended an —NR$_{57}$R$_{58}$ group wherein R$_{57}$ and R$_{58}$ are independently selected from loweralkyl.

The term "(amino)carboxyalkyl" as used herein refers to a loweralkyl radical to which is appended a carboxylic acid group (—COOH) and an amino group (—NH$_2$).

The term "((N-protected)amino)carboxyalkyl" as used herein refers to a loweralkyl radical to which is appended a carboxylic acid group (—COOH) and to which is also appended an —NHR$_{59}$ group wherein R$_{59}$ is an N-protecting group.

The term "(alkylamino)carboxyalkyl" as used herein refers to a loweralkyl radical to which is appended a carboxylic acid group (—COOH) and to which is also appended an alkylamino group.

The term "((N-protected)alkylamino)carboxyalkyl" as used herein refers to a loweralkyl radical to which is appended a carboxylic acid group (—COOH) and to which is also appended an —NR$_{59}$R$_{60}$ group wherein R$_{59}$ is as defined above and R$_{60}$ is a loweralkyl group.

The term "(dialkylamino)carboxyalkyl" as used herein refers to a loweralkyl radical to which is appended a carboxylic acid group (—COOH) and to which is also appended an —NR$_{61}$R$_{62}$ group wherein R$_{61}$ and R$_{62}$ are independently selected from loweralkyl.

The term "(amino)alkoxycarbonylalkyl" as used herein refers to a loweralkyl radical to which is appended an alkoxycarbonyl group and to which is also appended an amino group (—NH$_2$).

The term "((N-protected)amino)alkoxycarbonylalkyl" as used herein refers to a loweralkyl radical to which is appended an alkoxycarbonyl group and to which is also appended an —NHR$_{63}$ group wherein R$_{63}$ is an N-protecting group.

The term "(alkylamino)alkoxycarbonylalkyl" as used herein refers to a loweralkyl radical to which is appended an alkoxycarbonyl group and to which is also appended an alkylamino group.

The term "((N-protected)alkylamino)alkoxycarbonylalkyl" as used herein refers to a loweralkyl radical to which is appended an alkoxycarbonyl group and to which is also appended an —NR$_{64}$R$_{65}$ group wherein R$_{64}$ is an N-protecting group and R$_{65}$ is a loweralkyl group.

The term "(dialkylamino)alkoxycarbonylalkyl" as used herein refers to a loweralkyl radical to which is appended an alkoxycarbonyl group and —NR$_{66}$R$_{67}$ wherein R$_{66}$ and R$_{67}$ are independently selected from loweralkyl.

The term "alkylsulfonyl" as used herein refers to R$_{68}$SO$_2$— wherein R$_{68}$ is a loweralkyl group.

The term "alkylsulfonylalkyl" as used herein refers to a loweralkyl radical to which is appended an alkylsulfonyl group.

The term "arylsulfonyl" as used herein refers to R$_{69}$S(O)$_2$— wherein R$_{69}$ is an aryl group.

The term "arylsulfonylalkyl" as used herein refers to a loweralkyl radical to which is appended an arylsulfonyl group.

The term "(heterocyclic)sulfonyl" as used herein refers to a heterocyclic group.

The term "(heterocyclic)sulfonylalkyl" as used herein refers to a loweralkyl radical to which is appended a (heterocyclic)sulfonyl group.

At each occurrence, the term "heterocyclic ring" or "heterocyclic" as used herein independently refers to a 3- or 4-membered ring containing a heteroatom selected from oxygen, nitrogen and sulfur; or a 5- or 6-membered ring containing one, two or three nitrogen atoms; one nitrogen and one sulfur atom; or one nitrogen and one oxygen atom. The 5-membered ring has 0–2 double bonds and the 6-membered ring has 0–3 double bonds. The nitrogen or sulfur heteroatoms can be optionally oxidized. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Preferred heterocyclics are: azetidinyl, N-methylazetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, N-methylpiperazinyl, pyrimidinyl, pyridazinyl, oxazolyl, oxazolidinyl, isoxazolyl, isoxazolidinyl, morpholinyl, thiomorpholinyl, thiazolyl, 2-aminothiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl and benzothienyl.

Heterocyclics can be unsubstituted or monosubstituted or disubstituted with substituents independently selected from hydroxy, halo, oxo (=O), alkylimino (R*N= wherein R* is a loweralkyl group), amino, alkylamino, dialkylamino, alkoxy, alkoxyalkoxy, polyalkoxy, haloalkyl, cycloalkyl, aryl, arylalkyl, —COOH, —SO$_3$H and loweralkyl. In addition, nitrogen containing heterocycles can be N-protected.

The term "(heterocyclic)alkyl" as used herein refers to a heterocyclic group appended to a loweralkyl radical, including, but not limited to, imidazolylmethyl, thiazolylmethyl and the like.

The term "N-protecting group" or "N-protected" as used herein refers to those groups intended to protect the N-terminus of an amino acid or peptide or to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, t-butyloxycarbonyl (Boc), benzyloxycarbonyl (Cbz) and the like. N-protecting groups also include an L- or D- aminoacyl residue, which is derived from an L- or D- amino acid.

The term "Ala" as used herein refers to alanine. In general, the amino acid abbreviations follow the IUPAC-IUB Joint Commission on Biochemical Nomenclature for amino acids and peptides (Eur. J. Biochem. 1984, 158, 9-31).

The compounds of the invention can be prepared as shown in Schemes 1-2. Scheme 1 outlines a general process for the preparation of oxetanyl intermediate 7. Aldehyde 1 (R$_4$ is as defined herein) is reacted with halo-ester 2 (R$_{100}$ is bromo, chloro or iodo, R$_{101}$; is loweralkyl and R$_7$ and R$_8$ are as defined herein) in the presence of zinc in an inert solvent (for example, tetrahydrofuran (THF), diethyl ether or dioxane and the like) under sonicating conditions to provide hydroxy ester 3. (Other protected forms of the amino alcohol can be used in place of 1, for example, those derived from reaction of the amino alcohol with ketones such as t-butylmethyl ketone, acetophenone, cyclopentanone, cyclohexanone and the like or those derived from reaction of the amino alcohol with aldehydes such as acetaldehyde or benzaldehyde and the like. In addition, the amino group in 1can be protected by groups other than t-butyloxycarbonyl (Boc), for example, benzyloxycarbonyl (Cbz) and the like). Reduction of 3 (for example, with NaBH$_4$, LiBH$_4$, Ca(BH$_4$)$_2$ or Dibal and the like) in a solvent such as ethanol, THF, diethyl ether, dioxane or isopropanol and the like provides diol 4. The primary alcohol of 4 is converted to a sulfonate leaving group (i.e., compound 5 wherein R$_{102}$ is loweralkyl, haloalkyl or aryl) by reaction with R$_{102}$SO$_2$Cl in the presence of base (for example, in pyridine or CH$_2$Cl$_2$/Et$_3$N and the like). Reaction of 5 with a nonnucleophilic base (for example, NaN(SiMe$_3$)$_2$, lithium diisopropyl amide, KH or NaH and the like) in an inert solvent (for example, THF, diethyl ether or dioxane and the like) gives 6. Deprotection of 6 under acidic conditions (for example CF$_3$COOH/CH$_2$Cl$_2$ or HCl/ethanol and the like) provides 7.

Scheme 1 also outlines an alternative preparation of 4 wherein 1 is reacted with (R$_7$)(R$_8$)C=C(OSiMe$_3$)(S-t-butyl) in the presence of a Lewis acid (for example, BF$_3$.Et$_2$O and the like) to give thioester 3a. Reduction of 3a (for example, with NaBH$_4$, LiBH$_4$, Ca(BH$_4$)2 or Dibal and the like) in a solvent such as ethanol, THF, diethyl ether, dioxane or isopropanol and the like provides diol 4.

Scheme 2 outlines a general process for the preparation of compound I wherein R$_0$ is A—T—Y—CH(-R$_{3a}$)(R$_3$)C(O)— and comprises an oxetane. For the compounds wherein Y is —C(O)—N(R$_2$)—, carboxylic acid 8, or an activated derivative thereof, (P$_1$ is hydrogen or an N-protecting group, R$_2$, R$_{3a}$ and R$_3$ are as defined herein) is coupled with oxetanyl amine 7 (R$_4$, R$_7$ and R$_8$ are as defined herein) using standard peptide coupling methods Removal of the protecting group P$_1$ from the resulting product provides 9. Amine 9 is then coupled with carboxylic acid 10, or an activated derivative thereof, (A and T are as defined herein) using standard peptide coupling methods to provide I.

Alternatively, carboxylic acid 10, or an activated derivative thereof, is coupled with amine 12 (P$_2$ is loweralkyl or benzyl). Removal of the protecting group P$_2$ from the resulting product by hydrolysis or hydrogenation provides 11. Carboxylic acid 11, or an activated derivative thereof, is then coupled with 7 to give I.

For the compounds wherein Y is not —C(O)—N(R$_2$)—, carboxylic acid 13, or an activated derivative thereof, is coupled with 7 to provide I.

Activated derivatives of carboxylic acids as mentioned herein refer to acid halides such as acid chlorides, and activated esters including, but not limited to, formic and acetic acid derived anhydrides, anhydrides derived from alkoxycarbonyl halides such as isobutyloxycarbonylchloride and the like, N-hydroxysuccinimide derived esters, N-hydroxyphthalimide derived esters, N-hydroxybenzotriazole derived esters, N-hydroxy-5-norbornene-2,3-dicarboxamide derived esters, 2,4,5-trichlorophenol derived esters and the like.

Scheme 3 outlines a general process for the preparation of oxetanyl intermediates 16 wherein R$_9$ is loweralkyl. Reduction of ester 3 with diisobutylaluminum hydride (Dibal) and the like provides aldehyde 14. Reaction of 14 with an alkylmetal R$_9$M wherein M is Li or MgX (X is halogen) and the like provides diol 15. Reaction of 15 according to the process outlined for reaction of 4 in Scheme 1 provides 16.

Scheme 4 outlines a general process for the preparation of oxetanyl intermediates 17 wherein R$_5$ is other than hydrogen. Oxidation of alcohol 17 provides ketone 18. Reaction of 18 with an alkylmetal, for example, an alkyllithium or a Grignard reagent provides 19 wherein R$_5$ is loweralkyl. Reaction of 18 with an alkenylmetal, for example, alkenyllithium and the like, such as vinyllithium, provides 20. Oxidation of 20, for example, ozonolysis and the like, provides aldehyde 21. Hydroboration of 20 provides 22 wherein e is 2. Ozonolysis of 20, followed by reduction, for example, with sodium borohydride and the like, provides 22 wherein e is 1. Similarly, reaction of 18 with other alkenylmetals will provide compound 22 wherein the alkyl chain has varying lengths and varying positions of the hydroxyl group along the alkyl chain.

Scheme 5 outlines a general process for the preparation of intermediates 27 and 29 which are useful for preparing the compounds of the invention comprising an oxirane moiety. Vinyl bromide 25 is treated with magnesium to provide the Grignard reagent. The Grignard reagent is then reacted with aldehyde 26. Alcohol 27 is then separated from its diastereomer. In a similar manner, vinyl bromide 28 provides 29c. Coupling of the free amine resulting from 27 or 29 with 11 (Scheme 2), followed by epoxidation, provides the compounds of formula I wherein D comprises an oxirane (epoxide) moiety.

Scheme 6 illustrates an alternate preparation of intermediates 32 useful for the preparation of compounds of formula I wherein D comprises an oxirane (epoxide) moiety. Coupling of 32 with 11 (Scheme 2), followed by epoxidation, provides the compounds of formula I wherein D comprises an oxirane (epoxide) moiety.

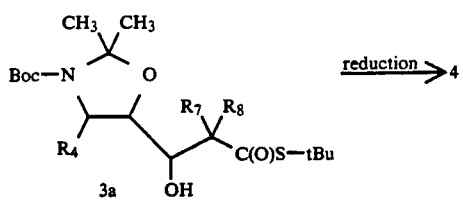

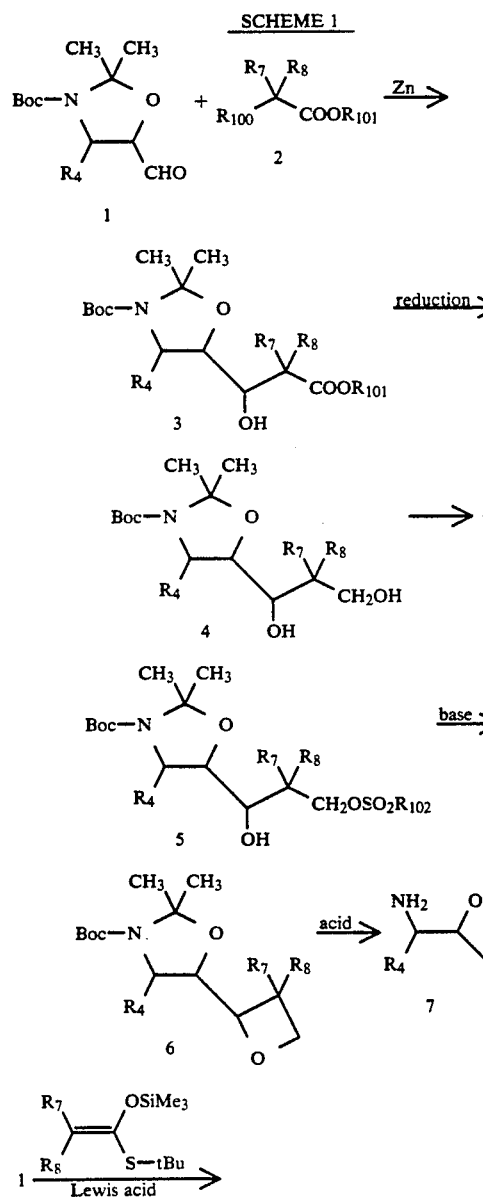

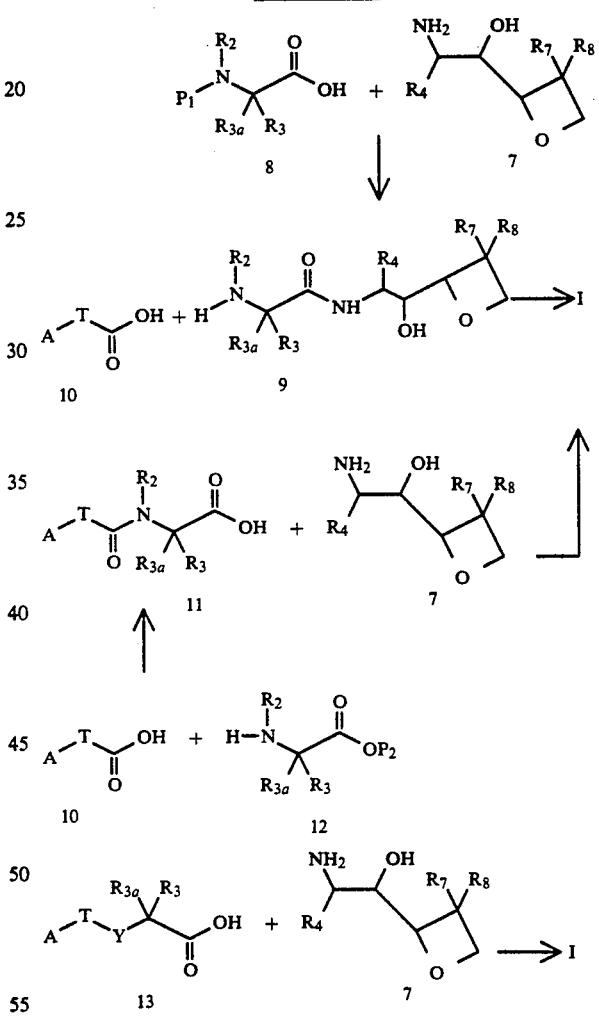

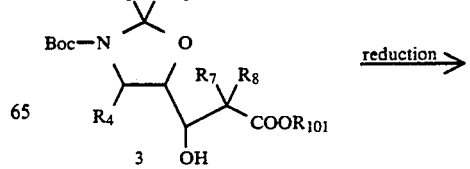

-continued
SCHEME 3

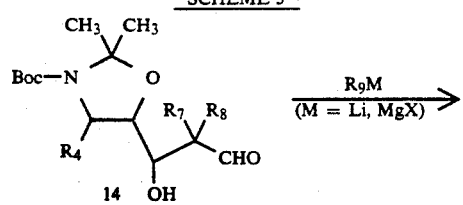

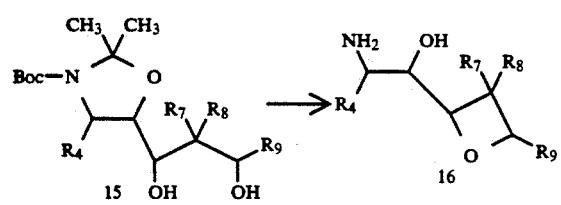

SCHEME 4

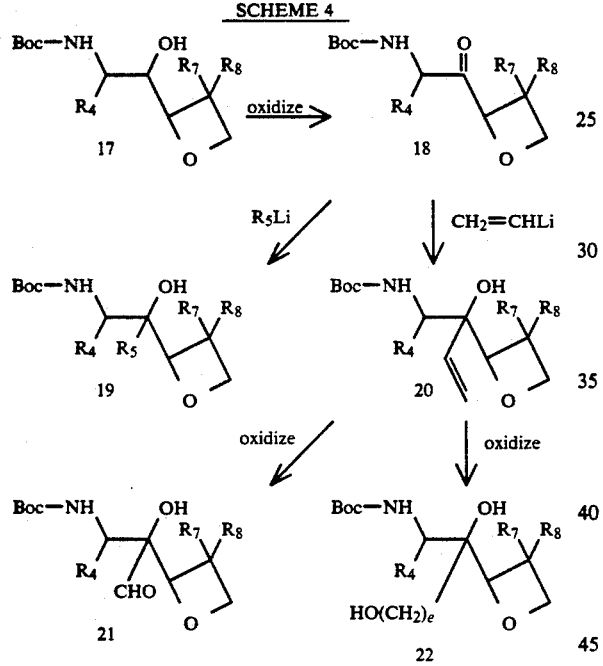

SCHEME 5

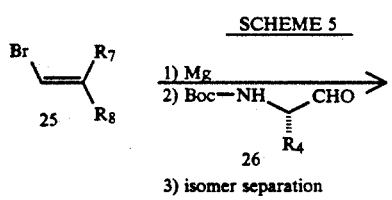

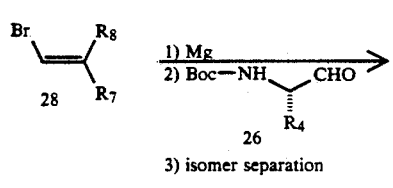

-continued
SCHEME 5

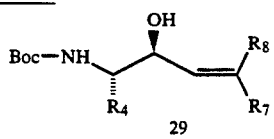

SCHEME 6

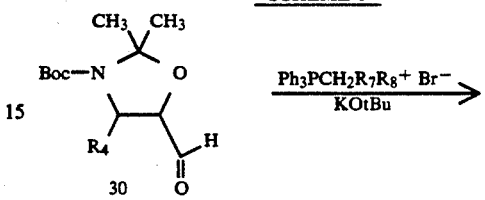

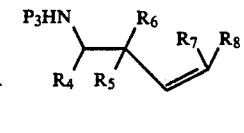

Intermediates useful for the preparation of the compounds of the invention are compounds of the formula:

![structures 40]

wherein $P_3$ is hydrogen or an N-protecting group;
$R_4$ is lower alkyl, cycloalkylalkyl or arylalkyl;
$R_5$ is hydrogen, loweralkyl, hydroxyalkyl, loweralkenyl or formyl;
$R_6$ is —OH or —NH$_2$;
$R_7$ is hydrogen or loweralkyl;
$R_8$ is hydrogen, loweralkyl, hydroxyalkyl, alkoxyalkyl, thioalkoxyalkyl, haloalkyl, aminoalkyl, alkylaminoalkyl, dialkylaminoalkyl, cycloalkyl, cycloalkylalkyl, loweralkenyl, alkynyl, aryl, arylalkyl, heterocyclic or heterocyclicalkyl; or $R_7$ and $R_8$ taken together —(CH$_2$)$_n$— wherein n is 3–6; and $R_9$ is hydrogen or loweralkyl; or an acid addition salt thereof.

The following Examples will serve to further illustrate preparation of the compounds of the invention.

EXAMPLE 1

(4S,5R,1'S,2'R)-3-(tert-Butyloxycarbonyl)-4-(cyclohexylmethyl)-2,2-(dimethyl)-5-[1'-hydroxy-2'-methoxycarbonyl-3'-(methyl)butyl]oxazolidine To (4S,5R)-3-(tert-butyloxycarbonyl)-4-(cyclohexylmethyl)-2,2-(dimethyl)oxazolidine-5-carboxaldehyde (0.800 g, 2.46 mmol, Rosenberg et al., *J. Med. Chem.*, 1990, 33, 1582) in tetrahydrofuran (10 mL) was added methyl 2-bromoisovalerate (0.720 g, 3.67 mmol) and zinc (0.400 g, 6.12 mmol). The mixture was placed in an ultrasonic cleaning bath for 1 h, and then was diluted with ethyl acetate and filtered. The mixture was washed with saturated NaHCO$_3$ solution, water, and brine, and then was dried over Na$_2$SO$_4$ and evaporated. Chromatography of the residue on silica gel with 10–15% ethyl acetate in hexane provided 0.324 g (30%) of the 2′R-isomer as an oil followed by 0 464 g (43%) of the 2′S-isomer as a solid.

2′R-Isomer: TLC (20% ethyl acetate/80% hexane) R$_f$=0.55; $^1$H-NMR (CDCl$_3$) 4.20–4.10 (m, 1H), 3.76 (s, 3H), 3.73–3.62 (m, 2H), 3.53–3.43 (m, 1H), 2.65–2.55 (m, 1H), 2.23–2.18 (m, 1H), 1.53 (br s, 6H), 1.48 (s, 9H), 1.04 (d, 3H), 0.98 (d, 3H).

2′S-Isomer: m.p. 109°–110° C.; TLC (20% ethyl acetate/80% hexane) R$_f$=0.46; $^1$H-NMR (CDCl$_3$) 4.16–4.05 (m, 1H), 3.95–3.88 (m, 1H), 3.80 (dd, 1H), 3.70 (s, 3H), 2.90–2.80 (m, 1H), 2.67 (dd, 1H), 2.33–2.21 (m, 1H), 1 51 (s, 3H), 1.50 (s, 3H), 1.47 (s, 9H), 1.07 (dd, 3H), 0.99 (dd, 3H).

Anal. (C$_{24}$H$_{43}$NO$_6$)

Calcd: C, 65.28; H, 9.81; N, 3.17 Found: C, 65.18; H, 9.73; N, 3.13.

EXAMPLE 2

(4S,5R,1′S,2′R)-3-(tert-Butyloxycarbonyl)-4-(cyclohexylmethyl)-2,2-(dimethyl)-5-[2′-ethoxycarbonyl-1′-(hydroxy)pentyl]oxazolidine Using the procedure of Example 1 and replacing methyl 2-bromoisovalerate with ethyl 2-bromopentanoate gave, after chromatography on silica gel with 10–20% ethyl acetate in hexane, the 2′R-isomer (27%) followed by the 2′S-isomer (42%), both as oils.

2′R-Isomer: TLC (20% ethyl acetate/80% hexane) R$_f$=0.56; $^1$H-NMR (CDCl$_3$) 4.32–4.18 (m, 3H), 3.70–3.60 (m, 2H), 3.55–3.46 (m, 1H), 2.93–2.83 (m, 1H), 1.52 (br s, 6H), 1.47 (s, 9H), 1.31 (t, 3H), 0.94 (t, 3H).

2′S-Isomer: TLC (20% ethyl acetate/80% hexane) R$_f$=0.48; $^1$H-NMR (CDCl$_3$) 4.25–4.08 (m, 3H), 3.87–3.78 (m, 1H), 3.72 (d, 1H), 2.95–2.80 (m, 2H), 1.54 (s, 3H), 1.52 (s, 3H), 1.48 (s, 9H), 1.28 (t, 3H), 0.94 (t, 3H).

EXAMPLE 3

(4S,5R,1′S,2′R)-3-(tert-Butyloxycarbonyl)-4-(cyclohexylmethyl)-2,3-(dimethyl)-5-[1′-hydroxy-2′-methoxycarbonyl-4-(methyl)pentyl]oxazolidine Using the procedure of Example 1 and replacing methyl 2-bromoisovalerate with methyl 2-bromoisocaproate gave, after chromatography on silica gel with 10–20% ethyl acetate in hexane, the 2′R-isomer (22%) as a solid followed by the 2′S-isomer (34%), as an oil.

2′-Isomer: m.p. 95°–97° C.; TLC (20% ethyl acetate/80% hexane) R$_f$=0.54; $^1$H-NMR (CDCl$_3$) 4.20–4.10 (m, 1H), 3.74 (s, 3H), 3.65–3.53 (m, 2H), 3.53–3.42 (m, 1H), 3.05–2.95 (m, 1H), 1.52 (br s, 6H), 1.48 (s, 9H), 0.95 (d, 3H), 0.92 (d, 3H), Anal. (C$_{25}$H$_{45}$NO$_6$) Calcd: C, 65.90; H, 9.95; N, 3.07 Found: C, 65.99; H, 10.03; N, 3.10.

2′S-Isomer: TLC (20% ethyl acetate/80% hexane) R$_f$=0.44; $^1$H-NMR (CDCl$_3$) 4.10–4.00 (m, 1H), 3.86–3.79 (m, 1H), 3.73–3.67 (m, 1H), 3.71 (s, 3H), 2.94 (br d, 1H), 1.54 (s, 3H), 1.52 (s, 3H), 1.48 (s, 9H), 0.93 (d, 6H).

EXAMPLE 4

(4S,5R,1′S)-5-[2′-Benzyloxycarbonyl-1′-(hydroxy)ethyl]-3-(tert-butyloxycarbonyl)-4-(cyclohexylmethyl)-2,2-(dimethyl)oxazolidine Using the procedure of Example 1 and replacing methyl 2-bromoisovalerate with benzyl bromoacetate gave, after chromatography on silica gel with 20% ethyl acetate in hexane, the desired product (50%) as a solid: m.p. 91°–93° C.; TLC (50% ethyl acetate/50% hexane) R$_f$=0.54; $^1$H-NMR (CDCl$_3$) 7.42–7.33 (m, 5H), 5.17 (s, 2H), 4.17–4.03 (m, 1H), 4.00–3.88 (m, 1H), 3.67 (d, 1H), 3.30–3.20 (br, 1H), 2.90 (dd, 1H), 2.54 (dd, 1H), 1.52 (s, 3H), 1.51 (s, 3H), 1.48 (s, 9H).

Anal. (C$_{27}$H$_{41}$NO$_6$) Calcd: C, 68.18; H, 8.69; N, 2.94 Found: C, 67.83; H, 8.57; N, 2.86.

EXAMPLE 5

(4S,5R,1′S)-3-(tert-Butyloxycarbonyl)-4-(cyclohexylmethyl)-2,2-(dimethyl)-5-[2′-ethoxycarbonyl-1′-hydroxy-2′-(methyl)propyl]oxazolidine Using the procedure of Example 1 and replacing methyl 2-bromoisovalerate with ethyl 2-bromoisobutyrate gave, after chromatography on silica gel with 8–10% ethyl acetate in hexane, the desired product (65%) as an oil: TLC (20% ethyl acetate/80% hexane) R$_f$=0.54; $^1$H-NMR (CCDl$_3$) 4.30–4.08 (m, 3H), 3.83 (dd, 1H), 3.36 (dd, 1H), 2.78–2.88 (br, 1H), 1.48 (s, 15H), 1.35–1.22 (m, 9H).

EXAMPLE 6

(4S,5R,1′S,2′R,)-3-(tert-Butyloxycarbonyl)-4-(cyclohexylmethyl-2,2-(dimethyl)-5-[1′-hydroxy-2′-(methoxycarbonyl)propyl]oxazolidine Using the procedure of Example 1 and replacing methyl 2-bromoisovalerate with methyl 2-bromopropionate gave, after chromatography on silica gel with 15–25% ethyl acetate in hexane, the 2R-isomer (18%) as a solid followed by the 2S-isomer (20%), as an oil.

2′R-Isomer: m.p. 88°–91° C.; TLC (20% ethyl acetate/80% hexane) R$_f$=0.28 $^1$H-NMR (CDCl$_3$) 4.23–4.06 (m, 1H), 3.80 –3.62 (m, 1H), 3.73 (s, 3H), 3.50–3.34 (m, 1H), 3.08–2.94 (m, 1H), 1.52 (s, 6H), 1.47 (s, 9H), 1.38 (d, 3H).

Anal. (C$_{22}$H$_{39}$NO$_6$) Calcd: C, 63.90; H, 9.50; N, 3.39 Found: C, 64.18; H, 9.80; N, 3.46.

2′S-Isomer: TLC (20% ethyl acetate/80% hexane) R$_f$=0.23; $^1$H NMR (CDCl$_3$) 4.20–3.42 (m, 3H), 3.77–3.60 (m, 1H), 3.72 (s, H), 3.03–2.87 (m, 1H), 2.74–2.45 (br, 1H), 1.53 (br s, 6H), 1.48 (s, 9H).

EXAMPLE 7

(4S,5R,1′S,2′R,3′RS)-3-(tert-Butyloxycarbonyl)-4-(cyclohexylmethyl)-2,2-(dimethyl)-6-[2′-ethoxycarbonyl-1′-hydroxy-3′-(trifluoromethyl)butyl]oxazolidine Using the procedure of Example 1 and replacing methyl 2-bromoisovalerate with ethyl 2-bromo-4,4,4-trifluoroisovalerate gave, after chromatography on silica gel with 15–20% ethyl acetate in hexane, the 2R-isomer (28%) as a solid followed by the 2S-isomer (33%), as an oil.

2′R-Isomer m.p. 86°–89 ° C.; TLC (20% ethyl acetate/80% hexane) R$_f$=0.44; $^1$H NMR (CDCl$_3$) 4.37–4.08 (m, 3H), 3.74–3.63 (m, 1H), 3.60–3.45 (m, 1H), 3.08–2.98 (m, 1H), 2.96–2.77 (m, 1H), 1.52 (br s, 6H), 1.48 (s, 9H).

Anal. ($C_{25}H_{42}NO_6F_3$) Calcd: C, 58.92; H, 8.31; N, 2.75 Found: C, 59.24; H, 8.54; N, 2.73.

2'S-Isomer: TLC (20% ethyl acetate/80% hexane) $R_f$=0.33; $^1$H NMR (CDCl$_3$) 4.28–4.06 (m, 3H), 4.02–3.67 (m, 2H), 3.17–2.89 (m, 2H), 1.54 (s, 3H), 1.52 (s, 3H), 1.47 (s, 9H).

EXAMPLE 8

1(tert-Butylthio)-1-(trimethylsilyloxy)but-1-ene

To tert-Butylthiobutyrate (4.995 g, 31.2 mmol) in dichloromethane (30 mL) at 0° C. was added trimethylsilyl trifluoromethanesulfonate (6.10 mL, 31 mmol) and triethylamine (5.2 mL, 37 mmol). The cooling bath was removed and the mixture was stirred at ambient temperature for 45 min. After evaporation of the solvent, the lower layer was separated and discarded and the upper layer was distilled to afford 6.116 g (84%) of the desired product: b.p. 95°–96° C. (11 mm); 1H-NMR (CDCl$_3$) 5.21 (t, 1H), 2.18 (dq, 2H), 1.37 (s, 9H), 0.94 (t, 3H), 0.21 (s, 9H).

EXAMPLE 9

(4S,5R,1'S,2'R)-3-(tert-Butyloxycarbonyl)-5-[2'-tert-butylthiocarbonyl-1'-(hydroxy)butyl]-4-(cyclohexylmethyl)-2,2-(dimethyl)oxazolidine To (4S,5R)-3-(tert-butyloxycarbonyl)-4-(cyclohexylmethyl)-2,2-(dimethyl)oxazolidine-5-carboxaldehyde (5 827 g, 17.90 mmol, Rosenberg et al., *J. Med. Chem.*, 1990, 33, 1582) was added the resultant compound from Example 8 (6.116 g, 26.30 mmol) in dichloromethane (60 mL). The mixture was cooled to −78° C. and was treated with borontrifluoride etherate (2.30 mL, 18.7 mmol). After 1 h, the mixture was transferred via cannula into a rapidly stirring solution of pH 7 phosphate buffer (120 mL) at 0° C. The mixture was partitioned, the aqueous phase was extracted with dichloromethane, and the combined organic layers were dried over MgSO$_4$ and evaporated. Chromatography of the residue on silica gel with 3–5% ethyl acetate in hexane afforded 4.463 g (51%) of the desired product as a solid: m.p. 89°–90° C.; TLC (20% ethyl acetate/80% hexane) $R_f$=0.73; $^1$H-NMR (CDCl$_3$) 4.23–4.10 (m, 1H), 3.69–3.59 (m, 1H), 3.57–3.47 (m, 2H), 2.93–2.85 (m, 1H), 1.53 (s, 3H), 1.52 (s, 3H), 1.48 (s, 9H), 1.46 (s, 9H), 1.01 (t, 3H).

Anal. ($C_{26}H_{47}NO_5S\cdot 0.25\ H_2O$) Calcd: C, 63.70; H, 9.77; N, 2.86 Found: C, 63.88; H, 9.56; N, 2.90.

EXAMPLE 10

(4S,5R,1'S,2'S)-3-(tert-Butyloxycarbonyl)-4-(cyclohexylmethyl)-2,2-(dimethyl)-5-[1'-hydroxy-2'-hydroxymethyl-3'-(methyl)butyl]oxazolidine To the resultant 2'R-isomer from Example 1 (185 mg, 0.419 mmol) in ethanol (0.8 mL) was added CaCl$_2$ (85.0 mg, 0.842 mmol). After the mixture became homogeneous, tetrahydrofuran (0.5 mL) and NaBH$_4$ (63.0 mg, 0.842 mmol) were added. After 24 h, the mixture was poured into ether which was washed sequentially with 0.5M H$_3$PO$_4$, saturated NaHCO$_3$ solution, and brine, and then was dried over MgSO$_4$ and evaporated. Chromatography of the residue on silica gel with 15% ethyl acetate in hexane provided 122.2 mg (71%) of the desired product as a foam: TLC (20% ethyl acetate/80% hexane) $R_f$=0.26; $^1$H-NMR (CDCl$_3$) 4.20–4.06 (m, 2H), 4.04–3.96 (m, 1H), 3.91 (d, 1H), 3.85–3.75 (m, 1H), 3.22–3.05 (br, 1H), 2.19–2.04 (m, 1H), 1.52 (s, 6H), 1.48 (s, 9H), 1.05 (d, 3H), 1.04 (d, 3H).

EXAMPLE 11

(4S,5R,1'S,2'R)-3-(tert-Butyloxycarbonyl)-4-(cyclohexylmethyl)-2,2-(dimethyl)-5-[1'-hydroxy-2'-hydroxymethyl-3'-(methyl)butyl]oxazolidine Using the procedure of Example 10 with the resultant 2'S-isomer from Example 1 gave, after chromatography on silica gel with 25% ethyl acetate in hexane, the desired product (69%) as a foam: TLC (20% ethyl acetate/80% hexane) $R_f$=0.12; $^1$H-NMR (CDCl$_3$) 4.22–4.05 (m, 1H), 3.95–3.77 (m, 3H), 1.55 (s, 3H), 1.52 (s, 3H), 1.48 (s, 9H), 1.04 (d, 3H), 0.98 (d, 3H).

EXAMPLE 12

(4S,5R,1'S,2'S)-3-(tert-Butyloxycarbonyl)-4-(cyclohexylmethyl)-2,2-(dimethyl)-5-[1'-hydroxy-2'-(hydroxymethyl)pentyl]oxazolidine Using the procedure of Example 10 with the resultant 2'R-isomer from Example 2 gave, after chromatography on silica gel with 12% ethyl acetate in hexane, the desired product (81%) as a foam: TLC (20% ethyl acetate/80% hexane) $R_f$=0.25; $^1$H-NMR (CDCl$_3$) 4.17–4.07 (m, 2H), 3.89 (d, 1H), 3.83–3.74 (m, 1H), 3.65–3.57 (m, 1H), 3.10–2.95 (br, 1H), 1.51 (s, 6H), 1.48 (s, 9H), 0.95 (t, 3H).

EXAMPLE 13

Using the procedure of Example 10 with the resultant 2'R-isomer from Example 3 gave, after chromatography on silica gel with 12% ethyl acetate in hexane, the desired product (87%) as a foam: TLC (20% ethyl acetate/80% hexane) $R_f$=0.31; $^1$H-NMR (CDCl$_3$) 4.18–4.07 (m, 2H), 3.89 (d, 1H), 3.80–3.70 (m, 1H), 3.60–3.50 (m, 1H), 3.10–3.00 (br, 1H), 1.52 (s, 6H), 1.48 (s, 9H), 0.92 (d, 6H).

(4S,5R,1'R)-3-(tert-Butyloxycarbonyl)-4-(cyclohexylmethyl)-5-[1',3'-(dihydroxy)propyl]-2,2-(dimethyl)oxazolidine Using the procedure of Example 10 with the resultant compound from Example 4 gave, after chromatography on silica gel with 50% ethyl acetate in hexane, the desired product (83%) as a solid: m.p. 130°–131° C.; TLC (50% ethyl acetate/50% hexane) $R_f$=0.23; $^1$H-NMR (CDCl$_3$) 4.15–3.95 (m, 2H), 3.95–3.77 (m, 2H), 3.68 (dd, 1H), 3.00–2.85 (br, 1H), 1.54 (s, 3H), 1.52 (s, 3H), 1.48 (s, 9H).

EXAMPLE 15

(4S,5R,1'S)-3-(tert-Butyloxycarbonyl)-4-(cyclohexylmethyl)-2,2-(dimethyl)-5-[1'-hydroxy-2'-hydroxymethyl-2'-(methyl)propyl]oxazolidine Using the procedure of Example 10 with the resultant compound from Example 5 gave, after chromatography on silica gel with 20% ethyl acetate in hexane, the desired product as a solid: m.p. 140°–142° C.; TLC (20% ethyl acetate/80% hexane) $R_f$=0.12; TLC (50% ethyl acetate/50% hexane) $R_f$=0.59; $^1$H-NMR (CDCl$_3$) 4.33–4.25 (m, 1H), 3.90 (dd, 1H), 3.72–3.62 (m, 1H), 3.53–3.38 (m, 2H), 2.80–2.50 (br, 2H), 1.60 (s, 3H), 1.52 (s, 3H), 1.48 (s, 9H), 1.05 (s, 3H), 1.00 (s, 3H).

EXAMPLE 16

(4S,5R,1'S,2'S)-3-(tert-Butyloxycarbonyl)-4-(cyclohexylmethyl)-2,2-(dimethyl)-5-[1'-hydroxy-2'-(hydroxymethyl)propyl]oxazolidine Using the procedure of Example 10 with the resultant 2'R-isomer from Example 6 gave, after chromatography on silica gel with 20% ethyl acetate in hexane, the desired product (90%) as a solid: m.p. 101°–103° C.; TLC (50% ethyl acetate/50% hexane) $R_f=0.45$; $^1$H NMR (CDCl$_3$) 4.17–3.98 (m, 2H), 3.86 (dd, 1H), 3.77–3.67 (m, 1H), 3.58–3.48 (m, 1H), 2.90–2.75 (br, 1H), 1.53 (s, 3H), 1.52 (s, 3H), 1.47(s, 9H), 1.16 (d, 3H).

Anal. (C$_{21}$H$_{39}$NO$_5$) Calcd: C, 65.42; H, 10.20; N, 3.63 Found: C, 65.46; H, 10.38; N, 3.66.

EXAMPLE 17

(4S,5R,1'S,2'S,3'RS)-3-(tert-Butyloxycarbonyl)-4-(cyclohexylmethyl)-2,2-(dimethyl)-5-[1'-hydroxy-2'-hydroxymethyl-3'-(trifluoromethyl)butyl]oxazolidine Using the procedure of Example 10 with the resultant 2'-isomer from Example 7 gave, after chromatography on silica gel with 15% ethyl acetate in hexane, the desired product (86%) as a solid: m.p. 145°–146° C.; TLC (20% ethyl acetate/80% hexane) $R_f=0.24$; $^1$H NMR (CDCl$_3$) 4.30–3.95 (m, 3H), 3.92 (d, 1H), 3.84–3.69 (m, 1H), 3.45–3.24 (br, 1H), 2.92–2.70 (m, 1H), 1.52 (br s, 6H), 1.48 (s, 9H), 1.33 (dd, 3H).

Anal. (C$_{23}$H$_{40}$NO$_5$F$_3$) Calcd: C, 59.08; H, 8.62; N, 3.00 Found: C, 59.03; H, 8.76; N, 2.99.

EXAMPLE 18

(4S,5R,1'S,2'S)-3-(tert-Butyloxycarbonyl)-4-(cyclohexylmethyl)-2,2-(dimethyl)-5-[1'-hydroxy-2'-(hydroxymethyl)butyl]oxazolidine The resultant compound from Example 9 (2.0015 g, 4.121 mmol) in tetrahydrofuran (40 mL) at 0° C. was treated with LiBH$_4$ in tetrahydrofuran (5.0 mL, 10 mmol, 2.0M). After 4 h at 0° C. and 12 h at ambient temperature, the reaction was concentrated and quenched with 0.5M H$_3$PO$_4$. The mixture was diluted with ether and washed with water, saturated NaHCO$_3$ solution and brine, and then was dried over Na$_2$SO$_4$ and evaporated. Chromatography of the residue on silica gel with 15% ethyl acetate in hexane afforded 1.3949 g (85%) of the desired product as a foam: TLC (20% ethyl acetate/80% hexane) $R_f=0.19$; $^1$H-NMR (CDCl$_3$) 4.18–407 (m, 2H), 3.90 (d, 1H), 3.86–3.77 (m, 1H), 3.68–3.59 (m, 1H), 3.05–2.87 (br, 1H), 1.52 (s, 6H), 1.48 (s, 9H), 1.01 (t, 3H).

EXAMPLE 19

(4S,5R,1'S,2'S)-3-(tert-Butyloxycarbonyl)-4-(cyclohexylmethyl)-2,2-(dimethyl)-5-[1'-hydroxy-2'-[(p-toluenesulfonyloxy)methyl]butyl]oxazolidine The resultant compound from Example 18 (1.3949 g, 3.491 mmol) in pyridine (4 mL) at 0° C. was treated with p-toluenesulfonyl chloride (0.730 g, 3.83 mmol). After 24 h at 0° C. and 36 h at ambient temperature, the mixture was diluted with ether and washed sequentially with 0.5M H$_3$PO$_4$, water, and brine, and then was dried over MgSO$_4$ and evaporated to afford 1.8827 g (97%) of the desired product as a foam: TLC (20% ethyl acetate/80% hexane) $R_f=0.25$; $^1$H-NMR (CDCl$_3$) 7.81 (d, 2H), 7.37 (d, 2H), 4.30–4.15 (m, 2H), 4.12–4.01 (m, 1H), 3.72 (d, 1H), 3.64–3.54 (m, 1H), 2.47 (s, 3H), 1.52 (s, 3H), 1.48 (s, 3H), 1.47 (s, 9H), 0.88 (t, 3H).

EXAMPLE 20

(4S,5R,1'S,2'S)-3-(tert-Butyloxycarbonyl)-4-(cyclohexylmethyl)-2,2-(dimethyl)-5-[1'-hydroxy-3'-methyl-2'-[(p-toluenesulfonyloxy)methyl]butyl]oxazolidine Using the procedure of Example 19 with the resultant compound from Example 10 gave the desired product (94%) as a foam: TLC (20% ethyl acetate/80% hexane) $R_f=0.39$; $^1$H-NMR (CDCl$_3$) 7.82 (d, 2H), 7.37 (d, 2H), 4.34–4.25 (m, 2H), 4.13–4.02 (m, 1H), 3.73–3.67 (m, 2H), 2.47 (s, 3H), 1.54 (s, 6H), 1.47 (s, 9H), 0.97 (d, 3H), 0.88 (d, 3H).

EXAMPLE 21

(4S,5R,1'S,2'R)-3-(tert-Butyloxycarbonyl)-4-(cyclohexylmethyl)-2,2-(dimethyl)-5-[1'-hydroxy-3'-methyl-2'-[(p-toluenesulfonyloxy)methyl]butyl]oxazolidine Using the procedure of Example 19 with the resultant compound from Example 11 gave the desired product (94%) as a foam: TLC (20% ethyl acetate/80% hexane) $R_f=0.35$; $^1$H-NMR (CDCl$_3$) 7.80 (d, 2H), 7.37 (d, 2H), 4.38–4.23 (m, 1H), 4.12 (dd, 1H), 4.04–3.94 (m, 1H), 3.87–3.70 (m, 2H), 2.47 (s, 3H), 1.56 (s, 6H), 1.50 (s, 9H), 0.96 (d, 3H), 0.88 (d, 3H).

EXAMPLE 22

(4S,5R,1'S,2'S)-3-(tert-Butyloxycarbonyl)-4-(cyclohexylmethyl)-2,2-(dimethyl)-5-[1'-hydroxy-2'-[(p-toluenesulfonyloxy)methyl]pentyl]oxazolidine Using the procedure of Example 19 with the resultant compound from Example 12 gave the desired product (88%) as a foam: TLC (20% ethyl acetate/80% hexane) $R_f=0.36$; $^1$H-NMR (CDCl$_3$) 7.81 (d, 2H), 7.37 (d, 2H), 4.30–4.00 (m, 3H), 3.71 (d, 1H), 3.61–3.51 (m, 1H), 2.47 (s, 3H), 1.52 (s, 3H), 1.48 (s, 3H), 1.47 (s, 9H), 0.97 (t, 3H).

EXAMPLE 23

(4S,5R,1'S,2'S)-3-(tert-Butyloxycarbonyl)-4-(cyclohexylmethyl)-2,2-(dimethyl)-5-[1'-hydroxy-4'-methyl-2'-[(p-toluenesulfonyloxy)methyl]pentyl]oxazolidine Using the procedure of Example 19 with the resultant compound from Example 13 gave the desired product (93%) as a foam: TLC (20% ethyl acetate/80% hexane) $R_f=0.43$; $^1$H-NMR (CDCl$_3$) 7.81 (d, 2H), 7.37 (d, 2H), 4.32–4.00 (m, 3H), 3.71 (d, 1H), 3.55–3.47 (m, 1H), 2.47 (s, 3H), 1.57 (s, 3H), 1.48 (s, 3H), 1.47 (s, 9H), 0.82 (t, 3H).

EXAMPLE 24

(4S,5R,1'S)-3-(tert-Butyloxycarbonyl)-4-(cyclohexylmethyl)-2,2-(dimethyl)-5-[1'-hydroxy-3'-(p-toluenesulfonyloxy)propyl]oxazolidine Using the procedure of Example 19 with the resultant compound from Example 14 gave, after chromatography on silica gel with 15% ethyl acetate in hexane, the desired product (45%) as a foam: TLC (20% ethyl acetate/80% hexane) $R_f=0.17$; $^1$H-NMR (CDCl$_3$) 7.80 (d, 2H), 7.36 (d, 2H), 4.40–4.28 (m, 1H), 4.22–4.10 (m, 1H), 4.07–3.97 (m, 1H), 3.78–3.67 (m, 1H), 3.59 (d, 1H), 2.46 (s, 3H), 1.55 (s, 3H), 1.49 (s, 12H).

EXAMPLE 25

(4S,5R,1′S)-3-(tert-Butyloxycarbonyl)-4-(cyclohexylmethyl)-2,2-(dimethyl)-5-[1′-hydroxy-2′-[(p-toluenesulfonyloxy)methyl]propyl]oxazolidine Using the procedure of Example 19 with the resultant compound from Example 16 gave the desired product as a foam: TLC (20% ethyl acetate/80% hexane) $R_f$=0.22; $^1$H NMR (CDCl$_3$) 7.81 (d, 2H), 7.36 (d, 2H), 4.20–4.12 (m, 1H), 4.08–3.97 (m, 1H), 3.70 (dd, 1H), 3.53–3.43 (ddd, 1H), 2.46 (s, 3H), 2.31–2.27 (br, 1H), 1.48 (s, 6H), 1.47 (s, 9H), 1. 5 (d, 3H).

EXAMPLE 26

(4S,5R,1′S,2′S,3′RS)-3-(tert-Butyloxycarbonyl)-4-(cyclohexylmethyl)-2,2-(dimethyl)-5-[1′-hydroxy-2′-[(p-toluenesulfonyloxy)methyl]-3′-(trifluoromethyl)butyl]oxazolidine Using the procedure of Example 19 with the resultant compound from Example 17 gave the desired product (93%) as a foam: TLC (50% ether/50% hexane) $R_f$=35; $^1$H-NMR (CDCl$_3$) 7.82 (d, 2H), 7.37 (d, 2H), 4.46–3.65 (envelope, 5H), 2.47 (s, 3H), 1.50–1.46 (m, 15H).

EXAMPLE 27

(4S,5R,1′S)-3-(tert-Butyloxycarbonyl)-4-(cyclohexylmethyl)-2,2-(dimethyl)-5-[1′-hydroxy-2′-[(methanesulfonyloxy)methyl]-2′-(methyl)propyl]oxazolidine The resultant compound from Example 15 (57.5 mg, 0.144 mmol) in dichloromethane (1 mL) at −10° C. was treated with methanesulfonyl chloride (0.011 mL, 0.14 mmol) and triethylamine (0.022 mL, 0.16 mmol). After 1 h, the mixture was warmed to ambient temperature and stirred for an additional hour. The solvent was evaporated and the residue was taken up in ether which was washed sequentially with 0.5M H$_3$PO$_4$, saturated NaHCO$_3$ solution, and brine, and then was dried over MgSO$_4$ and evaporated to afford 0.0666 g (97%) of the desired product as a foam: TLC (50% ethyl acetate/50% hexane) $R_f$=0.63; $^1$H-NMR (CDCl$_3$) 4.38 (d, 1H), 4.23–4.12 (m, 1H), 3.90–3.83 (m, 2H), 3.52–3.45 (m, 1H), 3.03 (s, 3H), 1.58 (s, 3H), 1.51 (s, 3H), 1.49 (s, 9H), 1.15 (s, 3H), 1.02 (s, 3H).

EXAMPLE 28

(4S,5R,2′S,3′S)-3-(tert-Butyloxycarbonyl)-4-(cyclohexylmethyl)-2,2-(dimethyl)-5-[3′-(ethyl)oxetan-2′-yl]oxazolidine To the resultant compound from Example 19 (1.8827 g, 3.400 mmol) in tetrahydrofuran (30 mL) at 0° C. was added sodium bis(trimethylsilyl)amide in tetrahydrofuran (4.5 mL, 4.5 mmol, 1.0M). After 45 min, the reaction was quenched
with 0.5M H$_3$PO$_4$. The mixture was concentrated, diluted with ether, washed sequentially with 0.5M H$_3$PO$_4$, water, and brine, and then was dried over MgSO$_4$ and evaporated. Chromatography of the residue on silica gel with 10% ethyl acetate in hexane afforded 1.1386 g (88%) of the desired product as a solid: m.p. 40–41° C.; TLC (20% ethyl acetate/80% hexane) $R_f$=0.57 $^1$H-NMR (CDCl$_3$) 4.62 (dd, 1H), 4.37–4.28 (m, 1H), 4.27 (dd, 1H), 4.01 (dd, 1H), 3.90–3.78 (br m, 1H), 2.73–2.59 (m, 1H), 1.56 (s, 3H), 1.53 (s, 3H), 1.47 (s, 9H), 0.89 (t, 3H).

Anal. (C$_{22}$H$_{39}$NO$_4$) Calcd: C, 69.25; H, 10.30; N, 3.67 Found: C, 69.10; H, 10.10; N, 3.49.

EXAMPLE 29

(4S,5R,2′S,3′S)-3-(tert-Butyloxycarbonyl)-4-(cyclohexylmethyl)-2,2-(dimethyl)-5-[3′-(isopropyl)oxetan-2′-yl]oxazolidine Using the procedure of Example 28 with the resultant compound from Example 20 gave, after chromatography on silica gel with 10% ethyl acetate in hexane, the desired product (92%) as an oil: TLC (20% ethyl acetate/80% hexane) $R_f$=0.56; $^1$H-NMR (CDCl$_3$) 4.58 (dd, 1H), 4.42–4.30 (m, 1H), 4.30 (dd, 1H), 4.01 (dd, 1H), 4.00–3.84 (br m, 1H), 2.46–2.32 (m, 1H), 1.58 (s, 3H), 1.52 (s, 3H), 1.46 (s, 9H), 0.92 (d, 3H), 0.88 (d, 3H).

Anal. (C$_{23}$H$_{41}$NO$_4$) Calcd: C, 69.83; H, 10.45; N, 3.54 Found: C, 70.10; H, 10.84; N, 3.55.

EXAMPLE 30

(4S,5R,2′S,3′R)-3-(tert-Butyloxycarbonyl)-4-(cyclohexylmethyl)-2,2-(dimethyl)-5-[3′-(isopropyl)oxetan-2′-yl]oxazolidine Using the procedure of Example 28 with the resultant compound from Example 21 gave, after chromatography on silica gel with 10% ethyl acetate in hexane, the desired product (74%) as a solid: m.p. 99°–100° C.; TLC (20% ethyl acetate/80% hexane) $R_f$=0.51 $^1$H-NMR (CDCl$_3$) 4.62–4.50 (m, 2H), 4.37–4.28 (m, 2H), 3.94–3.81 (br m, 1H), 2.94–2.78 (m, 1H), 2.20–2.03 (m, 1H), 1.53 (s, 3H), 1.52 (s, 3H), 1.46 (s, 9H), 1.00 (d, 3H), 0.76 (d, 3H).

Anal. (C$_{23}$H$_{41}$NO$_4$) Calcd: C, 69.83; H, 10.45; N, 3.54 Found: C, 69.91; H, 10.48; N, 3.53.

EXAMPLE 31

(4S,5R,2′S,3′S)-3-(tert-Butyloxycarbonyl)-4-(cyclohexylmethyl)-2,2-(dimethyl)-5-[3′-(propyl)oxetan-2′-yl]oxazolidine Using the procedure of Example 28 with the resultant compound from Example 22 gave, after chromatography on silica gel with 10% ethyl acetate in hexane, the desired product (90%) as a solid: m.p. 76°–77° C.; TLC (20% ethyl acetate/80% hexane) $R_f$=0.60; $^1$H-NMR (CDCl$_3$) 4.62 (dd, 1H), 4.37–4.28 (m, 1H), 4.27 (dd, 1H), 4.00 (dd, 1H), 3.95–3.75 (br m, 1H), 2.82–2.67 (m, 1H), 1.55 (s, 3H), 1.52 (s, 3H), 1.47 (s, 9H), 0.90 (t, 3H).

Anal. (C$_{23}$H$_{41}$NO$_4$) Calcd: C, 69.83; H, 10.45; N, 3.5 Found: C, 70.24; H, 10.45; N, 3.56.

EXAMPLE 32

(4S,5R,2′S,3′S)-3-(tert-Butyloxycarbonyl)-4-(cyclohexylmethyl)-2,2-(dimethyl)-5-[3′-(isobutyl)oxetan-2′-yl]oxazolidine Using the procedure of Example 28 with the resultant compound from Example 23 gave, after chromatography on silica gel with 10% ethyl acetate in hexane, the desired product (95%) as a solid: m.p. 77°–78° C.; TLC (20% ethyl acetate/80% hexane) $R_f$=0.67 $^1$H-NMR (CDCl$_3$) 4.62 (dd, 1H), 4.38–4.28 (m, 1H), 4.27 (dd, 1H), 4.00 (dd, 1H), 3.95–3.73 (br m, 1H), 0.88 (d, 3H), 0.86 (d, 3H).

Anal. (C$_{24}$H$_{43}$NO$_4$) Calcd C, 70.38; H, 10.58; N, 3.42 Found: C, 70.65; H, 10.91; N, 3.37.

EXAMPLE 33

(4S,5R,2'S)-3-(tert-Butyloxycarbonyl)-4-(cyclohexylmethyl)-2,2-(dimethyl)-5-(oxetan-2'-yl)oxazolidine Using the procedure of Example 28 with the resultant compound from Example 24 gave, after chromatography on silica gel with 10% ethyl acetate in hexane, the desired product (84%) as a solid: m.p. 70°–72° C.; TLC (20% ethyl acetate/80% hexane) $R_f$=0.37 $^1$H-NMR (CDCl$_3$) 4.78–4.62 (m, 2H), 4.56 (dd, 1H), 4.03 (dd, 1H), 3.79 (br d, 1H), 2.77–2.62 (m, 1H), 2.62–2.47 (m, 1H), 1.56 (s, 3H), 1.52 (s, 3H), 1.47 (s, 9H), Anal. (C$_{20}$H$_{35}$NO$_4$) Calcd: C, 67.95; H, 9.98; N, 3.96 Found: C, 67.80; H, 9.96; N, 3.91.

(4S,5R,2'S,3'S)-3-(tert-Butyloxycarbonyl)-4-(cyclohexylmethyl)-2,2-(dimethyl)-5-[3'-(methyl)oxetan-2'-yl]oxazolidine Using the procedure of Example 28 with the resultant compound from Example 25 gave, after chromatography on silica gel with 10% ether in hexane, the desired product (74%) as a solid: m.p. 73°–74° C.; TLC (20% ethyl acetate/80% hexane) $R_f$=0.43; $^1$H NMR (CDCl$_3$) 4.64 (dd, 1H), 4.34–4.26 (m, 1H), 4.23 (dd, 1H), 4.00 (dd, 1H), 3.87–3.73 (br, 1H), 2.94–2.78 (m, 1H), 1.55 (s, 3H), 1.52 (s, 3H), 1.47 (s, 9H), 1.28 (d, 3H).

Anal. (C$_{21}$H$_{37}$NO$_4$) Calcd: C, 68.63; H, 10.15; N, 3.98 Found: C, 68.68; H, 9.93; N, 3.78.

EXAMPLE 35

(4S,5R,2'S,3'S)-3-(tert-Butyloxycarbonyl)-4-(cyclohexylmethyl)-2,2-(dimethyl)-5-[3'-(1,1,1-trifluoroisopropyl)oxetan-2'-yl]oxazolidine Using the procedure of Example 28 with the resultant compound from Example 26 gave, after chromatography on silica gel with 15% ether in hexane, the desired product (50%) as a solid: m.p. 102°–104° C.; TLC (20% ethyl acetate/80% hexane) $R_f$=0.49; $^1$H NMR (CDCl$_3$) 4.63 (dd, 1H), 4.51–4.37 (m, 2H), 4.10–3.80 (br, 1H), 4.02 (dd, 1H), 2.93–2.78 (m, 1H), 2.69–2.51 (m, 1H), 1.58 (s, 1H), 1.53 (s, 1H), 1.47 (s, 9H), 1.16 (d, 3H). Anal. (C$_{23}$H$_{38}$NO$_4$F$_3$.0.25 H$_2$O) Calcd C, 60.84; H, 8.55; N, 3.08 Found: C, 61.04; H, 8.71; N, 3.05.

EXAMPLE 36

(4S,5R,2'S)-3-(tert-Butyloxycarbonyl)-4-(cyclohexylmethyl)-2,2-(dimethyl)-5-[3',3'-(dimethyl)oxetan-2'-yl]oxazolidine Using the procedure of Example 28 with the resultant compound from Example 27 gave, after chromatography on silica gel with 7% ethyl acetate in hexane, the desired product (63%) as a solid: m.p. 96.0°–96.5° C.; TLC (20% ethyl acetate/80% hexane) $R_f$=0.60 $^1$H-NMR (CDCl$_3$) 4.36–4.22 (m, 2H), 4.18–4.03 (m, 2H), 3.87–3.72 (br m, 1H), 1.51 (s, 6H), 1.47 (s, 9H), 1.30 (s, 3H), 1.29 (s, 3H).

EXAMPLE 37

Boc-Phe-His Benzyl Ester

To a mixture of Boc-Phe-OH (0.500 g, 1.88 mmol), 1-hydroxybenzotriazole (0.730 g, 5.43 mmol) and histidine benzyl ester di-p-toluenesulfonic acid salt (1.00 g, 1.70 mmol, Jones et al., *Synth. Commun.*, 1986, 16, 1515) in dimethylformamide (7 mL) at −23° C. was added N-methylmorpholine (0.375 mL, 3.41 mmol) and 1-(3-dimethylaminopropyl)-3-ethylcarbodiimide hydrochloride (0.361 g, 1 88 mmol). After stirring at −23° C. for 2 h and at ambient temperature overnight, the mixture was poured into saturated NaHCO$_3$ solution and extracted into ethyl acetate which was washed with water and brine, and then was dried over Na$_2$SO$_4$ and evaporated. Chromatography of the residue on silica gel with 3% methanol in chloroform afforded 0.710 g (85%) of the desired product: TLC (10% methanol/90% chloroform) $R_f$=0.46.

Anal. (C$_{27}$H$_{32}$N$_4$O$_5$.0.25 H$_2$O) Calcd: C, 65.24; H, 6.59; N, 11.27 Found: C, 65.41; H, 6.46; N, 11.25.

EXAMPLE 38

Boc-Phe-(imidazole-Boc)His Benzyl Ester

The resultant compound from Example 37 (0.352 g, 0.715 mmol) and di-tert-butyldicarbonate (0.156 g, 0.715 mmol) in dichloromethane (10 mL) were stirred at ambient temperature for 4 h. The solvent was evaporated to afford 0.423 g (100%) of a foam.

Anal. (C$_{32}$H$_{40}$N$_4$O$_7$) Calcd: C, 64.85; H, 6.80; N, 9.45 Found C, 64.53; H, 6.82; N, 9.32.

EXAMPLE 39

Boc-Phe-(imidazole-Boc)His-OH

The resultant compound from Example 38 (0.415 g, 0.700 mmol) and 10% palladium on carbon (0.325 g) in methanol (5 mL) were stirred under a hydrogen atmosphere for 90 min. The mixture was filtered and evaporated to afford 0.328 g (93%) of a foam.

Anal. (C$_{25}$H$_{34}$NO$_4$O$_7$.0.5 H$_2$O) Calcd: C, 58.70; H, 6.90; N, 10.9 Found C, 58.49; H, 6.71; N, 10.86.

EXAMPLE 40

Boc-Phe-His Amide of (1R,2S,2'S,3'S)-2-Amino-3-cyclohexyl-1-[3'-(ethyl)oxetan-2'-yl]-1-(hydroxy)propane The resultant compound from Example 28 (55.0 mg, 0.144 mmol) in dichloromethane (2 mL) at 0° C. was treated with cold trifluoroacetic acid (2 mL) and the mixture was stirred at 0° C. for 3 h. The solvent was evaporated, tetrahydrofuran (1 mL) and water (1 mL) were added, and the mixture was stirred at 0° C. for 2 h and then at ambient temperature for 14 h. The mixture was concentrated, taken up in 2M HCl, and washed with ether. The aqueous phase was made basic with Na$_2$CO$_3$, saturated with NaCl, and extracted with chloroform which was dried over Na$_2$SO$_4$ and evaporated to afford 31.2 mg (90%) of the free amine.

To Boc-Phe-(imidazole-Boc)His-OH (63.0 mg, 0.125 mmol) in dichloromethane (1 mL) at −10° C. was added N-methylmorpholine (0.015 mL, 0.14 mmol) followed by isobutylchloroformate (0.017 mL, 0.13 mmol). After 3 min the above amine in dichloromethane (2 mL) was added and the mixture was stirred at −10° C. for 15 min and then at ambient temperature for 2 h. The solvent was evaporated and the residue was taken up in 3:1:1 acetic acid/tetrahydrofuran/water and stirred at 48°–50° C. for 14 h. The solvent was evaporated and the residue was taken up in ethyl acetate which was washed with saturated NaHCO$_3$ solution and brine, and then was dried over Na$_2$SO$_4$ and evaporated. Chromatography of the residue on silica gel with 3% methanol in chloroform afforded 16.7 mg (21%) of the desired product: TLC (15% methanol/85% chloroform) $R_f$=0.49; $^1$H NMR (CDCl$_3$) 7.53 (s, 1H), 7.38–7.18 (m, 5H), 6.87 (s, 1H), 6.53 (br d, 1H), 4.98 (br d, 1H), 4.61 (dd, 1H), 1.48(s, 9H), 0.87 (t, 3H).

Anal. ($C_{34}H_{51}N_5O_6 \cdot H_2O$) Calcd: C, 63.43; H, 8.30; N, 10.88 Found: C, 63.09; H, 7.99; N, 10.83.

EXAMPLE 41

Boc-Phe-His Amide of (1R,2S,2'S,3'S)-2-Amino-3-cyclohexyl-1-hydroxy-1-[3'-(isopropyl)oxetan-2'-yl]propane Using the procedure or Example 40 with the resultant compound from Example 29 in place of the resultant compound from Example 28 gave the desired product (38%): TLC (15% methanol/85% chloroform) $R_f$=0.52; $^1$H NMR (CDCl$_3$) 8.35–8.00 (br, 1H), 7.53 (s, 1H), 7.38–7.18 (m, 5H), 6.88 (s, 1H), 6.56 (br, d, 1H), 1.48 (s, 9H), 0.88 (d, 3H), 0.83 (d, 3H).

Anal. ($C_{35}H_{53}N_5O_6$) Calcd: C, 65.70; H, 8.35; N, 10.95 Found: C, 65.58; H, 8.73; N, 10.86.

EXAMPLE 42

Boc-Phe-His Amide of (1R,2S,2'S,3'R)-2-Amino-3-cyclohexyl-1-hydroxy-1-[3'-(isopropyl)oxetan-2'-yl]propane Using the procedure of Example 40 with the resultant compound from Example 30 in place of the resultant compound from Example 28 gave the desired product (40%): TLC (15% methanol/85% chloroform) $R_f$=0.55; $^1$H NMR (CDCl$_3$) 8.00–7.75 (br, 1H), 7.53 (s, 1H), 7.38–7.18 (m, 5H), 6.87 (s, 1H), 6.60 (br d, 1H), 5.03 (br d, 1H), 2.18–2.03 (m, 1H), 1.48 (s, 9H), 1.02 (d, 3H), 0.75 (d, 3H).

Anal. ($C_{35}H_{53}N_5O_6$) Calcd: C, 64.79; H, 8.39; N, 10.7 Found: C, 64.95; H, 8.34; N, 10.69.

EXAMPLE 43

Boc-Phe-His Amide of (1R,2S,2'S,3'S)-2-Amino-3-cyclohexyl-1-hydroxy-1-[3'-(propyl)oxetan-2'-yl]propane Using the procedure of Example 40 with the resultant compound from Example 31 in place of the resultant compound from Example 28 gave the desired product (36%): TLC (15% methanol/85% chloroform) $R_f$=0.50; $^1$H NMR (CDCl$_3$) 7.52 (d, 1H), 7.38–7.18 (m, 5H), 6.86 (s, 1H), 6.55 (br d, 1H), 4.98 (br d, 1H), 4.61 (dd, 1H), 1.48 (s, 9H), 0.88 (t, 3H).

Anal. ($C_{35}H_{53}N_5O_6 \cdot H_2O$) Calcd: C, 63.90; H, 8.43; N, 10.65 Found: C, 63.87; H, 8.22; N, 10.68.

EXAMPLE 44

Boc-Phe-His Amide of (1R,2S,2'S,3'S)-2-Amino-3-cyclohexyl-1-hydroxy-1-[3'-(isobutyl)oxetan-2'-yl]propane Using the procedure of Example 40 with the resultant compound from Example 32 in place of the resultant compound from Example 28 gave the desired product (40%): TLC (15% methanol/85% chloroform) $R_f$=0.53; $^1$H NMR (CDCl$_3$) 7.53 (d, 1H), 7.38–7.18 (m, 5H), 6.86 (s, 1H), 6.55 (br d, 1H), 4.97

Anal. ($C_{36}H_5N_5O_6$) Calcd: C, 65.23; H, 8.51; N, 10.56 Found: C, 65.15; H, 8.39; N, 10.42.

EXAMPLE 45

Boc-Phe-His Amide of (1R,2S,2'S)-2-Amino-3-cyclohexyl-1-hydroxy-1-(oxetan-2'-yl)propane Using the procedure of Example 40 with the resultant compound from Example 33 in place of the resultant compound from Example 28 gave the desired product (19%): TLC (15% methanol/85% chloroform) $R_f$=0.39; $^1$H NMR (CDCl$_3$) 8.18–7.97 (br, 1H), 7.55 (d, 1H), 7.37–7.20 (m, 5H), 6.86 (s, 1H), 6.58 (br d, 1H), 5.02 (br d, 1H), 2.78–2.48 (m, 2H), 1.48 (s, 9H).

Anal ($C_{32}H_{47}N_5O_6 \cdot 1.5 H_2O$) Calcd: C, 61.52; H, 8.07; N, 11.2 Found: C, 61.31; H, 7.53; N, 10.84.

EXAMPLE 46

Boc-Phe-His Amide of (1R,2S,2'S,3'S)-2-Amino-3-cyclohexyl-1-hydroxy-1-[3'-(methyl)oxetan-2'-yl]propane Using the procedure of Example 40 with the resultant compound from Example 34 in place of the resultant compound from Example 28 gave the desired product (39%): TLC (15% methanol/85% chloroform) $R_f$=0.38; $^1$H NMR (CDCl$_3$) 7.52 (d, 1H), 7.38–7.18 (m, 5H), 6.85 (s, 1H), 6.53 (br d, 1H), 4.99 (br d, 1H), 4.51 (dd, 1H), 1.48 (s, 9H), 1.23 (d, 3H).

Anal. ($C_{33}H_{49}N_5O_6 \cdot 0.75 H_2O$) Calcd: C, 63.39; H, 8.14; N, 11.20 Found: C, 63.38; H, 8.11; N, 10.79.

EXAMPLE 47

Boc-Phe-His Amide of (1R,2S,2'S,3'S)-2-Amino-3-cyclohexyl-1-hydroxy-1-[3'-(1,1,1-trifluoroisopropyl)oxetan-2'-yl]propane Using the procedure of Example 40 with the resultant compound from Example 35 in place of the resultant compound from Example 28 gave the desired product (63%): m.p. 131°–135° C.; TLC (15% methanol/85% chloroform) $R_f$=0.45; $^1$H NMR (CDCl$_3$) 8.55–8.45 (br, 1H), 7.53 (d, 1H), 7.40–7.18 (m, 5H), 6.88 (s, 1H), 6.51 (br d, 1H), 4.99 (br d, 1H), 1.48 (s, 9H), 1.12 (d, 3H).

Anal. ($C_{35}H_{50}N_5O_6F_3$) Calcd: C, 60.59; H, 7.26; N, 10.0 Found: C, 60.35; H, 7.30; N, 10.06.

EXAMPLE 48

Boc-Phe-His Amide of (1R,2S,2'S)-2-Amino-3-cyclohexyl-1-[3',3'-(dimethyl)oxetan-2'-yl]-1-(hydroxy)propane Using the procedure of Example 40 with the resultant compound from Example 36 in place of the resultant compound from Example 28 gave the desired product (49%): TLC (15% methanol/85% chloroform) $R_f$=0.45; $^1$H NMR (CDCl$_3$) 8.08–7.93 (br, 1H), 7.56 (s, 1H), 7.40–7.15 (m, 5H), 6.87 (s, 1H), 6.62 (br d, 1H), 5.07 (br d, 1H), 1.48 (s, 9H), 1.40 (s, 3H), 1.36 (s, 3H).

Anal. ($C_{34}H_{51}N_5O_6 \cdot 0.5 H_2O$) Calcd: C, 64.33; H, 8.26; N, 11.0 Found: C, 64.62; H, 8.29; N, 10.71.

EXAMPLE 49

(1R,2S,2'S,3'S)-2-[(tert-Butyloxycarbonyl)amino]-3-cyclohexyl-1-3'-(ethyl)oxetan-2'-yl]-1-(hydroxy)propane The resultant compound from Example 28 (0.522 g, 1.37 mmol) was treated with 3:1:1 acetic acid/tetrahydrofuran/water (15 mL) at 45° C. for 27 h. After evaporation of the solvent, the mixture was diluted with ether, washed with saturated NaHCO$_3$ solution, water, and brine, and then was dried over Na$_2$SO$_4$ and evaporated to afford 0 44 g (94%) of a solid: m.p. 82–87° C.; TLC (50% ethyl acetate/50% hexane) $R_f$=0.42; $^1$H NMR (CDCl$_3$) 4.80–4.68 (m, 1H), 4.60 (dd, 1H), 4.39 (dd, 1H), 4.29 (dd, 1H), 3.74–3.61 (m, 2H), 3.01–2.85 (m, 2H), 1.43 (s, 9H), 0.84 (t, 3H).

Anal. ($C_{19}H_{35}NO_4$) Calcd: C, 66.83; H, 10.33; N, 4.10 Found C, 66.84; H, 10.48; N, 4.09.

EXAMPLE 50

(1R,2S,2'S,3'S)-2-Amino-3-cyclohexyl-1-[3'-(ethyl)oxetan-2'-yl]-1-(hydroxy)propane Trifluoroacetic acid (15 mL) was chilled in an ice-water bath and poured into a solution of the resultant compound from Example 49 (0.430 g, 1.26 mmol) in methylene chloride (15 mL) at 0° C. After 1 h at 0° C., the solvent was evaporated and the residue was diluted with water, basified with Na$_2$CO$_3$, and extracted into chloroform which was dried over Na$_2$SO$_4$ and evaporated to afford 0.318 g (100%) of a solid: m.p. 66°–70° C.; TLC (15% methanol/85% chloroform) R$_f$=0.19; $^1$H NMR (CDCl$_3$) 4.52 (dd, 1H), 4.36 (dd, 1H), 4.28 (dd, 1H), 3.44 (dd, 1H), 3.02–2.92 (m, 1H), 2.90–2.73 (m, 1H), 0.87 (t, 3H).

Anal. (C$_{14}$H$_{27}$NO$_2$) Calcd: C, 66.83; H, 10.33; N, 4.10 Found: C, 66.84; H, 10.48; N, 4.09.

EXAMPLE 51

Diethyl (2-Bromoallyl)acetamidomalonate

To a stirred mixture of diethyl acetamidomalonate (217 g, 1.0 mol) and 2,3-dibromopropene (240 g, 1.2 mol) in dry tetrahydrofuran (2.50 L), under nitrogen, was added sodium hydride (26.4 g, 1.1 mol) in several portions. The reaction mixture was stirred at room temperature for 30 min, then heated to reflux. After heating for 18 h, the resultant slurry was cooled to room temperature and suction filtered through a short pad of silica gel. The solid residue was washed with tetrahydrofuran (2×50 mL), and the filtrates were combined and concentrated. The residue was dissolved in ethyl acetate (2.0 L), washed with water and brine, and then was dried over MgSO$_4$. Filtration and concentration gave a yellow oil which solidified upon drying. The resultant solid was recrystallized from a mixture of hot ethyl acetate/hexane to give 301 g (89%) of the desired product: m.p. 85°–87° C.

EXAMPLE 52

Diethyl (3-Bromo-2-oxo-propyl)acetamidomalonate

To a cold (0° C.), stirred solution of the resultant compound from Example 51 (280 g, 0.83 mol) in a mixture of 2:1 acetonitrile/water (1.68 L) was added solid N-bromosuccinimide (193 g, 1.08 mol) in three portions over a period of 15 min. The resultant orange mixture was stirred at 0° C. for an additional period of 1 h and then was allowed to warm to room temperature. After 4 h, the reaction mixture was treated with 10% aqueous sodium thiosulfate, diluted with ethyl acetate, and washed sequentially with water, 10% aqueous NaHSO$_4$ (3×), water, and brine. Drying (MgSO$_4$) and concentration afforded a yellow solid which was recrystallized from a mixture of ethyl acetate and hexane to give 247 g (85%) of the desired compound as a white solid: m.p. 97°–98.5° C.

EXAMPLE 53

Diethyl (4-Thiazolylmethyl)acetamidomalonate

A 5 L, 3-neck round bottom flask equipped with a mechanical stirrer, stopper and a drying tube was charged with the resultant compound from Example 52 (325 g, 0.92 mol) and flushed with nitrogen. A freshly prepared solution of thioformamide in tetrahydrofuran (0.8M, 1.25 L) was added in one portion. The reaction mixture was stirred at room temperature for 4 h. The resultant slurry was then diluted with ether (1.25 L) and cooled to 0° C. The solid was then collected by suction filtration and washed with cold ether (3×) to give the title compound as the hydrobromide salt. This material was transferred to a 4 L separatory funnel, slurried with ethyl acetate (2 L) and basified by the careful addition of 2M NaOH. The organic layer was separated, washed with water and brine, and then dried over MgSO$_4$. Filtration and concentration afforded a pale yellow oil which solidified upon drying to give 242 g of the desired compound. This material was recrystallized from an ethyl acetate/hexane mixture to afford 185.6 g (64%) of pure material: m.p. 104°–106° C.

EXAMPLE 54

N-Acetyl-3-(4-thiazolyl)-DL-alanine Ethyl Ester

To a stirred solution of the resultant compound from Example 53 (185.6 g, 0.59 mol) in a mixture of tetrahydrofuran (620 mL) and ethanol (310 mL) was added aqueous 2M LiOH (325 mL, 0.65 mol) dropwise over 20 min. After stirring at room temperature for 2.5 h, the reaction mixture was concentrated and the resultant aqueous mixture was extracted with ether (3×200 mL), adjusted to pH 3 with 3M HCl, and concentrated under reduced pressure. Residual water was removed by evaporating portions of toluene (2×200 mL). The residue was diluted with toluene (1.5 L) and the resultant slurry was heated to reflux with separation of water (Dean-Stark trap). After 3 h the reaction mixture was cooled to room temperature, diluted with ethyl acetate (1.5 L) and suction filtered through SiO$_2$ (60 g). The solids were washed with additional ethyl acetate (4×500 mL) and the combined organic layers were concentrated to afford a pale yellow oil which solidified on drying (0.5 torr) to afford 119.6 g (84%) of the desired compound: m.p. 58°–62° C.

EXAMPLE 55

N-Acetyl-3-(4-thiazolyl)-L-alanine and N-Acetyl-3-(4-thiazolyl)-D-alanine Ethyl Ester A 5 L, 3-neck round bottom flask equipped with a mechanical stirrer was charged with the resultant compound from Example 54 (210 g, 0.87 mol), distilled water (1.6 L), and 1M aqueous KCl (0.8 L). The homogeneous solution was adjusted to pH 7.0 with 0.1M NaOH and then was treated with Subtilisin Carlsberg (1.8 g) dissolved in 0.1M aqueous KCl (25 mL). The reaction mixture was stirred at room temperature with 1.0M NaOH added as required to maintain the pH at 6.25–7.25. After 4 h, 430 mL of base had been consumed and the reaction was judged to be complete. The reaction mixture was then extracted with chloroform (4×1.5 L), the aqueous phase was carefully acidified to pH 4 with 2M HCL and then was concentrated under reduced pressure. Residual water was removed by consecutive evaporation of portions of toluene (3×500 mL) and ethanol (3×500 mL). The residue was taken up in warm ethanol and suction filtered to remove inorganic salts. The solids were washed with warm ethanol (3×400 mL) and the filtrates were concentrated to afford 92.6 g (50%) of N-acetyl-3-(4-thiazolyl)-L-alanine as a white solid: m.p. 186° C.

The combined chloroform fractions from the extractions were washed with saturated aqueous NaHCO$_3$, water, and brine and then were dried over MgSO$_4$. Filtration and concentration gave 103 g (49%) of N-acetyl-3-(4-thiazolyl)-D-alanine ethyl ester. This material could be further purified by recrystallization from ethyl acetate/hexane: m.p. 79°-80.5° C.

EXAMPLE 56

Epimerization of N-Acetyl-3-(4-thiazolyl)-D-alanine Ethyl Ester

A 2 L round bottom flask equipped with a magnetic stirrer, reflux condenser, and nitrogen inlet was charged with sodium (0.96 g, 0.045 mol) and ethanol (900 mL) and the mixture was allowed to reflux until the sodium was consumed. The resultant solution of sodium ethoxide was cooled slightly, and N-acetyl-3-(4-thiazolyl)-D-alanine ethyl ester from Example 55 (102 g, 0.42 mol) was added. The reaction mixture was then heated to reflux. After 3 h the solution was cooled to room temperature, quenched with glacial acetic acid (0.045 mol) and concentrated to remove ethanol. The residue was diluted with ethyl acetate, washed with water and brine and dried over MgSO$_4$. Filtration and concentration gave a yellow oil which was purified by recrystallizing from a mixture of hot ethyl acetate and hexane to yield 89 g (87%) of material identical to that obtained from Example 54.

EXAMPLE 57

3-(4-Thiazolyl)-L-alanine Dihydrochloride

A 2 L round bottom flask equipped with a magnetic stirrer was charged with N-acetyl-3-(4-thialzoyl)-L-alanine from Example 55 (92.6 g, 0.43 mol) and 6M HCl (1 L). The resultant solution was heated to reflux. After 3 h the mixture was allowed to cool to room temperature. The solution was then concentrated under reduced pressure, evaporated from toluene (3×200 mL), and dried under vacuum overnight to give 120 g of a slightly wet solid. This material was used in the next reaction without further purification.

EXAMPLE 58

N-Boc-3-(4-thiazolyl)-L-alanine

A 4 L Erlenmeyer flask equipped with a mechanical stirrer was charged with the resultant compound from Example 57 (125.9 g) and tetrahydrofuran (1.5 L) and the mixture was adjusted to pH 6.6 with saturated aqueous sodium bicarbonate. The resultant solution was then adjusted to pH 8.9 with 3.0M NaOH and a solution of di-tert-butyldicarbonate (117.8 g, 0.51 mol) in tetrahydrofuran (150 mL) was added. The reaction mixture was vigorously stirred at room temperature for 40 h. The tetrahydrofuran was removed under vacuum, the pH of the residue was adjusted to 2.0 with 3.0M HCl and the mixture was extracted with ethyl acetate (3×300 mL). The combined extracts were dried over MgSO$_4$, filtered, and concentrated to give 150 g of a white solid. Recrystallization from hot 1:1 ethyl acetate/hexane (1.06 L) gave 107.6 g (82 % from the resultant compound of Example 12) of the desired compound m.p. 115° C.; $[\alpha]_D = +129.8$ (c=1.04, CHCl$_3$).

Anal. (C11H16N2O2) Calcd: C, 48.53; H, 5.88; N, 10.29 Found: C, 48.58; H, 5.91; N, 10.17.

EXAMPLE 59

Boc-(4-thiazolyl)alanine Amide of (1R,2S,2'S,3')-2-Amino-3-cyclohexyl-1-[3'-(ethyl)oxetan-2'-yl]-1-(hydroxy)propane To a mixture of the resultant amine from Example 50 (4.2779 g, 17.72 mmol), 1-hydroxybenzotriazole (6.4708 g, 47.89 mmol) and the resultant acid from Example 58 (5.0764 g, 18.64 mmol) in dimethylformamide (40 mL) at −23° C. was added N-methylmorpholine (2.00 mL, 18.2 mmol) and 1-(3-dimethylaminopropyl)-3-ethylcarbodiimide hydrochloride(4.85 mg, 25.3 mmol). After stirring at −23° C. for 2 h and at ambient temperature overnight, the mixture was poured into saturated NaHCO$_3$ solution and extracted into ethyl acetate which was washed with water and brine, and then was dried over Na$_2$SO$_4$ and evaporated. Chromatography of the residue on silica gel with 1.2-1.4% methanol in chloroform afforded 7.34 g (84%) of the desired product: TLC (10% methanol/90% chloroform) R$_f$=0.55 $^1$H-NMR (CDCl$_3$) 8.78 (d, 1H), 7.13 (d, 1H), 6.55 (d, 1H), 6.31 (br d, 1H), 4.56 (dd, 1H), 4.53-4.44 (m, 1H), 4.22 (dd, 1H), 4.05 (dd, 1H), 3.92-3.79 (m, 1H), 3.67-3.60 (m, 1H), 3.45 (dd, 1H), 3.18 (dd, 1H), 2.84-2.72 (m, 1H), 1.47 (s, 9H), 0.85 (t, 3H).

Anal. (C25H41N3O5S) Calcd: C, 60.58; H, 8.34; N, 8.48 Found: C, 60.33; H, 8.33; N, 8.24.

EXAMPLE 60

H-(4-thiazolyl)alanine Amide of (1R,2S,2'S,3'S)-2-Amino-3-cyclohexyl-1-[3'-(ethyl)oxetan-2'-yl]-1-(hydroxy)propane The resultant compound from Example 59 (442.4 mg, 0.893 mmol) in dichloromethane (12.5 mL) at −10° C. was treated with trifluoroacetic acid (12.5 mL), and was stirred at −10° C. for 4.5 h. While cold, the solvent was distilled under reduced pressure and the residue was taken up in water. The mixture was made basic with Na$_2$CO$_3$ and extracted into chloroform which was dried over Na$_2$SO$_4$ and evaporated. Chromatography of the residue on silica gel with 3% methanol in chloroform afforded 292 mg (83%) of the desired product: TLC (10% methanol/90% chloroform) R$_f$=0.28; $^1$H-NMR (CDCl$_3$) 8.78 (d, 1H), 7.70 (d, 1H), 7.12 (d, 1H), 4.59 (dd, 1H), 4.24 (dd, 1H), 4.18 (dd, 1H), 3.92-3.78 (m, 2H), 3.75-3.65 (m, 2H), 3.31 (dd, 1H), 3.18 (dd, 1H), 2.90-2.75 (m, 1H), 0.85 (t, Anal. (C20H33N3O3S) Calcd: C, 60.73; H, 8.41; N, 10.6 Found: C, 60.85; H, 8.42; N, 10.58.

EXAMPLE 61

A mixture of benzaldehyde (82.1 mL, 0.81 mol), methyl acrylate (109.1 mL, 1.211 mol), 1,4-diazabicyclo(2,2,2)octane (13.6 g, 0.12 mol), and acetic acid (1.4 mL, 0.024 mol) was allowed to stir at 35° C. for 60 h, at which point the reaction was determined to have proceeded to 70% completion by $^1$H NMR. Methyl acrylate (20.9 mL, 0.23 mol) was then added and the solution was allowed to react at 35° C. for an additional 48 h. The mixture was diluted with diethyl ether (1.0 L) and was washed with 2×200 mL portions of a pH 7 phosphate buffer. After concentration in vacuo, the remaining mixture was distilled at reduced pressure (12 mm) to afford 6.5 g of unreacted benzaldehyde and 130.0 g (90%) of the desired product as a colorless oil: b.p. 130° C. (12 mm); IR (film) 1718, 1440 cm$^1$; $^1$H NMR (CDCl$_3$) 3.67 (s, 3H), 5.52 (br s, 1H), 5.83-5.85 (m, 1H), 6.29-6.31 (m, 1H), 7.23-7.39 (m, 5H); $^{13}$C NMR (75 MHz, CDCl$_3$) 51.8, 72.9, 125.8, 126.5, 127.7, 128.3, 141.2, 141.9, 166.6.

EXAMPLE 62

(Z)-1-Bromo-2-carbomethoxy-3-phenyl-2-propene

To a 2 L, 3-neck Morton flask (fitted with a thermometer, a mechanical stirrer, and an addition funnel) was added the resultant compound from Example 61 (305.9 g, 1.585 mol) followed by addition of 48% HBr (505 mL, 4.46 mol) in one portion. The flask was immersed in an ice-water bath, at which time concentrated sulfuric acid (460 mL, 8.62 mol) was added dropwise over 90 min and the internal temperature of the reaction mixture was maintained at 23°-27° C. throughout the addition process. After removal of the ice-water bath, the mixture was allowed to stir at ambient temperature overnight. The solution was then transferred to a separatory funnel and the organic layer was allowed to separate from the acid layer. The acids were drained and the organic layer was diluted with 2 L of a 1:1 ethyl acetate/hexane solution, washed with saturated aqueous sodium bicarbonate solution (1 L), dried over sodium sulfate, and concentrated to yield 400 g (99%) of the desired product as a light yellow oil, which was used without any additional purification: b.p. 180° C. (12 mm); IR (film) 1718, 712 cm$^{-1}$; $^1$H NMR (CDCl$_3$) 3.89 (s, 3H), 4.40 (s, 2H), 7.38-7.45 (m, 3H), 7.56-7.60 (m, 2H), 7.83 (s, 1H); $^{13}$C NMR (75 MHz, CDCl$_3$) 26.77, 52.47, 128.63, 128.87, 129.61, 134.20, 142.95, 166.62.

EXAMPLE 63

(Z)-2-Carbomethoxy-3-phenyl-2-propane-1-sulfonic Acid Sodium Salt

To a 12 L, 3-neck round bottom flask fitted with a mechanical stirrer, thermometer and an addition funnel was added the resultant product from Example 62 (400 g, 1.57 mol) and methanol (4 L). The mixture was warmed to 50° C. and a solution of sodium sulfite (199 g, 1.57 mol) dissolved in water (4 L) was added over 75 min while the internal temperature of the flask was maintained at 50° C. After the addition was complete, the clear solution was allowed to stir at 50° C. for an additional 45 min. The reaction mixture in solution was taken to the next step without additional purification. The compound may be isolated by concentration to an amorphous powder, which is contaminated with an equivalent of sodium bromide: IR (KBr) 1711, 1628, 1215 cm$^{-1}$; $^1$H NMR (DMSO D$_6$) 3.70 (s, 3H), 3.77 (s, 2H), 7.33-7.41 (m, 3H), 7.48 (s, 1H), 7.87-7.89 (m, 2H); $^{13}$C NMR (75 MHz, DMSO D$_6$) 49.88, 51.93, 127.36, 128.33, 128.91, 129.82, 134.75, 139.06, 168.60.

EXAMPLE 64

2-Carbomethoxy-3-phenylpropane-1-sulfonic Acid Sodium Salt

To the 8 L of 1:1 methanol/water mixture containing the resultant compound from Example 63 was added 60 g of W-24 Raney nickel. The resulting suspension was pressurized under 50 psi of hydrogen and was allowed to shake on a Parr shaker for 24 h, at which time an additional 20 g of Raney nickel catalyst was added. After 6 h under 50 psi of hydrogen, the catalyst was removed by filtration and the solution was concentrated to dryness. To the dry white solid was added ethyl acetate (6 L) and heptane (4 L) and the solution was vigorously stirred with a mechanical stirrer overnight. The white suspension was removed by filtration yielding 530 g (88%) of the desired product as an amorphous powder that was contaminated with approximately one equivalent of NaBr. The compound was used without any additional purification: IR (KBr) 1740, 1215, 1050 cm$^1$. $^1$H NMR (DMSO D$_6$) 2.48-2.54 (m, 1H), 2.74-2.87 (m, 2H), 2.91-3.04 (m, 2H), 3.48 (s, 3H), 7.12-7.32 (m, 5H); $^{13}$C NMR (75 MHz, D$_2$O/DMSO D$_6$) 38.18, 44.80, 52.67, 52.82, 127.42, 129.13, 129.34, 138.14, 176.84.

EXAMPLE 65

2-Carbomethoxy-3-phenyl-1-propanesulfonyl Chloride

To a 3 L round bottom flask was added the resultant compound from Example 64 (530 g, 1.39 mol) and toluene (520 mL) followed by the addition of PC$_{15}$ (317 g, 1.52 mol). The mixture was warmed to 50° C. with stirring for 45 min. It was then diluted with toluene (1 L) and was filtered through Celite. After concentration in vacuo, 371 g (96%) of the desired product was obtained as a light brown oil: IR (film); 1740, 1380, 1170 cm$^{-1}$; $^1$H NMR (CDCl$_3$); 2.92 (dd, 1H, J=8.1, 14.0), 3.17 (dd, 1H, J =6.6, 14.0), 3.41-3.50 (m, 1H), 3.67 (dd, 1H, J =3.3, 14.3), 3.72 (s, 3H), 4.20 (dd, 1H, J=8.8, 14.3), 7.15-7.18 (m, 2H), 7.25-7.35 (m, 3H); $^{13}$C NMR (75 MHz, CDCl$_3$) 37.26, 42.88, 52.65, 64.89, 127.49, 128.87, 128.92, 135.61, 171.79.

EXAMPLE 66

Methyl 2-Benzyl-3-(1-methyl-piperazin-4-ylsulfonyl)propionated

To a 1 L round bottom flask was added the resultant compound from Example 65 (84.5 g, 0.305 mol) and dichloromethane (305 mL). The mixture was cooled to 0° C. in an ice water bath and a solution of N-methyl piperazine (35.5 mL, 32.0 mmol) dissolved in dichloromethane (305 mL) was added dropwise with vigorous stirring over 90 min. After the addition was completed, the ice-water bath was removed and the mixture was stirred an additional 4 h while warming to ambient temperature. The solution was then poured into a separatory funnel containing 1 L of a 5% aqueous NaOH solution. The layers were partitioned and the organic layer was dried over potassium carbonate. Concentration in vacuo yielded an oil, which was filtered through 200 g of silica gel using 4:1 hexane/ethyl acetate as an eluant. Concentration gave 84.3 g (81%) of the desired product as a yellow oil: IR (film); 1735, 1165, 955 cm$^{-1}$; $^1$H NMR (CDCl$_3$) 2.30 (s, 3H), 2.42 (t, 4H, J=4.8), 2.88 (dd, 1H, J=7.7, 14.0), 2.93 (dd, 1H, J=3.7, 14.0), 3.06 (dd, 1H, J=7.0, 13.6), 3.18-3.27 (m, 5H), 3.43 (dd, 1H, J=8.82, 13.9), 3.67 (s, 3H), 7.14-7.17 (m, 2H), 7.24-7.34 (m, 3H); $^{13}$C NMR (75 MHz, CDCl$_3$) 37.91, 42.22, 45.36, 45.83, 49.61, 52.21, 54.36, 27.06, 128.66, 128.92, 129.06, 136.79, 173.33.

EXAMPLE 67

(2S) 2-Benzyl-3-(1-methyl-piperazin-4-ylsulfonyl)propionic Acid

The resultant racemic ester from Example 66 (135 g, 397 mmol) was suspended in acetone (300 mL) and water (900 mL). While being stirred vigorously at a temperature of 35° C., a crude preparation of Subtilisin Carlsberg (10 mL, Alcalase 2.4 L, Novo Laboratories) was added. Sodium hydroxide solution (6M) was used to maintain the reaction at pH 7.5-8.0. After 3 days, the acetone was removed under reduced pressure and the aqueous phase was extracted with CHCl$_3$ (1 L) to remove the unreacted ester. The aqueous phase was adjusted to pH 7 with 3M HCl and was desalted by eluting through a column of Amberlite XAD-16 (2 kg, prewashed sequentially with water, methanol, and water)

using a water to water/methanol gradient. Evaporation of the solvent afforded 46 g (70%) of a white solid: mp 184.5° C.; TLC (25% ethyl acetate/25% water/25% acetic acid/25% n-butanol) $R_f$=0.43;

Anal. ($C_{15}H_{22}N_2O_4S.0.25 H_2O$) Calcd: C, 54.44; H, 6.85; N, 8.47 Found: C, 54.77; H, 6.53; N, 8.39.

EXAMPLE 68

(2S) 2-Benzyl-3-(1-methyl-piperazin-4-ylsulfonyl)propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and the resultant acid from Example 67 gave, after chromatography on silica gel with 2.5% methanol in chloroform, the desired product (89%) as a solid: m.p. 150°–153° C.; TLC (10% methanol/90% chloroform) $R_f$=0.38; $^1$H-NMR (CDCl$_3$) 8.74 (d, 1H), 7.50 (br d, 1H), 7.38–7.12 (m, 6H), 6.28 (br d, 1H), 4.73–4.53 (m, 2H), 4.22 (dd, 1H), 4.05 (dd, 1H), 3.92–3.77 (m, 2H), 3.67–3.53 (m, 1H), 3.53–3.36 (m, 2H), 2.30 (s, 3H), 0.84 (t, 3H).

Anal. ($C_{35}H_{53}N_5O_6S_2$) Calcd: C, 59.72; H, 7.59; N, 9.95 Found: C, 59.63; H, 7.57; N, 9.77.

EXAMPLE 69

(2R)-2-Benzyl-3-(morpholinocarbonyl)propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(morpholinocarbonyl)propionic acid (Rosenberg et al., EP 307837, 1989) gave, after chromatography on silica gel with 1.5% methanol in chloroform, the desired product as a solid: TLC (10% methanol/90% chloroform) $R_f$=0.53 $^1$H-NMR (CDCl$_3$) 8.77 (d, 1H), 7.91 (br d, 1H), 7.40–7.12 (m, 6H), 6.78 (br d, 1H), 4.77–4.68 (m, 1H), 4.58 (dd, 1H), 4.20 (dd, 1H), 4.06 (dd, 1H), 3.98–3.83 (m, 1H), 0.84 (t, 3H).

Anal. ($C_{35}H_{50}N_4O_6S.0.5 H_2O$) Calcd: C, 63.32; H, 7.74; N, 8.4 Found: C, 63.62; H, 7.78; N, 7.90.

EXAMPLE 70

(2R)-2-Benzyl-3-[(4-methylpiperazin-1-yl)carbonyl]-propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(4-methylpiperazin-1-ylcarbonyl)propionic acid (Rosenberg et al., EP 307837, 1989) gave, after chromatography on silica gel with 2.5% methanol in chloroform, the desired product (81%) as a foam: TLC (10% methanol/90% chloroform) $R_f$=0.35; $^1$H-NMR (CDCl$_3$) 8.76 (d, 1H), 7.94 (br d, 1H), 7.37–7.15 (m, 6H), 6.82 (br d, 1H), 4.77–4.68 (m, 1H), 4.58 (dd, 1H), 4.20 (dd, 1H), 4.07 (dd, 1H), 3.98–3.87 (m, 1H), 2.28 (s, 3H), 0.83 (t, 3H).

Anal. ($C_{36}H_{55}N_5O_5S.0.75 H_2O$) Calcd: C, 63.46; H, 8.06; N, 10.28 Found: C, 63.40; H, 7.85; N, 10.01.

EXAMPLE 71

(2R)-2-Benzyl-3-[(2-pyridin-2-ylethyl)methylaminocarbonyl]propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Examples 59 with the resultant amine from Example 60 and (2R)-2-Benzyl-3-((2-pyridin-2-ylethyl)methylaminocarbonyl)propionic acid (Rosenberg et al., EP 307837, 1989) gave, after chromatography on silica gel with 2% methanol in chloroform, the desired product (78%) as a foam: TLC (10% methanol/90% chloroform) $R_f$=0.41; $^1$H-NMR (CDCl$_3$) 2.86, 2.73 (2s, total 3H).

Anal. ($C_{39}H_{53}N_5O_5S.0.75 H_2O$) Calcd: C, 65.29; H, 7.66; N, 9.76 Found: C, 65.14; H, 7.49; N, 9.50

EXAMPLE 72

(2S)-[(1S)-[(Methoxymethoxy)piperidin-1-yl]carbonyl-2-phenylethoxy]hexanoic Acid Amide of (1R,2S,2'S,3'S)-2-Amino-3-cyclohexyl-1-[3'-(isopropyl)oxetan-2'-yl]-1-(hydroxy)propane Using the coupling procedure of Example 59 with the resultant compound from Example 29, which had been deprotected according to the procedure of Example 40, and (2S)-[(1S)-[(methoxymethoxy)piperidin-1-yl]carbonyl-2-phenylethoxy]hexanoic acid (Fung et al., WO 90/03971, 1990) gave, after chromatography on silica gel with 33% hexane in ethyl acetate, the desired product (54%) as a foam: TLC (100% ethyl acetate) $R_f$=0.31 $^1$H-NMR (CDCl$_3$) 5.80, 5.72 (2d, total 1H), 4.70 (s, 3H), 4.28 (dd, 1H), 4.22 (dd, 1H), 3.38 (s, 3H), 2.60–2.45 (m, 1H).

Anal. ($C_{37}H_{60}N_2O_7.0.1 H_2O$) Calcd: C, 68.72; H, 9.38; N, 4.33 Found: C, 68.47; H, 8.97; N, 4.32.

EXAMPLE 73

Benzyl 2-Benzylacrylate

2-Benzylacrylic acid (2.20 g, 13.6 mmol) in dry ether (40 mL) was treated with dicyclohexylcarbodiimide (2.60 g, 12.6 mmol), benzyl alcohol (1.30 mL, 12.6 mmol) and 4-dimethylaminopyridine (0.310 g, 2.54 mmol). After stirring at room temperature for 44 h, the mixture was filtered and evaporated. Chromatography of the residue on silica with 5% oil: b.p. 150° C. (0.2 mm); TLC (20% ethyl acetate/80% hexane) $R_f$=0.31; $^1$H-NMR (CDCl$_3$) 7.15–7.40 (m, 10H), 6.28 (m, 1H), 5.49 (m, 1H), 5.17 (2H,s), 3.67 (s, 2H).

Anal. ($C_{17}H_{16}O_2.0.15 H_2O$) Calcd: C, 80.07; H, 6.44 Found: C, 80.17; H, 6.47.

EXAMPLE 74

Benzyl (2RS)-2-Benzyl-3-(imidazol-1-yl)propionate

The resultant compound from Example 73 (10.00 g, 36.93 mmol) and imidazole (5.40 g, 79.3 mmol) in acetonitrile (10 mL) were heated at reflux for 44 h. The mixture was evaporated and the residue was chromatographed on silica gel with 2% methanol in chloroform to afford 11.20 g (88%) of the desired product as an oil: TLC (5% methanol/95% chloroform) $R_f$=0.35; $^1$H-NMR (CDCl$_3$) 7.38 (s, 1H), 7.38–7.05 (m, 10H), 7.00 (dd, 1H), 6.80 (dd, 1H), 5.03 (d, 1H), 4.99 (d, 1H), 4.25 (1H), 4.03 (dd, 1H), 3.22–3.09 (m, 1H), 3.02 (dd, 1H), 2.78 (dd, 1H).

EXAMPLE 75

(2RS)-2-Benzyl-3-(imidazol-1-yl)propionic Acid

The resultant compound from Example 74 (11.20 g, 35.0 mmol) and 10% palladium on carbon (3.00 g) in methanol (250 mL) were stirred under a hydrogen atmosphere for 16 h. The mixture was filtered and evaporated to afford 7.90 g (98%) of the desired product as a solid: m.p. 159°–163° C.

Anal.($C_{13}H_{14}N_2O_2.0.5 H_2O$) Calcd: C, 66.51; H, 6.23; N, 11.93. Found: C, 66.81; H, 6.03; N, 11.93.

EXAMPLE 76

(2R)-2-Benzyl-3-(imidazol-1-yl)propionyl-(4-thiazolyl)alanine Amide of (1R,2S,2'S,3'S)-1-Amino-3-cyclohexyl-1-[3'-(ethyl)oxetan-2'-yl]-1-(hydroxy)propane Using the coupling procedure of Example 59 with the resultant amine from Example 60 and the resultant acid from Example 75 gave, after chromatographic separation of the diastereomers on silica gel with 2–3% methanol in chloroform, the (2S)-isomer (53%; TLC (10% methanol/90% chloroform) $R_f=0.37$) followed by the desired (2R)-isomer (33%) as a solid: TLC (10% methanol/90% chloroform) $R_f=0.32$; $^1$H-NMR (CDCl$_3$) 8.68 (d, 1H), 7.47 (s, 1H), 7.38–7.10 (m, 5H), 7.12 (br d, 1H), 6.98 (s, 1H), 6.93 (d, 1H), 6.87 (s, 1H), 6.13 (br d, 1H), 4.63–4.50 (m, 2H), 4.32 (dd, 1H), 4.22 (dd, 1H), 4.03 (dd, 1H), 3.98 (dd, 1H), 3.92–3.77 (m, 1H), 3.59 (dd, 1H), 3.18 (dd, 1H), 3.02 (dd, 1H), 2.98–2.66 (m, 4H), 0.83 (t, 3H).

Anal. ($C_{33}H_{45}N_5O_4S.0.25 H_2O$) Calcd: C, 64.73; H, 7.49; N, 11.44 Found: C, 64.59; H, 7.59; N, 11.16.

EXAMPLE 77

(2S)-[(4-Morpholinyl)carbonyl]oxy-3-phenylpropionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2S)-[(4-morpholinyl)carbonyl]oxy-3-phenylpropionic acid (Rosenberg et al., EP 307837, 1989) gives the desired product.

EXAMPLE 78

(2R)-2-Benzyl-3-(morpholinocarbamoyl)-propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(morpholinocarbamoyl)propionic acid (Rosenberg et al., EP 307837, 1989) gives the desired product.

EXAMPLE 79

(2R)-2-Benzyl-3-(ethoxycarbamoyl)propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(ethoxycarbamoyl)propionic acid (Rosenberg et al., EP 307837, gives the desired product.

EXAMPLE 80

(N-Methyl-2,3-dihydroxypropylamino)carbonyl-(O-methyl)tyrosine-(4-thiazolyl)alanine Amide of (1R,2S,2'S,3'S)-1-Amino-3-cyclohexyl-1-[3'-(ethyl)oxetan-2'-yl]-1-(hydroxy)propane Using the coupling procedure of Example 59 with the resultant amine from Example 60 and (N-methyl-2,3-dihydroxypropylamino)carbonyl-(O-methyl(tyrosine (Rosenberg et al., EP 307837, 1989) gives the desired product.

EXAMPLE 81

[(4-Sulfonylmorpholinyl)carbonyl]-Phe-(4-thiazolyl)alanine Amide of (1R,2S,2'S,3'S)-1-Amino-3-cyclohexyl-1-[3'-(ethyl)oxetan-2'-yl]-1-(hydroxy)propane Using the coupling procedure of Example 59 with the resultant amine from Example 60 and [(4-sulfonylmorpholinyl)carbonyl]-Phe (Rosenberg et al., EP 307837, 1989) gives the desired product.

EXAMPLE 82

Isobutyryl-(O-benzyl)threonine-(4-thiazolyl)alanine Amide of (1R,2S,2'S,3'S)-2-Amino-3cyclohexyl-1-[3'-(ethyl)oxetan-2'-yl]-1-(hydroxy)propane Using the coupling procedure of Example 59 with the resultant amine from Example 60 and isobutyryl-(O-benzyl)threonine (Rosenberg et al., EP 307837, 1989) gives the desired product.

EXAMPLE 83

Phenethylmethylaminocarbonyl-(O-methyl)tyrosine-(4-thiazolyl)alanine amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and phenethylmethylaminocarbonyl-(O-methyl)tyrosine (Rosenberg et al., EP 307837, 1989) gives the desired product.

EXAMPLE 84

(Diisopropylaminocarbonyl)phenylalanine-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (diisopropylaminocarbonyl)phenylalanine (Rosenberg et al., EP 307837, 1989) gives the desired product.

EXAMPLE 85

(2R)-2-Benzyl-3-(methylaminocarbonyl)propionyl-(4-thiazolyl)alanine amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(methylaminocarbonyl)propionic acid (Rosenberg et al., EP 307837, 1989) gives the desired product.

EXAMPLE 86

(3,4-cis-Dihydroxypyrrolidinylcarbonyl)-(O-methyl)-tyrosine-(4-thiazolyl)alanine Amide of (1R,2S,2'S,3'R)-2-Amino-3-cyclohexyl-1-[3'-(ethyl)oxetan-2'-yl]-1-(hydroxy)propane Using the coupling procedure of Example 59 with the resultant amine from Example 60 and (3,4-cis-dihydroxypyrrolidinylcarbonyl)-(O-methyl)tyrosine (Rosenberg et al., EP 307837, 1989) gives the desired product.

EXAMPLE 87

(2R)-2-Benzyl-3-(N-methyl)-N-2-methoxyethoxymethoxyethylaminocarbonyl)propionyl-[4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(N-methyl-N-2-dimethoxymethoxypyrrolidinocarbonyl)propionic acid (Rosenberg et al., EP 307837, 1989) gives the desired product.

EXAMPLE 88

(N-Butyl, 4-methoxy)phenylalanine-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (N-butyl, 4-methoxy)phenylalanine (Rosenberg et al., EP 307837, 1989) gives the desired product.

EXAMPLE 90

(2R,S)-[[4-Morpholinyl)carbonyl]amino-]-3,3-dimethyl-3-phenylpropionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R,S)-[[4-morpholinyl)carbonyl]amino]-3,3-dimethyl-3-phenylpropionic acid (Rosenberg et al., EP 307837, 1989) gives the desired product.

EXAMPLE 91

Boc-(1-Naphthyl)Ala-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and Boc-(naphthyl)Ala-OH gives the desired product.

EXAMPLE 92

Dibenzylacetyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and dibenzylacetic acid gave, after chromatography on silica gel with 1–1.5% methanol in chloroform, the desired product (100%) as a solid: m.p. 125°–130° C.; TLC (5% methanol/95% chloroform) $R_f=0.33$; $^1$H NMR (CDCl$_3$) 8.64 (d, 1H), 7.34–7.07 (m, 5H), 6.95 (br d, 1H), 6.74 (d, 1H), 5.86 (br d, 1H), 4.57 (dd, 1H), 4.51–4.42 (m, 1H), 4.19 (dd, 1H), 3.96 (dd, 1H), 3.84–3.66 (m, 1H), 3.56–3.45 (m, 1H), 3.18–2.58 (br m, 7H), 0.83 (t, 3H).

Anal. (C$_{36}$H$_{47}$N$_3$O$_4$S); Calcd: C, 69.98; H, 7.67; N 6.80; Found: C, 69.76; H, 7.63; N, 6.71.

EXAMPLE 93

Dihydrocinnamoyl-(4-thiazolyl)alanine Amide of (1R,2S,2'S,3'S)-2-Amino-3-cyclohexyl-1-[3'-(ethyl)oxetan-2'-yl]-1-(hydroxy)propane Dihydrocinnamoyl chloride (0.012 mL, 0.081 mmol) was added to a solution of the resultant amine from Example 60 (31 mg, 0.078 mmol) and triethylamine (0.012 mL, 0.086 mmol) in methylene chloride (0.5 mL) at 0° C. After stirring 5 min. at 0° C. and 45 min. at ambient temperature, the mixture was taken up in ethyl acetate and the organic layer was washed with saturated NaHCO$_3$ solution and brine, and then was dried over Na$_2$SO$_4$. Filtration followed by evaporation gave a 43 mg of a foam which was chromatographed through silica gel with 1–1.5% methanol in chloroform gave 42 mg (100 %) of a white solid: m.p. 149°–151° C.; TLC (10% methanol/90% chloroform) $R_f=0.52$; $^1$H NMR (CDCl$_3$) 8.74 (d, 1H), 7.03 (d, 1H), 6.40 (br d, 1H), 4.75–4.65 (m, 1H), 4.59 (dd, 1H), 4.23 (dd, 1H), 4.11 (dd, 1H), 3.99–3.85 (m, 1H), 3.67–3.57 (m, 1H), 3.37 (dd, 1H), 3.17–2.93 (m, 3H), 2.85–2.69 (m, 1H), 2.66–2.53 (m, 2H), 0.85 (t, 3H).

Anal. (C$_{29}$H$_{41}$N$_3$O$_4$S) Calcd: C, 66.00; H, 7.83; N, 7.96 Found: C, 66.35; H, 7.95; N, 7.99.

EXAMPLE 94

(2R,4R,5S)-2-(4-Pentenyl)-4-hydroxy-5-tert-butyloxycarbonylamino-6-phenylhexanoic Acid amide of (1R,2S,2'S,3'S)-2-Amino-3-cyclohexyl-1-[3'-(ethyl)oxetan-2'-yl]-1-(hydroxy)propane Using the procedure of Evans, et al. (J. Org. Chem. 1985, 50, 4615) with the resultant compound of Example 50 and (3R,5R,1'S)-5-(1-(tert-butyloxycarbonylamino)-2-phenylethyl)-3-(4-pentenyl)dihydrofuran-2-(3H)-one (D. J. Kempf, J. Org. Chem. 1986, 5J, 3921) gives the desired

EXAMPLE 95

(2R)-2-Benzyl-3-(4-trifluoroethylpiperazin-1-ylcarbonyl)propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-(4-trifluoroethylpiperazin-1-ylcarbonyl)propionic acid (Rosenberg et al., EP 307837, 1989) gives the desired product.

EXAMPLE 96

(2R)-2-Benzyl-3-(N-pyridin-4-yl)methylaminocarbonyl]propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-[(N-pyridin-4-yl)methylaminocarbonyl]propionic acid (Rosenberg et al., EP 307837, 1989) gives the desired product.

EXAMPLE 97

(2S)-2-(4-Morpholinyl)-3-phenylpropionyl-(4-thiazolyl)alanine Amide of
(1R,2S,2'S,3'S)-2-Amino-3-cyclohexyl-1-3'-(ethyl)oxetan-2'-yl]-1-(hydroxy)propane Using the coupling procedure of Example 59 with the resultant amine from Example 60 and (2S)-2-(4-morpholinyl)-3-phenylpropionic acid (Rosenberg et al., EP 307837, 1989) gives the desired product.

(2R)-2-Benzyl-5-tert-butylsulfonyl-4-oxopentanoyl-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-5-tert-butylsulfonyl-4-oxopentanoic acid (Rosenberg et al., EP 307837, 1989) gives the desired product.

EXAMPLE 99

(2R)-2-Benzyl-5-morpholin-4-yl-4-oxopentanoyl-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-Benzyl-5-morpholin-4-yl-4-oxopentanoic acid (Rosenberg et al., EP 307837, 1989) gives the desired product.

EXAMPLE 100

(2R)-2-Benzyl-3-(N-methoxy-N-methylamino)propionyl-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2RS)-2-benzyl-3-(N-methoxyl-N-methylamino)propionic acid (Rosenberg et al., EP 307837, 1989) gives the desired product after chromatographic isomer separation.

EXAMPLE 101

(2S)-2-Benzyl-3-tert-butylsulfonylpropionyl-Histidine Amide of
(1R,2S,2'S,3'S)-2-Amino-3-cyclohexyl-1-[3'-(ethyl)oxetan-2'-yl]-1-(hydroxy)propane Using the coupling and imidazole deprotection procedures of Example 40 with the resultant amine from Example 50 and (2S)-2-Benzyl-3-tert-butylsulfonylpropionic Acid Amide of (imidazole-Boc)Histidine (Rosenberg et al., EP 307837, 1989) gives the desired product.

EXAMPLE 103

1-Methylisonipecotyl-(O-methyl)tyrosine-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and 1-methylisonipecotyl-(O-methyl)tyrosine (Rosenberg et al., EP 307837, 1989) gives the desired product.

EXAMPLE 103

(2R)-2-Benzyl-3-[(2-morpholin-4-ylethyl)methylaminocarbonyl]propionyl-(4-thiazolyl)alanine Amide of
(1R,2S,2'S,3'S)-2-amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-[(2-morpholin-4-ylethyl)methylaminocarbonyl]propionic acid (Rosenberg et al., EP 307837, 1989) gives the desired product.

EXAMPLE 104

(2R)-2-Benzyl-3-[(2-diethylaminoethyl)methylaminocarbonyl]propionyl-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (2R)-2-benzyl-3-[(2-diethylaminoethyl)methylaminocarbonyl]propionic acid (Rosenberg et al., EP 307837, 1989) gives the desired product.

EXAMPLE 105

4-Aza-(5S)-benzyl-6-tert-butylsulfonyl-3-oxo-(2R,S)-(4-thiazolylmethyl)hexane Carboxamide of
(1R,2S,2'S,3'S)-2-Amino-3-cyclohexyl-1-[3'-(ethyl)oxetan-2'-yl]-1-(hydroxy)propane Ethyl 4-aza-5(S)-benzyl-6-tert-butylsulfonyl-3-oxo-(R,S)-(4-thiazolylmethyl)hexanoate (0.20 g, 0.4 mmol, Rosenberg et al., EP 307837, 1989) and potassium hydroxide (0.024 g, 0.4 mmol) in 2 mL of absolute ethanol is stirred at room temperature under nitrogen atmosphere for 18 h and concentrated. The resulting acid salt, using the procedure of Example 59, is coupled with the resultant amine from Example 60 giving the desired product.

EXAMPLE 106

4-Aza-(5S)-benzyl-6-tert-butylsulfonyl-2-fluoro-3-oxo-(2R,S)-(4-thiazolylmethyl)hexane Carboxamide of
(1R,2S,2'S,3'S)-2-Amino-3-cyclohexyl-1-[3'-(ethyl)oxetan-2'-yl]-1-(hydroxy)propane Ethyl 4-aza-5(S)-benzyl-6-tert-butylsulfonyl-2-fluoro-3-oxo-2(R,S)-(4-thiazolylmethyl)hexanoate (Rosenberg et al., EP 307837, 1989) is hydrolyzed as described in Example 105. The resulting acid salt, using the procedure of Example 59, is coupled with the resultant amine from Example 60 giving the desired product.

EXAMPLE 107

(3S)-Acetoxy-(2R,)-benzyl-3-(morpholinocarbonyl)-propionyl-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (3S)-acetoxy-(2R,S)-benzyl-3-(morpholinocarbonyl)propionic acid (Rosenberg et al., EP 307837, 1989) gives the desired product.

EXAMPLE 108

Boc-(4-thiazolyl)alanine-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and the resultant acid from Example 58 gives the desired product.

EXAMPLE 109

Benzyl (2R)-2-Benzyl-3-[(4-cyclopropylpiperazin-1-yl)carbonyl]propionate

Using the mixed anhydride coupling procedure of Example with 1-cyclopropylpiperazine and benzyl (2R)-3-carboxy-2-benzylpropionate (Rosenberg et al., EP 307837, 1989) gave the desired product. $^1$H NMR (CDCl$_3$) 7.10-7.34 (m, 5H), 5.11 (dd, 2H), 3.51 (m, 2H), 3.31 (m, 3H), 3.04 (dd, 1H), 2.74 (m, 2H), 2.52 (m, 3H), 2.35 (dd, 1H), 0.47 (m, 2H), 0.42 (m, 2H).

EXAMPLE 110

(2R)-2-Benzyl-3-[(4-cyclopropylpiperazin-1-yl)carbonyl]propionic Acid

Using the procedure of Example 39 with the resultant compound from Example 109 gave the desired product.

EXAMPLE 111

(2R)-2-Benzyl-3-[(4-cyclopropylpiperazin-1-yl)carbonyl]propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and the resultant acid from Example 110 gives the desired product.

EXAMPLE 112

1-Benzyloxycarbonyl-3-hydroxyazetidine

1-Diphenylmethyl-4-hydroxyazetidine (1.00 g, 4.18 mmol) and 10% Pd/C in methanol (10 mL) were stirred under a hydrogen atmosphere for 20 h. The mixture was filtered and evaporated, and the residue was dissolved in methylene chloride and cooled to 0° C. After addition of triethylamine (0.64 mL, 4.57 mmol) and benzyl chloroformate (0.60 mL, 4.20 mmol), the mixture was stirred at room temperature for 90 min. The mixture was evaporated, taken up in ethyl acetate, washed with 2M HCl, saturated NaHCO$_3$ solution and brine, and then dried over Na$_2$NO$_4$ and evaporated. Chromatography of the residue on silica gel with 50-60% ethyl acetate in hexane afforded 0.376 g (43%) of a colorless oil. TLC (50% ethyl acetate/50% hexane) R$_f$=0.13; $^1$H NMR (CDCl$_3$) 7.29-7.39 (m, 5H), 5.10 (s, 2H), 4.59-4.70 (m, 1H), 4.26 (dd, 1H), 4.23 (dd, 1H), 3.91 (dd, 1H), 3.88 (dd, 1H), 2.15 (d, 1H).

EXAMPLE 113

3-Acetylmercapto-1-benzyloxycarbonylazetidine

To triphenylphosphine (4.40 g, 16.8 mmol) in tetrahydrofuran (25 mL, THF) at −78° C. was added diethylazodicarboxylate (2.60 mL, 16.5 mmol) in THF (15 mL). After 7 min thiolacetic acid (1.25 mL, 17.5 mmol) in THF (15 mL) was added followed by, after 7 min, the resultant compound from Example 112 (2.789 g, 13.46 mmol). The mixture was stirred at −78° C. for 1 h and at room temperature for 20 h, and was then evaporated and chromatographed on silica gel with 20% ethyl acetate in hexane affording 3.250 g (91%) of a white solid, m.p. 94.5°-95.5 ° C. TLC (20% ethyl acetate/80% hexane) R$_f$=0.17; $^1$H NMR (CDCl$_3$) 7.28-7.41 (m, 5H), 5.09 (s, 2H), 4.48 (d, 1H), 4.44 (d, 1H), 4.15-4.26 (m, 1H), 3.92 (d, 1H), 3.89 (d, 1H) 2.34 (s, 3H).

Anal (C$_{13}$H$_{15}$NO$_3$S) Calcd: C, 58.85; H, 5.70, N, 5.28 Found: C, 58.81; H, 5.70; N, 5.26.

EXAMPLE 114

Methyl 2-Benzyl-3-(1-benzyloxycarbonylazetidin-3-ylmercapto)propionate

A solution of sodium methoxide in methanol (3 mL), prepared with sodium bis(trimethylsilyl)amide (0.75 mL, 0.75 mmol, 1.0M in THF), was added to the resultant compound from Example 113 (205.0 mg, 0.773 mmol) in methanol (3 mL). After 45 min, methyl 2-benzylacrylate (150.0 mg, 0.851 mmol, Rosenberg et al., EP 307837, 1989) in methanol (2 mL) was added. After 45 min the reaction was quenched with 2M HCl (0.38 mL, 0.76 mmol), evaporated, and chromatographed on silica gel with 20% ethyl acetate in hexane, to afford 280.6 mg (91%) of a colorless oil. TLC (20% ethyl acetate/80% hexane) R$_f$=0.13; $^1$H NMR (CDCl$_3$) 7.10-7.40 (m, 10H), 5.08 (s, 2H), 4.21-4.33 (m, 2H), 3.77-3.90 (m, 2H), 3.66 (s, 3H), 3.53-3.63 (m, 1H), 3.00 (dd, 1H), 2.72-2.90 (m, 3H), 2.63 (dd, 1H).

EXAMPLE 115

Methyl 2-Benzyl-3-(1-benzyloxycarbonylazetidin-3-ylsulfonyl)propionate

The resultant compound from Example 114 (276.0 mg, 0.691 mmol) in methanol (6 mL) and water (5 mL) was treated with OXONE (1.27 g, 2.07 mmol). After 14 h the mixture was diluted with methanol, filtered and concentrated to ca. 5 mL. After neutralization with solid K$_2$CO$_3$, the mixture was extracted into ethyl acetate which was washed with saturated NaHCO$_3$ solution, water, and brine, and then was dried over Na$_2$NO$_4$ and evaporated to afford 295.9 mg (99%) of a colorless oil TLC (50% ethyl acetate/50% hexane) R$_f$=0.18; $^1$H NMR (CDCl$_3$) 7.10-7.40 (m, 10H), 5.09 (s, 2H)), 4.22-4.35 (m, 2H), 4.25 (dd, 1H), 4.12 (dd, 1H), 3.80-3.92 (m, 1H), 3.73 (s, 3H), 3.44 (dd, 1H), 3.27-3.38 (m, 1H), 3.14 (dd, 1H), 2.92 (dd, 1H), 2.87 (dd, 1H).

EXAMPLE 116

Methyl 2-Benzyl-3-(1-methylazetidin-3-ylsulfonyl)propionate

The resultant compound from Example 115 (270.8 mg) and 10% Pd/C (150 mg) in methanol (6 mL) was treated with formaldehyde in water (0.25 mL, 37% formalin) and stirred under a hydrogen atmosphere for 3 h. The mixture was filtered and evaporated to afford 194.3 mg (99%) of a colorless oil. TLC (15% CH$_3$OH/85% CHCl$_3$) R$_f$=0.60; $^1$H NMR (CDCl$_3$) 7.12-7.37 (m, 5H), 3.77 (dd, 1H), 3.71 (s, 3H), 3.56 (dd, 1H), 3.38-3.50 (m, 4H), 3.26-3.36 (m, 1H), 3.12 (dd, 1H), 2.96 (dd, 1H), 2.88 (dd, 1H), 2.32 (s, 3H).

EXAMPLE 117

2-Benzyl-3-(1-methylazetidin-3-ylsulfonyl)propionic Acid Hydrochloride

The resultant compound from Example 116 (2.120 g, 6.81 mmol) in 2M HCl was stirred at 75 °C. for 20 h. The mixture was washed with ether, evaporated with water chasers, and lyophilized to afford 2.075 g (91%) of a white foam. TLC (25% ethyl acetate/25% water/25% acetic acid/25% n-butanol) $R_f$=0.50; $^1$H NMR (CD30D) 7.17–7.35 (m, 5H), 3.58–3.68 (m, 2H), 2.95 (s, 3H).

EXAMPLE 118

(2S)-2-Benzyl-3-(1-methylazetidin-3-ylsulfonyl)propionyl-(4-thiazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and the resultant acid from Example 117 gives, after chromatographic diastereomer separation, the desired product.

EXAMPLE 119

4-[(1'R)-tert-Butyloxycarbonyl)phenethylamido]maleic Acid (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and maleic acid, D-phenylalanine tert-butyl ester amide (TenBrink, WO 90/03389, 1990) gives the desired product.

EXAMPLE 120

Phenylacetyl-β-L-aspartic Acid Amide of (1R,2S,2'S,3'S)-2-Amino-3-cyclohexyl-1-[3'-(ethyl)oxetan-2'-yl]-1-(hydroxy)propane Using the coupling procedure of Example 59 with the acid α-benzyl ester (Thaisrivongs, WO 89/04833, 1989), and hydrogenating the resulting compound according to the procedure of Example 39 gives the desired product.

EXAMPLE 121 m-(Phenylthiomethyl)benzoic Acid Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and m-(phenylthiomethyl)benzoic acid (TenBrink, WO 88/01488, 1989) gives the desired product.

EXAMPLE 122

(Z)-2-Phenyl-1-(tert-butyloxycarbonyl)aminocyclopropane-1-carboxylic Acid Amide of (4-thiazolyl)alaninyl-(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (Z)-2-phenyl-1-(tert-butyloxycarbonyl)aminocyclopropane-1-carboxylic acid (Gammill et al., WO 88/07053, 1988) gives the desired product.

EXAMPLE 123

(RS)-3-Benzyl-3-benzyloxycarbonylamino-2-oxo-1-pyrrolidine-(2S)-hexanoic Acid Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and (RS)-3-benzyl-3-benzyloxycarbonylamino-2-oxo-1-pyrrolidine-(2S)-hexanoic acid (Thaisrivongs, WO 87/05909, 1987) gives the desired product.

EXAMPLE 124

Benzimidazole-2-carbonyl-norleucine Amide of(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and benzimidazole-2-carbonyl-norleucine (Hoover et al., U.S. Pat. No. 4,935,405, 1990) gives the desired product.

EXAMPLE 125

Boc-L-phenylalaninyl-DL-α-methyl-β-alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and Boc-L-phenylalaninyl-DL-α-methyl-β-alanine (Hanson et al., U.S. Pat. No. 4,931,429, 1990) gives the desired product.

EXAMPLE 126

2-(Boc-Amino)-2-(naphth-1-ylmethyl)malonic Acid Monomethyl Ester Amide of (4-thiazolyl)alaninyl-(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and 2-(Boc-amino)-2-(naphth-1-ylmethyl)malonic acid monomethyl ester (Hudspeth et al., U.S. Pat. No. 4,895,834, 1990) gives the desired product.

EXAMPLE 127

Boc-(3S)-3-(phenylthio)alanine Amide of (4-thiazolyl)alaninyl-(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and Boc-(RS)-3-(phenylthio)alanine (TenBrink., U.S. Pat. No. 4,894,437, 1990) gives the desired product.

EXAMPLE 128

2-Methylsulphonyl-3-phenylpropionic Acid Amide of (4-thiazolyl)alaninyl-(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and 2-methylsulphonyl-3-phenylpropionic acid dicyclohexylammonium salt (Bühlmayer et. al., U.S. Pat. No. 4,889,869, 1989) gives the desired product.

EXAMPLE 129

(RS)-2-(1-Naphthylmethyl)-5-phenoxyvaleric Acid Amide of (4-thiazolyl)alaninyl-(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (RS)-2-(1-naphthylmethyl)-5-phenoxyvaleric acid (Iizuka et. al., U.S. Pat. No. 4,863,904, 1989) gives the desired product.

EXAMPLE 130

(RS)-1-Ethoxycarbonyl-2-(phenyl)ethylsulfonyl-(4-thiazolyl)alanine Amide of(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and (RS)-1-ethoxycarbonyl-2-(phenyl)ethylsulfonyl chloride (Patchett et. al., U.S. Pat. No. 4,839,357, 1989) gives the desired product.

EXAMPLE 131

Boc-Phe[CH$_2$SO]Phe Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and Boc-Phe[CH$_2$SO]Phe (Hudspeth et al., U.S. Pat. No. 4,743,585, 1988) gives the desired product.

EXAMPLE 132

H-Phe-His Amide of (1R,2S,2'S,3'S)-2-Amino-3-cyclohexyl-1-[3'-(ethyl)oxetan-2'-yl]-1-(hydroxy)propane Using the deprotection procedure from Example 60 with the resultant compound from Example 40 gives the desired product.

EXAMPLE 133

(1,2:5,6-di-O-isopropylidene-α-D-glucofuranosyl-3)-acetyl-Phe-His Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 132 and (1,2:5,6-di-O-isopropylidene-α-D-glucofuranosyl- 3)-acetic acid dicyclohexylammonium salt (Arzneim.-Forsch./Drug Res. 1979, 29, 986; Fuhrer et al., U.S. Pat. No. 4,719,288, 1988) gives the desired product.

EXAMPLE 134

Dimethoxyphosphonyl-Phe-His Amide of(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 132 and dimethoxyphosphonyl chloride gives the desired product.

EXAMPLE 135

L-N-[(2S)-3-[3-O-acetyl-5-deoxy-1,2,-O-isopropylidine-α-D-ribofuranos-5-yl]sulfonyl-2-benzylpropionyl]norleucine Amide of(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and L-N-[(2S)-3-[3-O-acetyl-5-deoxy-1,2,-O-isopropylidine-α-D-ribofuranos-5-yl]sulfonyl-2-benzylpropionyl]norleucine (Morishima et al., EP 377139, 1990) gives the desired product.

EXAMPLE 136

2-[8-Isobutyl-6-phenyl-1,2,4-triazolo[4,3-a]pyrazin-3-yl]-3-(3-pyridyl)propionic acid Amide of(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and 2-[8-isobutyl-6-phenyl-1,2,4-triazolo[4,3-a]pyrazin-3-yl]-3-(3-pyridyl)propionic acid sodium salt (Bradbury et al., EP 369743, 1990) gives the desired product.

EXAMPLE 137

Morpholinosulfonyl-Phe-(2-ethylthio)glycine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and morpholinosulfonyl-Phe-(2-ethylthio)glycine (Himmelsbach et al., EP 343654, 1989) gives the desired product.

EXAMPLE 138

4-(N,N'-di-Boc-guanidino)-piperidinecarbonyl-Phe-(4-thiazolyl)Ala Amide of(1R,2S,2'S,3'S)-2-Amino-3-cyclohexyl-1-[3'-(ethyl)oxetan-2'-yl]-1(hydroxy)propane Using the coupling procedure of Example 59 with the resultant amine from Example 60 and 4-(N,N'-di-Boc-guanidino)-piperidinecarbonyl-Phe (Raddatz et al., EP 337334, 1989) gives the desired product.

EXAMPLE 139

5-Chloroindole-2-carboxylic Acid Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and 5-chloroindole-2-carboxylic acid gives the desired product.

EXAMPLE 140

Boc-(3-benzyloxycarbonylamino)propynyl]alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and Boc-[(3-benzyloxycarbonylamino)propynyl]alanine (Hudspeth et al., EP 275480, 1988) gives the desired product.

EXAMPLE 141

(2S)
2-Benzyl-3-(1-methyl-piperidin-4-ylsulfonyl)propionyl-[(3-benzyloxycarbonylamino)propynyl]alanine Amide of
(1R,2S,2'S,3'S)-2-Amino-3-cyclohexyl-1-[3'-(ethyl)oxetan-2'-yl]-1-(hydroxy)propane The resultant compound from Example 140 was deprotected according to the procedure of Example 60. Using the coupling procedure of Example 59 with the resulting amine and the resultant acid from Example 67 gives the desired product.

EXAMPLE 142

Boc-(2-trimethylsilyl)Ala-(4-thiazolyl)Ala Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and Boc-(2-trimethylsilyl)Ala (Weidmann, DE 3841319, 1989) gives the desired product.

EXAMPLE 143

3-(4-Thiazolyl)-2-[(3R)-benzyl-4-N-p-toluenesulfonyl-2-ketopiperazin-1-yl]propionic Acid Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and 3-(4-thiazolyl)-2-[(3R)-benzyl-4-N-α-toluenesulfonyl-2-keto-piperazin-1-yl)propionic acid (De et al., WO 90/04917, 1990) gives the desired product.

EXAMPLE 144

(2S)-[(3S)-(N-Methylpiperazinsulfonyl)-amino-3-phenylmethyl-2-oxo-1-piperidinyl]-3-(4-thiazolyl)propionic Acid Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and (2S)-[(3S)-(N-methylpiperazinsulfonyl)-amino-3-phenylmethyl-2-oxo-1-piperidinyl]-3-(4-thiazolyl)propionic acid (De et al., WO 90/04917, 1990) gives the desired product.

EXAMPLE 145

2-[1-(Carboxy)-2-(4-thiazolyl)ethyl]-1,2,3,4-tetrahydropyrrolo-]3,4-b]-indol-3-one Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and 2-[1-(carboxy)-2-(4-thiazolyl)ethyl]-1,2,3,4-tetrahydropyrrolo-[3,4-b]-indol-3-one lithium salt (Kempf et al., J. Org. Chem., 1990, 55, 1390) gives the desired product.

EXAMPLE 145

2-[(4-Morpholinocarbonyl)-Z-dehydrophenylalanine-(4-thiazolyl)Ala Amide of
(1R,2S,2'S,3'S)-2-Amino-3-cyclohexyl-1-[3'-(ethyl)oxetan-2'-yl]-1-(hydroxy)propane The resultant amine from Example 60 and (Z)-4-benzylidine-2-(4-morpholinocarbonyl)oxazolin-5-one (Plattner et al., *J. Med. Chem.* 1988, 31, 2277) are reacted in dimethylformamide to give the desired product..

EXAMPLE 147

Benzyl 3-Acetylmercapto-2-benzylpropionate

The resulting compound from Example 73 (7.00 g, 27.7 mmol) in dry ether (10 mL) was treated with thiolacetic acid (3.00 mL, 42.0 mmol) and pyridine (2.30 mL, 28.4 mmol). After 114 h at room temperature the mixture was evaporated and chromatographed on silica gel (500 g) with 5–10% ethyl acetate in hexane to afford 8.34 g (92%) of a mobile oil: TLC (20% ethyl acetate/80% hexane) $R_f=0.40$; $^1$H NMR (CDCl$_3$) 7.05–7.40 (m, 10H), 5.05 (s, 2H), 2.87–3.20 (m, 5H), 2.31 (s, 3H).

Anal. (C$_{19}$H$_{20}$O$_3$S.0.5 H$_2$O) Calcd: C, 67.63; H, 6.27 Found: C, 67.98; H, 6.04.

EXAMPLE 148

2-Benzyloxycarbonyl-3-phenyl-1-propylsuflonyl Chloride

Chlorine was bubbled into a mixture of the resultant compound from Example 147 (8.34 g, 25.4 mmol) in water (250 mL) for 30 min at room temperature followed by nitrogen which was bubbled through the mixture for 15 min. The mixture was extracted with methylene chloride which was dried over MgSO$_4$ and evaporated to afford 8.55 g (95%) of an oil which was used without further purification: $^1$H NMR (CDCl$_3$) 7.05–7.45 (m, 10H), 5.13 (s, 2H), 4.21 (dd, 1H), 3.67 (dd, 1H), 3.46–3.57 (m, 1H), 3.16 (dd, 1H), 2.94 (dd, 1H).

EXAMPLE 149

Benzyl 2-Benzyl-3-[1,1,3,3-tetramethylguanidino)]propionate

The resultant compound from Example 148 (280 mg) in methylene chloride (4 mL) at −23° C. was treated with 1,1,3,3-tetramethylguanidine (0.20 mL, 1.6 mmol). After 20 min at −23° C., the mixture was evaporated, taken up in ethyl acetate, washed with saturated NaHCO$_3$ solution and brine, and was then dried over Na$_2$NO$_4$ and evaporated. Chromatography of the residue on silica gel with 2% methanol in chloroform afforded 271.1 mg (57%) of an oil: TLC (5% methanol/95% chloroform) $R_f=0.52$; $^1$H NMR (CDCl$_3$) 7.38–7.13 (m, 10H), 5.12 (d, 1H), 5.05 (d, 1H), 3.60–3.40 (m, 3H), 3.13 (dd, 1H), 3.08–2.85 (m, 1H), 2.88 (s, 12H).

EXAMPLE 150

2-Benzyl-3-[(1,1,3,3-tetramethylguanidino)sulfonyl]-propionic Acid

The resultant compound from Example 149 (266 mg) and 10% Pd/C (190 mg) in methanol (4 mL) were stirred under a hydrogen atmosphere for 2 h. The mixture was filtered and evaporated to afford 194 mg (92%) of a foam: TLC (25% water/25% ethyl acetate/25% acetic acid/25% n-butanol ) $R_f= 0.58$; $^1$H NMR (CDCl$_3$) 7.33–7.18 (m, 5H), 3.62–3.43 (m, 3H), 325–3.12 (m, 2H), 2.90 (s, 12H).

EXAMPLE 151

(2S)-2-Benzyl-3-[(1,1,3,3-tetramethylguanidino)sulfonyl]propionyl-(4-thiazolyl)alanine Amide of
(1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 60 and the resultant acid from Example 150 gives the desired product after chromatographic diastereomer separation.

EXAMPLE 152

Boc-(nor)Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and Boc-(nor)Leu-OH gave, after chromatography on silica gel with 30% ethyl acetate in hexane, the desired product (87%) as a solid: m.p. 95°–97 °C.; TLC (50% ethyl acetate/50% hexane) $R_f$=0.41; $^1$H NMR (CDCl$_3$) 6.38 (br d, 1H), 4.95–4.83 (m, 1H), 4.59 (dd, 1H), 4.27 (dd, 2H), 4.06–3.87 (m, 2H), 3.77–3.68 (m, 1H), 3.38–3.27 (m, 1H), 2.88–2.73 (m, 1H), 1.46 (s, 9H), 0.86 (t, 3H).

Anal. (C$_{25}$H$_{46}$N$_2$O$_5$) Calcd C, 66.05; H, 10.20; N, 6.16 Found: C, 66.08; H, 10.15; N, 6.11.

EXAMPLE 153

H-(nor)Leucine Amide of (1R,2S,2'S,3'S)-2-Amino-3-cyclohexyl-1-[3'-(ethyl)oxetan-2'-yl]-1-(hydroxy)propane Using the deprotection procedure of Example 60 with the resultant compound from Example 152 gave, after recrystallization from a dichloromethane-hexane mixture, the desired product (40%) as a solid: m.p. 130°–131 °C.; TLC (15% methanol/85% chloroform) $R_f$=0.46; $^1$H NMR (CDCl$_3$) 7.59 (br d, 1H), 4.61 (dd, 1H), 4.27 (dd, 2H), 3.98–3.79 (m, 2H), 3.78–3.67 (m, 1H), 3.42–3.29 (m, 1H), 2.91–2.73 (m, 1H), 0.86 (t,3H).

Anal. (C$_{20}$H$_{38}$N$_2$O$_3$) Calcd: C, 67.76; H, 10.80; N, 7.90 Found: C, 67.73; H, 10.73; N, 7.83.

EXAMPLE 154

(2RS)-2-Benzyl-3-(imidazol-1-yl)propionyl-(nor)Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 153 and the resultant acid from Example 75 gave, after chromatography on silica gel with 1.7% methanol in chloroform, the desired product (87%) as a solid: m.p. 180°–181 °C.; TLC (15% methanol/85% chloroform) $R_f$=0.58; $^1$H NMR (CDCl$_3$) 7.47, 7.39 (2s, total 1H), 7.03, 6.99 (2s, total 1H), 6.92, 6.83 (2s, total 1H), 6.09 (d, 1H), 5.97, 5.83 (2d, total 1H), 4.64–4.54 (m, 1H), 4.42–4.13 (m, 4H), 4.08–3.82 (m, 2H), 3.78–3.68 (m, 1H), 3.06–2.66 (m, 4H).

Anal. (C$_{33}$H$_{50}$N$_4$O$_4$) Calcd: C, 69.93; H, 8.89; N, 9.88 Found: C, 69.65; H, 8.75; N, 9.71.

EXAMPLE 155

(2R)-2-Benzyl-3-(4-methylpiperazin-1-ylcarbonyl)propionyl(nor)Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 153 and (2R)-2-benzyl-3-(4-methylpiperazin-1-ylcarbonyl)propionic acid (Rosenberg et al., EP 307837, 1989) gave, after chromatography on silica gel with 1.8–3% methanol in chloroform, the desired product (90%) as a solid: m.p. 100°–110 °C.; TLC (15% methanol/85% chloroform) $R_f$=0.49; $^1$H NMR (CDCl$_3$) 6.53 (d, 1H), 6.34 (d, 1H), 4.59 (dd, 1H), 4.29–4.12 (m, 3H), 3.97–3.83 (m, 1H), 3.69–3.47 (m, 4H), 3.47–3.26 (m, 2H), 3.16–2.99 (m, 2H), 2.87–2.59 (m, 3H), 2.29 (s, 3H).

Anal. (C$_{36}$H$_{58}$N$_4$O$_5$) Calcd: C, 68.98; H, 9.33; N, 8.94 Found: C, 68.83; H, 8.98; N, 8.59.

EXAMPLE 156

Benzyloxycarbonyl-(1-Imidazolyl)Alanine Methyl Ester

N-Benzyloxycarbonyl-L-serine lactone (1.972 g, 8.91 mmol, Arnold et al., *J. Am. Chem. Soc.*, 1987, 109, 4649) and imidazole (1.25 g, 18.4 mmol) were stirred in acetonitrile (40 mL) for 24 h at room temperature. The mixture was then cooled (0 °C., bath temperature), treated with a solution of diazomethane in ether until the persistence of yellow color, and then purged with a steady stream of nitrogen while allowing the mixture to reach room temperature. The mixture was evaporated to a viscous oil and chromatographed on silica gel eluting with 1.8%–2.0% methanol in chloroform to give 1.475 g (55%) of an orange oil: TLC (15% methanol/85% chloroform) $R_f$=0.49; $^1$H NMR (CDCl$_3$) 7.03 (s, 1H), 6.78 (s, 1H), 5.44 (d, 1H), 5.14 (s, 2H), 4.70–4.59 (m, 1H), 4.49–4.38 (m, 2H), 3.79 (s, 3H).

EXAMPLE 157

Benzyloxycarbonyl-(1-Imidazolyl)Alanine

The methyl ester from Example 156 (283 mg, 0.93 mmol) was dissolved in dioxane (4.8 mL), cooled to 0° C., and then treated with 0.6M aqueous LiOH (2.4 mL, 1.44 mmol). Scraping was necessary to homogenize the frozen dioxane. After stirring 1.5 h at 0° C., the reaction was quenched by adding 2M aqueous HCl (0.72 mL, 1.44 mmol) at 0° C. Subsequent concentration gave 342 mg of a brittle foam which also contained 1.5 equivalents LiCl and was used without further purification: TLC (25% 1-butanol/25% ethyl acetate/25% acetic acid/25% water) $R_f$=0.43; $^1$H NMR (DMSO-D$_6$) 7.73 (d, 3H), 7.63 (s, 1H), 6.88 (s, 1H), 5.00 (s, 1H), 4.48–4.27 (m, 2H), 4.17 (dd, 1H).

EXAMPLE 158

Benzyloxycarbonyl-(1-Imidazolyl)Alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and the resultant acid rom Example 157 gave, after chromatography on silica gel with 1.6–3.0% methanol in chloroform, the desired product as a solid: m.p. 160°–161° C.; TLC (15% methanol/85% chloroform) $R_f$=0.49; $^1$H NMR (CDCl$_3$) 7.44 (s, 1H), 7.03 (s, 1H), 6.93 (s, 1H), 6.53 (d, 1H), .559 (d, 1H) 5.13 (s, 2H), 4.60–4.37 (br, 3H), 4.28–4.14 (m, 3H), 4.12–3.98 (m, 1H), 3.71–3.62 (m, 1H), 2.80–2.63 (m, 1H), 0.85 (t, 3H).

Anal. (C$_{28}$H$_{40}$N$_4$O$_5$) Calcd: C, 65.60; H, 7.86; N, 10.92 Found: C, 65.38; H, 7.77; N, 10.75.

EXAMPLE 159

(1-Imidazolyl)Alanine Amide of (1R,2S,2'S,3'S)-2-Amino-3-cyclohexyl-1-[3'-(ethyl)oxetan-2'-yl]-1-(hydroxy)propane The resultant compound from Example 158 (390 mg, 0.76 mmol) and 10% Pd/C in acetic acid (6 mL) were stirred under a hydrogen atmosphere for 21 h. The mixture was filtered and evaporated, and the residue was dissolved in water which was basified to pH 10–11 with solid Na₂CO₃. The mixture was saturated with NaCl and extracted into chloroform which was dried over Na₂NO₄ and evaporated to afford 107 mg (37%) of a tacky foam: TLC (15% methanol/85% chloroform) R$_f$=0.18; ¹H NMR (CDCl₃) 7.68 (s, 1H), 7.60 (d, 1H), 7.11 (s, 1H), 7.00 (s, 1H), 4.59 (dd, 1H), 4.48–4.15 (br, 4H), 4.07–3.92 (m, 1H), 3.79–3.62 (m, 2H), 2.91–2.70 (m, 1H), 0.86 (t, 3H).

EXAMPLE 160

(2R)-2-Benzyl-3-(4-methylpiperazin-1-ylcarbonyl)propionyl-(1-Imidazolyl)alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 159 and (2R)-2-benzyl-3-(4-methylpiperazin-1-ylcarbonyl)propionic acid (Rosenberg et al., EP 307837, 1989) gave, after chromatography on silica gel with 4.5–6.0% methanol in chloroform, the desired product (59%) as a solid: m.p. 150°–160° C.; TLC (15% methanol/85% chloroform) R$_f$=0.19; ¹H NMR (CDCl₃) 7 58 (s, 1H) 7.02 (s, 1H), 6.96 (s, 1H), 6.64 (d, 1H), 6.60–6.44 (br, 1H), 4.76–4.45 (br, 3H), 2.30 (s, 3H), 0.86 (br t, 3H).

Anal. (C₃₆H₅₄N₆O₅·0.44 H₂O) Calcd: C, 65.98; H, 8.38; N, 12.82 Found: C, 66.36; H, 8.42; N, 12.38.

EXAMPLE 161

Benzyloxycarbonyl-Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and benzyloxycarbonyl-Leucine-OH gave, after chromatography on silica gel with 25% ethyl acetate in hexane, the desired product (80%) as a solid: m.p. 118°–120° C.; TLC (50% ethyl acetate/50% hexane) R$_f$=0.31; ¹H NMR (CDCl₃) 6.33 (d, 2H), 5.18–5.01 (m, 3H), 4.57 (dd, 1H), 4.33–4.21 (m, 2H), 4.20–4.06 (m, 1H), 4.03–3.88 (m, 1H), 3.77–3.65 (m, 1H), 2.87–2.67 (m, 1H), 0.84 (t, 3H).

Anal. (C₂₈H₄₄N₂O₅) Calcd: C, 68.82; H, 9.08; N, 5.7 Found: C, 68.71; H, 8.99; N, 5.67.

EXAMPLE 162

H-Leucine Amide of (1R,2S,2'S,3'S)-2-Amino-3-cyclohexyl-1-[3'-(ethyl)oxetan-2'-yl]-1-(hydroxy)propane Using the deprotection procedure of Example 159 with the resultant compound from Example 161 gave, after recrystallization from a dichloromethane-hexane mixture, the desired product (64%) as a solid: m.p. 108°–110° C.; TLC (15% methanol/85% chloroform) R$_f$=0.48; ¹H NMR (CDCl₃) 7.58 (d, 1H), 4.61 (dd, 1H), 4.26 (ddd, 2H), 3.98–3.78 (br, 2H), 3.77–3.67 (m, 1H), 3.38 (dd, 1H), 2.91–2.76 (m, 1H), 0.96 (dd, 6H), 0.85 (t, 3H).

Anal. (C₂₀H₃₈N₂O₃·0.25 H₂O) Calcd: C, 66.91; H, 10.81; N, 7.80 Found: C, 66.95; H, 10.46; N, 7.69.

EXAMPLE 163

(2R)-2-Benzyl-3-(4-methylpiperazin-1-ylcarbonyl)propionyl-leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 162 and (2R)-2-benzyl-3-(4-methylpiperazin-1-ylcarbonyl)propionic acid (Rosenberg et al., EP 307837, 1989) gave, after chromatography on silica gel with 3% methanol in chloroform, the desired product (96%) as a solid: m.p. 155°–165° C.; TLC (15% methanol/85% chloroform) R$_f$=0.43; ¹H NMR (CDCl₃) 6.60 (d, 1H), 6.30 (d, 1H), 4.59 (dd, 1H), 4.29–4.17 (m, 3H), 3.97–3.83 (m, 1H), 3.18–3.01 (m, 2H), 2.30 (s, 3H).

Anal. (C₃₆H₅₈N₄O₅·0.25 H₂O) Calcd: C, 68.48; H, 9.34; N, 8.87 Found: C, 68.35; H, 9.04; N, 8.70.

EXAMPLE 164

Ethoxycarbonyl-Phe-Leu Amide of (1R,2S,2'S,3'S)-2-Amino-3-cyclohexyl-1-[3'-(ethyl)oxetan-2'-yl]-1-(hydroxy)propane To ethoxycarbonyl-Phe-Leu-OH (41.0 mg, 0.117 mmol) in dichloromethane (1 mL) at −10° C. was added N-methylmorpholine (0.013 mL, 0.12 mmol) followed by isobutyl chloroformate (0.015 mL, 0.11 mmol). After 3 min, the resultant amine from Example 50 (25.4 mg, 0.105 mmol) in dichloromethane (2 mL) was added and the reaction was stirred at −10° C. for 15 min and then at ambient temperature for 2 h. The solvent was evaporated and the residue was taken up in ethyl acetate which was washed with 0.5M H₃P₄O, saturated NaHCO₃ solution, and brine, and then was dried over Na₂NO₄ and evaporated. Chromatography of the residue on silica gel with 50% ethyl acetate in hexane afforded 40.8 mg (68%) of the desired product as a solid: m.p. 158°–159° C.; TLC (5% methanol/95% chloroform) R$_f$=0.41; ¹H NMR (CDCl₃) 7.38–7.17 (m, 5H), 6.50 (br d, 1H), 6.2250 (br d, 1H), 5.0350 (br d, 1H), 4.60 (dd, 1H), 4.45–4.33 (m, 2H), 4.29–4.22 (m, 2H), 4.10 (q, 2H), 4.03–3.91 (m, 1H), 3.76–3.67 (m, 1H), 3.37–3.27 (m, 1H), 3.18–3.02 (m, 2H), 2.87–2.72 (m, 1H), 1.22 (t, 3H), 0.92 (d, 6H), 0.87 (t, 3H).

Anal. (C₃₂H₅₁N₃O₆) Calcd: C, 66.99; H, 8.96; N, 7.32 Found: C, 66.89; H, 8.81; N, 7.26.

EXAMPLE 165

(4S,5R,1'S,2'R)-3-(tert-Butyloxycarbonyl)-5-[2'-tert-butylthiocarbonyl-1'-(hydroxy)butyl]-4-(isobutyl)-2,2-dimethyl)oxazolidine Using the procedure of Example 9 with (4S,5R)-3-(tert-butyloxycarbonyl)-4-(isobutyl)-2,2-(dimethyl)oxazolidine-5-carboxaldehyde (Thaisrivongs et al., *J. Med. Chem.*, 1987, 30, 976) gave, after chromatography on silica gel with 3–5% ethyl acetate in hexane, the desired product (24%) as a solid: m.p. 76°–78° C.; TLC (20% ethyl acetate/80% hexane) R$_f$=0.73; ¹H-NMR (CDCl₃) 4.20–4.05 (m, 1H), 3.70–3.46 (m, 2H), 2.96–2.83 (m, 1H), 1.49 (s, 9H), 1.48 (s, 9H), 1.02 (t, 3H), 1.00–0 87 (m, 6H).

Anal. (C₂₃H₄₃NO₅S) Calcd: C, 61.99; H, 9.72; N, 3.14 Found: C, 62.22; H, 9.50; N, 3.19.

EXAMPLE 166

(4S,5R,1'S,2'S)-3-(tert-Butyloxycarbonyl)-4-(isobutyl)-2,2-(dimethyl)-5-[1'-hydroxy-2'-(hydroxymethyl)butyl]oxazolidine Using the procedure of Example 18 with the resultant compound from Example 165 gave, after chromatography on silica gel with 17% ethyl acetate in hexane, the desired product (65%) as an oil: TLC (20% ethyl acetate/80% hexane) R$_f$=0.20; ¹H-NMR (CDCl₃) 4.22–4.02 (m, 2H), 3.95–3.74 (m, 2H), 3.70–3.58 (m, 1H), 1.52 (s, 6H), 1.49 (s, 9H), 1.01 (t, 3H), 1.02–0.90 (m, 6H).

EXAMPLE 167

(4S,5R,1'S,2'S)-3-(tert-Butyloxycarbonyl)-4-(isobutyl)-2,2-(dimethyl)-5-[1'-hydroxy-2'-[(p-toluenesulfonyloxy)methyl]butyl]oxazolidine Using the procedure of Example 19 with the resultant compound from Example 166 gave the desired product (89%) as an oil: TLC (20% ethyl acetate/80% hexane) $R_f=0.27$; $^1$H-NMR (CDCl$_3$) 7.80 (d, 2H), 7.35 (d, 3H), 2.47 (s, 3H), 1.48 (s, 9H), 1.02-0.84 (m, 9H).

EXAMPLE 168

(4S,5R,2'S,3'S)-3-(tert-Butyloxycarbonyl)-4-(isobutyl)-2,2-(dimethyl)-5-[3'-(ethyl)oxetan-2'-yl]oxazolidine Using the procedure of Example 28 with the resultant compound from Example 167 gave, after chromatography on silica gel with 10% ethyl acetate in hexane, the desired product (73%) as an oil: TLC (20% ethyl acetate/80% hexane) $R_f$ 0.49; $^1$H-NMR (CDCl$_3$) 4.62 (dd, 1H), 4.36-4.28 (m, 1H), 4.26 (dd, 1H), 4.02 (dd, 1H), 3.88-3.73 (br, 1H), 2.73-2.58 (m, 1H), 1.58 (s, 6H), 1.47 (s, 9H), 0.97 (d, 3H), 0.95 (d, 3H, 0.89 (t, 3H).

EXAMPLE 169

(1R,2S,2'S,3'S)-2-[(tert-Butyloxycarbonyl)amino-1-[3'-(ethyl)oxetan-2'-yl]-1-hydroxy-4-(methyl)pentane Using the procedure of Example 49 with the resultant compound from Example 168 gave the desired product as a waxy solid: m.p. 63°-65° C.; TLC (20% ethyl acetate/80% hexane) $R_f$32 0.11; $^1$H-NMR (CDCl$_3$) 4.76 (br d, 1H), 4.60 (dd, 1H), 4.39 dd, 1H), 4.29 (dd, 1H), 3.72-3.58 (m, 2H), 3.00-2.84 (m, 1H), 1.42 (s, 9H), 0.93 (d, 3H), 0.91 (d, 3H), 0.85 (t, 3H).

Anal. (C$_{16}$H$_{31}$NO$_4$) Calcd: C, 63.76; H, 10.37; N, 4.65 Found: C, 64.17; H, 9.95; N, 4.85.

EXAMPLE 170

(1R,2S,2'S,3'S)-2-Amino-1-[3'-(ethyl)oxetan-2'-yl]-1-hydroxy-4-(methyl)pentane

Using the procedure of Example 50 with the resultant compound from Example 169 gave the desired product (100%) as a waxy solid: m.p. 43°-45° C.; $^1$H-NMR (CDCl$_3$) 4.62 (dd, 1H), 4.38 (dd, 1H), 4.28 (dd, 1H), 3.50 (dd, 1H), 3.04-2.94 (m, 1H), 2.88-2.74 (m, 1H), 0.95 (d, 3H), 0.91 (d, 3H), 0.90 (t, 3H).

EXAMPLE 171

Boc-Phe-His Amide of (1R,2S,2'S,3'S)-2-Amino-1-[3'-(ethyl)oxetan-2'-yl]-1-hydroxy-4-(methyl)pentane Using the coupling and imidazole deprotection procedures of Example 40 with the resultant amine from Example 170 gave, after chromatography on silica gel with 3% methanol in chloroform, the desired product (31%) as a solid: TLC (15% methanol/85% chloroform) $R_f=0.43$; $^1$H NMR (CDCl$_3$) 7.78 (s, 1H), 7.38-7.15 (m, 5H), 6.93 (s, 1H), 6.77 (br, 1H), 5.12 (br, 1H), 4.62 (dd, 1H), 1.48 (s, 9H), 0.92-0.75 (m, 9H).

Anal. (C$_{31}$H$_{47}$N$_5$O$_6$.0.5 H$_2$O) Calcd: C, 62.60; H, 8.13; N, 11.78 Found: C, 62.34; H, 7.90; N, 11.62.

EXAMPLE 172

Boc-(2-Troc-amino)thiazol-4-yl]alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and Boc-[(2-Troc-amino)thiazol-4-yl]alanine (Conolly et al. EP 399556, 1990) gives the desired product.

EXAMPLE 173

H-(2-Troc-amino)thiazol-4-yl]alanine Amide of (1R,2S,2'S,3'S)-2-Amino-3-cyclohexyl-1-[3'-(ethyl)oxetan-2'-yl]-1-(hydroxy)propane Using the procedure of Example 60 with the resultant compound from Example 172 gives the desired product.

EXAMPLE 174

(Morpholinosulfonyl)Phe-[(2-Troc-amino)thiazol-4-yl]alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 173 and (morpholinosulfonyl)Phe-OH (Conolly et al. EP 399556, 1990) gives the desired product.

EXAMPLE 175

(Morpholinosulfonyl)Phe-[(2-amino)thiazol-4-yl]alanine Amide of (1R,2S,2'S,3'S)-2-Amino-3-cyclohexyl-1-[3'-(ethyl)oxetan-2'-yl]-1-(hydroxy)propane The resultant compound from Example 174 is reacted with zinc dust and ammonium chloride in a mixture of methanol and tetrahydrofuran to give the desired product.

EXAMPLE 176

Boc-(4-thiazolyl)alanine Amide of (1R,2S,2'S,3'S)-2-Amino-1-[3'-(ethyl)oxetan-2'-yl]-1-(hydroxy)pentane Using the procedure of Example 59 with the resultant amine from Example 170 gave, after chromatography on silica gel with 1.4% methanol in chloroform, the desired product in 78% yield as a solid: m.p. 125°-125.5° C.; TLC (10% methanol/90% chloroform) $R_f=0.62$; $^1$H NMR (CDCl$_3$) 8.78 (d, 1H), 7.12 (d, 1H), 6.53 (d, 1H), 6.34 (d, 1H), 4.56 (dd, 1H), 4.54-4.45 (m, 1H), 4.22 (dd, 1H), 4.08 (dd, 1H), 3.90-3.78 (m, 1H), 3.67-3.58 (m, 1H), 3.54-3.48 (m, 1H), 3.46 (dd, 1H), 3.17 (dd, 1H), 1.47 (s, 9H), 0.97 (d, 3H), 0.92 (d, 3H), 0.91 (t, 3H).

Anal. (C$_{22}$H$_{37}$N$_3$O$_5$S) Calcd: C, 58.00; H, 8.18; N, 9.22 Found: C, 58.28; H, 8.37; N, 8.82.

EXAMPLE 177

H-(4-thiazolyl)alanine Amide of (1R,2S,2'S,3'S)-2-Amino-1-[3'-(ethyl)oxetan-2'-yl]-1-hydroxy-4-(methyl)pentane Using the procedure of Example 60 with the resultant compound from Example 176 gave, after chromatography on silica gel with 3-5% methanol in chloroform, the desired product in 77% yield: TLC (10% methanol/90% chloroform) $R_f=0.16$; $^1$H NMR (CDCl$_3$)

8.77 (d, 1H), 7.69 (d, 1H), 7.12 (d, 1H), 4.60 (dd, 1H), 4.24 (dd, 1H), 4.19 (dd, 1H), 3.88–3.77 (m, 1H), 3.76–3.65 (m, 1H), 3.30 (dd, 1H), 3.20 (dd, 1H), 2.88–2.74 (m, 1H), 0.92–0.80 (m, 9H).

Anal. ($C_{17}H_{29}N_3O_3S$) Calcd: C, 57.44; H, 8.22; N, 11.82 Found: C, 57.53; H, 8.28; N, 11.68.

EXAMPLE 178

(2S) 2-Benzyl-3-(1-methyl-piperazin-4-ylsulfonyl)propionyl-(4-thiazolyl)alanine Amide of (1R,2S,2′S,3′S)-2-Amido-1-[3′-(ethyl)oxetan-2′-yl]-1-hydroxy-4-(methyl)pentane Using the coupling procedure of Example 59 with the resultant amine from Example 177 and the resultant acid from Example 67 gave, after chromatography on silica gel with 3% methanol in chloroform, the desired product (62%) as a solid: m.p. 173°–175° C.; TLC (10% methanol/90% chloroform) $R_f$=0 28; $^1$H-NMR (CDCl$_3$) 8.72 (d, 1H), 7.52 (d, 1H), 7.38–7.15 (m, 6H), 6.23 (d, 1H), 4.70–4.62 (m, 1H), 4.58 (dd, 1H), 4.22 (dd, 1H), 4.09 (dd, 1H), 3.90–3.78 (m, 1H), 3.70–3.54 (m, 2H), 3.50–3.37 (m, 2H), 3.26–3.16 (m, 4H), 2.71–2.59 (m, 1H), 2.48–2.35 (m, 4H), 2.30 (s, 3H), 0.92–0.74 (m, 9H).

Anal. ($C_{32}H_{49}N_5O_6S_2$) Calcd: C, 57 89; H, 7.44; N, 10.55 Found: C, 58.28; H, 7.56; N, 10.22.

EXAMPLE 179

(2R)-2-Benzyl-3-(imidazol-1-yl)propionic Acid Amide of L-Phenylaninol

To a solution of the racemic acid from Example 75 (484 mg, 2.10 mmol), L-phenylalaninol (325 mg, 2.15 mmol), 1-hydroxybenzotriazole (770 mg, 5.70 mmol), and 4-methylmorpholine (0.250 mL, 2.27 mmol) in N,N-dimethylformamide (10 mL) at −23° C. was added 1-(3,3-dimethylaminopropyl)-3-ethylcarbodiimide hydrochloride (575 mg, 3.00 mmol). After stirring for 2 h at −23° C. and then for 18 h at room temperature, the mixture was taken up in saturated NaHCO$_3$ solution and extracted into ethyl acetate The organic extracts were washed with water and brine, and then were dried over Na$_2$NO$_4$ and evaporated to a foam. Chromatography on silica gel with 3–4% methanol in chloroform afforded the desired (2R)-isomer (335 mg, 44%) followed by the (2S)-isomer (292 mg, 38%), both as solids.

(2R)-isomer: m.p. 139°–141° C.; TLC (15% methanol/85% chloroform) $R_f$=0.44; $^1$H NMR (CDCl$_3$) 7.40 (s, 1H), 6.82 (s, 1H), (d, 1H), 4.31 (dd, 1H), 4.06–3.91 (m, 2H), 3.26 (d, 2H), 2.97–2.72 (m, 2H).

Anal. ($C_{22}H_{25}N_3O_2$) Calcd: C, 72 70; H, 6.93; N, 11.5 Found: C, 72.34; H, 6.88; N, 11.46.

[(2S)-isomer: m.p. 116°–118° C.; TLC (15% methanol/85% chloroform) $R_f$=0.37; $^1$H NMR (CDCl$_3$) 7.42 (s, 1H), 6.39 (s, 1H), 5.53 (d, 1H), 4.30 (dd, 1H), 4.10–3.93 (m, 2H), 3.43–3.24 (m, 2H), 2.93 (dd, 1H).

Anal. ($C_{22}H_{25}N_3O_2$) Calcd: C, 72.70; H, 6.93; N, 11.56 Found: C, 72 65; H, 6.93; N, 11.50.

EXAMPLE 180

(2R)-2-Benzyl-3-(imidazol-1-yl)propionic Acid

The (2R)-isomer from example 179 (316 mg, 0.87 mmol) was refluxed in 1:3 (v/v) acetic acid/6N HCl for 4 h. The solution was then concentrated to an oil, taken up in water, and adjusted to pH 11 by dropwise addition of 3M aqueous NaOH. After saturating with NaCl, the aqueous layer was extracted with 85% chloroform/15% isopropanol (total volume=100 mL) to remove the amino alcohol The aqueous layer was then adjusted to pH 6 by dropwise addition of 2M aqueous HCl and the desired product was removed by repeated extractions with 75% chloroform/25% isopropanol (total volume=400 mL). The extracts were dried over Na$_2$NO$_4$, filtered, and evaporated to a solid which was taken up in 94% chloroform/6% methanol, filtered through Celite, and then concentrated giving 153 mg (76%) of a pale-yellow crystalline solid: m.p. 140°–145° C.; TLC (25% 1-butanol/25% ethyl acetate/25% acetic acid/25% water) $R_f$=0.44; $^1$H NMR (DMSO-D6) 7.57 (s, 1H), 6.87 (s, 1H), 4.25–4.01 (m, 2H), 3.20–3.04 (m, 1H), 2.88–2.66 (m, 2H).

Anal. ($C_{13}H_{14}N_2O_2$.0.1 H$_2$O) CalCd: C, 67.28; H, 6.17; N, 12.07 Found: C, 67.27; H. 6.14; N, 12.03.

EXAMPLE 181

(2R)-2-Benzyl-3-(imidazol-1-yl)propionyl-(4-thiazolyl)alanine Amide of (1R,2S,2S′,3′S)-2-Amino-1-(3′-(ethyl)oxetan-2′-yl]-1-hydroxy-4-(methyl)pentane Using the coupling procedure of Example 59 with the resultant amine from Example 177 and the resultant acid from Example 180 gave, after chromatography on silica gel with 3% methanol in chloroform, the desired product (62%) as a glass: TLC (10% methanol/90% chloroform) $R_f$=0.23; $^1$H-NMR (CDCl$_3$) 8.67 (d, 1H), 7.46 (s, 1H), 7.37–7.17 (m, 5H), 7.10 (d, 1H), 6.99 (s, 1H), 6.93 (s, 1H), 6.87 (s, 1H), 6.04 (d, 1H), 4.62–4.50 (m, 1H), 4.32 (dd, 1H), 4.22 (dd, 1H), 4.07 (dd, 1H), 1H), 3.02 (dd, 1H), 3.00–2.67 (m, 4H), 0.92–0.72 (m, 9H).

Anal. ($C_{30}H_{41}N_5O_4S$) Calcd: C, 63.47; H, 7.28; N, 12.34 Found: C, 63.57; H, 7.37; N, 11.99.

EXAMPLE 182

(2R)-2-Benzyl-3-(imidazol-1-yl)propionyl-Leucine Amide of (1R,2S,2′S,3′S)-2-Amino-3-cyclohexyl-1-[3′-(ethyl)oxetan-2′-yl]-1-(hydroxy)propane Using the coupling procedure of Example 59 with the resultant amine from Example 162 and the resultant acid from Example 180 gave, after recrystallizing from dichloromethanehexane (1:3) the desired product (86%) as a white solid: m.p. 219°–220° C.; TLC (15% methanol/85% chloroform) $R_f$=0.52; $^1$H NMR (CDCl$_3$) 7.41 (s, 1H), 7.38–7.12 (m, 5H), 6.98 (s, 1H), 6.83 (s, 1H), 6.12 (br d, 1H), 5.96 (br d, 1H), 4.59 (dd, 1H), 4.36–4.19 (m, 3H), 3.98–3.82 (m, 2H), 3.72 (dd, 1H), 3.05–2.94 (m, 1H), 2.89–2.69 (m, 3H).

Anal. ($C_{33}H_{50}N_4O_4$.0.25 H$_2$) Calcd: C, 69.38; H, 8.91; N, 9.8 Found: C, 69.44; H, 8.95; N, 9.76.

EXAMPLE 183

Dibenzylacetyl-Leucine Amide of (1R,2S,2′S,3′S)-2-Amino-3-cyclohexyl-1-[3′-(ethyl)oxetan-2′-yl]-1-(hydroxy)propane Using the coupling procedure of Example 59 with the resultant amine from Example 162 and dibenzylacetic acid gave, after chromatography on silica gel with 1% methanol in chloroform, the desired product (93%) as a solid: m.p. 216°–218° C.; TLC (5% methanol/95% chloroform) $R_f$=0.49; $^1$H NMR (CDCl$_3$) 7.36–7.08 (m, 10H), 6.08 (br d, 1H), 5.34 (br d, 1H), 4.58 (dd, 1H), 4.30–4.09 (m, 3H), 3.87–3.74 (m, 1H), 3.71–3.63 (m, 1H), 3.20 (d, 1H), 3.04 (dd, 1H), 2.90 (dd, 1H), 2.88–2.72 (m, 3H), 2.71–2.58 (m, 1H), 0.83 (t, 3H).

Anal. (C$_{36}$H$_{52}$N$_2$O$_4$) Calcd: C, 74.96; H, 9.09; N, 4.8 Found: C, 75.31; H, 8.89; N, 4.87.

EXAMPLE 184

Benzyloxycarbonyl-(nor)-Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and benzyloxycarbonyl-(nor)Leu-OH gave, after recrystallization from ethyl acetatehexane (1:3), the desired product (65%) as a solid: m.p. 145°–147° C.; TLC (5% methanol/95% chloroform) R$_f$=0.46; $^1$H NMR (CDCl$_3$) 7.43–7.28 (m, 5H), 6.27 (br d, 1H), 5.27–5.13 (m, 1H), 5.12 (br s, 3H), 4.57 (dd, 1H), 4.32–4.19 (m, 2H), 4.16–4.03 (m, 1H), 4.04–3.90 (m, 1H), 3.77–3.66 (m, 1H), 3.08 (d, 1H), 2.85–2.67 (m, 1H).

Anal. (C$_{28}$H$_{44}$N$_2$O$_5$) Calcd: C, 68.82; H, 9.08; N, 5.73 Found: C, 69.02; H, 9.04; N, 5.77.

EXAMPLE 185

Benzyloxycarbonyl-Alanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 50 and benzyloxycarbonyl-Ala-OH gave, after recrystallization from ethyl acetate-hexane (1:3), the desired product (57%) as a white solid: m.p. 137°–139° C.; TLC (10% methanol/90% chloroform) R$_f$=0.50; $^1$H NMR (CDCl$_3$) 7.43–7.26 (m, 5H), 6.29 (br d, 1H), 5.35–5.22 (m, 1H), 5.12 (br s, 2H), 4.58 (dd, 1H), 4.34–4.12 (m, 3H), 4.05–3.92 (m, 1H), 3.77–3.67 (m, 1H), 3.10–3.00 (m, 1H), 2.88–2.69 (m, 1H), 1.38 (d, 3H), 0.84 (t, 3H).

Anal. (C$_{25}$H$_{38}$N$_2$O$_5$) Calcd: C, 67.24; H, 8.58; N, 6.27 Found: C, 67.44; H, 8.60; N, 6.29.

EXAMPLE 186

Dihydrocinnamoyl-(nor)Leucine Amide of (1R,2S,2'S,3'S)-2-Amino-3-cyclohexyl-1-[3'-(ethyl)oxetan-2'-yl]-1-(hydroxy)propane Dihydrocinnamoyl chloride (0.010 mL, 0.067 mmol) was added to a solution of the resultant amine from Example 153 (20 mg, 0.056 mmol) and triethylamine (0.010 mL, 0.072 mmol) in methylene chloride (0.5 mL) at 0° C. After stirring 5 min. at 0° C. and 40 min. at ambient temperature, the mixture was taken up in ethyl acetate and the organic layer was washed with saturated NaHCO$_3$ solution and brine, and then was dried over Na$_2$NO$_4$. Filtration followed by evaporation gave a white solid which was chromatographed through silica gel with 0.5% methanol in chloroform affording 19 mg (70 %) of a white solid: m.p. 155°–157° C.; TLC (5% methanol/95% chloroform) R$_f$=0.32; $^1$H NMR (CDCl$_3$) 7.34–7.16 (m, 5H), 6.27 (br d, 1H), 5.91 (br d, 1H), 4.59 (dd, 1H), 4.38–4.27 (m, 1H), 4.31–4.20 (2dd, 2H), 4.02–3.89 (m, 1H), 3.77–3.67 (m, 1H), 3.04–2.90 (m, 2H), 2.85–2.70 (m, 1H), 2.62–2.42 (m, 2H), 0.87 (t, 3H), 0.85 (t, 3H).

Anal. (C$_{29}$H$_{46}$N$_2$O$_4$·0.5 H$_2$O) Calcd: C, 70.27; H, 9.56; N, 5.65 Found: C, 70.45; H, 9.25; N, 5.72.

EXAMPLE 187

Benzyloxycarbonyl-(4-thiazolyl)alanine Amide of (1R,2S,2'S,3'S)-2-Amino-3-cyclohexyl-1-[3'-(ethyl)oxetan-2'-yl]-1-(hydroxy)propane Benzyl chloroformate (0.012 mL, 0.084 mmol) was added to a solution of the resultant amine from Example 60 (31 mg, 0.078 mmol) and triethylamine (0.012 mL, 0.086 mmol) in methylene chloride (0.5 ML) at 0° C. After stirring 5 min. at 0° C. and 30 min. at ambient temperature, the mixture was taken up in ethyl acetate and the organic layer was washed with saturated NaHCO$_3$ solution and brine, and then was dried Na$_2$NO$_4$ Filtration followed by evaporation gave 49 mg of a sticky film which was chromatographed through silica gel with 1.5% methanol in chloroform affording 39 mg (94 %) of a white solid: m.p. 127°–129° C.; TLC (10% methanol/90% chloroform) R$_f$=0.52; $^1$H NMR (CDCl$_3$) 8.75 (d, 1H), 7.43–7.30 (m, 5H), 7.15–7.08 (br, 1H), 6.72–6.62 (m, 1H), 6.53 (br d, 1H), 5.22–5.07 (m, 2H), 4.62–4.48 (m, 2H), 4.20 (dd, 1H), 4.14–4.04 (m, 1H), 3.96–3.80 (m, 1H), 3.67–3.58 (m, 1H), 3.47 (dd, 1H), 3.34 (d, 1H), 3.19 (dd, 1H), 2.81–2.64 (m, 1H), 0.84 (t, 3H).

Anal. (C$_{28}$H$_{39}$N$_3$O$_5$S·0.5 H$_2$O) Calcd: C, 62.42; H, 7.48; N, 7.80 Found: C, 62.40; H, 7.12; N, 7.76.

EXAMPLE 188

Dibenzylacetyl-(nor)Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 153 and dibenzylacetic acid gave, after chromatography on silica gel with 0.5–0.7% methanol in chloroform, the desired product (46%) as a solid: m.p. 191°–193° C.; TLC (5% methanol/95% chloroform) R$_f$=0.45; $^1$H NMR (CDCl$_3$) 7.35–7.08 (m, 10H), 6.01 (br d, 1H), 5.51 (br d, 1H), 4.58 (dd, 1H), 4.29–4.06 (m, 3H), 3.88–3.75 (m, 1H), 3.71–3.62 (m, 1H), 3.04 (dd, 1H), 2.97–2.57 (m, 4H), 0.84 (t, 3H), 0.79 (t, 3H).

Anal. (C$_{36}$H$_{52}$N$_2$O$_4$·0.25 H$_2$O) Calcd: C, 74.38; H, 9.10; N, 4.8 Found: C, 74.49; H, 8.96; N, 4.79.

EXAMPLE 189

(2R)-2-Benzyl-3-(imidazol-1-yl)propionyl-(nor)Leucine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 153 and the resultant acid from Example 180 gave, after chromatography on silica gel with 1.7–3% methanol in chloroform, the desired product (89%) as a solid: TLC (15% methanol/85% chloroform) R$_f$=0.58; $^1$H NMR (CDCl$_3$) 7.48 (s, 1H), 7.39–7.12 (m, 5H), 7.00 (s, 1H), 6.85 (s, 1H), 6.20 (br d, 1H), 6.11 (br d, 1H), 4.58 (dd, 1H), 4.39–4.13 (m, 4H), 4.00–3.84 (m, 2H), 3.72 (dd, 1H), 3.01 (dd, 1H), 2.96–2.67 (m, 3H), 0.86 (t, 3H), 0.85 (t, 3H).

EXAMPLE 190

H-Alanine Amide of (1R,2S,2'S,3'S)-2-Amino-3-cyclohexyl-1-[3'-(ethyl)oxetan-2'-yl]-1-(hydroxy)propane The resultant compound from Example 185 (110 mg, 0.25 mmol) and 10% Pd on activated carbon (50 mg) were placed in acetic acid (3 mL) and stirred 3 h over a hydrogen atmosphere. After filtration, followed by evaporation, the concentrate was diluted with water, adjusted to pH 10–11 by addition of Na$_2$CO$_3$, and extracted several times with chloroform. The organic extracts were then dried over Na$_2$NO$_4$, filtered, and evaporated to give 76 mg (97%), of a white solid: m.p. 125°–127° C.; TLC (15% methanol/85%chloroform) R$_f$=0.29; $^1$H NMR (CDCl$_3$) 7.53 (br d, 1H), 4.61 (dd, 1H), 4.27 (dd, 2H), 3.95–3.81 (m, 2H), 3.78–3.68 (m, 1H), 3.48 (q, 1H), 2.92–2.76 (m, 1H), 1.34 (d, 3H), 0.85 (t, 3H); mass spectrum (M+H)$^+$ m/z=313.

Anal. (C$_{17}$H$_{32}$N$_2$O$_3$.0.25 H$_2$O) Calcd: C, 64.42; H, 10.33; N, 8.84 Found: C, 64.64; H, 10.02; N, 8.79.

EXAMPLE 191

(2S) 2-Benzyl-3-(1-methyl-piperazin-4-ylsulfonyl)propionylalanine Amide of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 190 and the resultant acid from Example 67 gave, after chromatography on silica gel with 3% methanol in chloroform, the desired product (73%) as a solid: m.p. 115°–130° C. (broad); TLC (15% methanol/85% chloroform) R$_f$=0.44; $^1$H NMR (CDCl$_3$) 7.43–7.11 (m, 5H), 6.33–6.14 (m, 2H), 4.59 (dd, 1H), 4.37–4.18 (m, 3H), 3.97–3.81 (m, 1H), 3.77–3.65 (m, 1H), 3.52–3.37 (m, 1H), 3.32–3.13 (br, 4H), 3.10–2.93 (m, 2H), 2.93–2.71 (m, 3H), 2.56–2.38 (br, 4H), 2.38–2.26 (br, 3H); mass spectrum (M+H)$^+$ m/z =621;

Anal. (C$_{32}$H$_{52}$N$_4$O$_6$S.0.5 H$_2$O) Calcd: C, 61.12; H, 8.12; N, 8.90 Found: C, 61.12; H, 8.12; N, 8.89.

EXAMPLE 192

(2R)-2-Benzyl-3-(imidazol-1-yl)propionyl-alanine Acid of (1R,2S,2'S,3'S)-2-Amino-3-cyclohexyl-1-[3'-(ethyl)oxetan-2'-yl]-1-(hydroxy)propane Using the coupling procedure of Example 59 with the resultant amine from Example 190 and the resultant acid from Example 180 gave, after chromatography on silica gel with 3-methanol in chloroform, the desired product (68%) as a solid: m.p. 199°–200° C.; TLC (15% methanol/85% chloroform) R$_f$=0.49; $^1$H NMR (CDCl$_3$) 7.44 (s, 1H), 7.41–7.11 (m, 5H), 7.00 (s, 1H), 6.85 (s, 1H), 6.19 (d, 1H), 6.11 (d, 1H), 4.58 (dd, 1H), 4.38–4.16 (m, 4H), 4.04–3.83 (m, 2H), 3.78–3.65 (m, 1H), 3.11–2.93 (m, 1H), 2.89–2.67 (m, 3H), 1.13 (d, 3H), 0.83 (t, 3H); mass spectrum (M+H)$^+$ m/z =525;

Anal. (C$_{30}$H$_{44}$N$_4$O$_4$.0.5 H$_2$O) Calcd: C, 67.51; H, 8.50; N, 10.50 Found: C, 67.81; H, 8.34; N, 10.47.

EXAMPLE 193

(4S,5S,Z)-3-(tert-butyloxycarbonyl)-4-(cyclohexylmethyl)-2,2-(dimethyl)oxazolidine-5-but-1-ene To a suspension of propyltriphenylphosphonium bromide (3.15 g, 8.2 mmol) in dry THF (12 mL) at 0° C. was added a solution of potassium tert-butoxide (1.0M, 8.15 mL, 8.15 mmol) After 5 min the mixture was cooled to −78° C. and (4S,5R)-3-(tert-butyloxycarbonyl)-4-(cyclohexylmethyl)-2,2-(dimethyl)oxazolidine-5-carboxaldehyde (2.21 g, 6.8 mmol, Rosenberg et al., *J. Med. Chem.*, 1990, 33, 1582) in THF (20 mL) was added dropwise via cannula over 15 min. The reaction was stirred 35 min then warmed to 0° C. over 15 min at which point it was partitioned between ether (100 mL) and water (50 mL). The layers were separated and the aqueous portion was extracted with ether (2×50 mL). The combined organics were washed with brine (1×50 mL) and dried (MgSO$_4$). Flash silica gel chromatography (200 g silica, 4% ethyl acetate in hexane) gave 1.99 g (83%): [α]$_D^{24}$=+9.4° (c=2.2, CHCl$_3$); $^1$H NMR (CDCl$_3$) 0.9–1.35 (m, 6H), 1.02 (t,J=7 Hz, 3H), 1.48 (s, 9H), 1.50 (s, 3H), 1.62 (s, 3H), 1.5–1.9 (m, 7H), 2.1–2.2 (m, 2H), 3.70 (br s, 1H), 4.60 (dd,J=3, 9 Hz, 1H), 5.45–5.65 (m, 2H); mass spectrum, m/e (M+NH$_4$)$^+$ 369, (M+H)$^+$ 352; IR (CDCl$_3$) 1780 cm$^{-1}$ Anal. Calcd for C$_{21}$H$_{37}$NO$_3$.0.5 H$_2$O: C, 69.96; H, 10.62; N, 3.88. Found: C, 70.31; H, 10.28; N, 3.92.

EXAMPLE 194

(2S,3S,Z)-2-Amino-1-cyclohexyl-3-(hydroxy)hept-4-ene

A solution of the resultant compound from Example 193 (0.58 g, 1.65 mmol) was stirred at ca. 45° C. in a mixture of acetic acid/water/THF (3:1:1, 17 mL) for 2.5 h. The mixture was then cooled to ambient temperature and concentrated. The residue was taken up in ethyl acetate (20 mL) and washed with saturated NaHCO$_3$ solution (2×10 mL). The aqueous portions were back extracted with ethyl acetate (2×5 mL) and the combined organics were washed with brine (1×10 mL) and dried (Na$_2$SO$_4$). Solvents were removed in vacuo leaving 0.48 g oil which was dissolved in methylene chloride (15 mL), chilled to 0° C. and treated with trifluoroacetic acid (15 mL) for 1 h. Evaporation left an oil which was partitioned between chloroform and water. Saturated sodium carbonate solution was added to pH 10 and the layers were separated. The aqueous portion was extracted with chloroform (3×) and then the combined organics were washed with brine (1×) and dried (Na$_2$SO$_4$). Filtration and solvent removal left the crude amino-alcohol, 0.33 g (95%): [α]$_D^{24}$=+6.7° (c=2.1, CHCl$_3$); $^1$H NMR (CDCl$_3$) 0.7–1.5 (m, 7H), 0.98 (t,J=7 Hz, 3H), 1.6–1.8 (m, 5H), 2.0–2.3 (m, 5H), 2.67 (dd,J=3, 8, 10 Hz, 1H), 4.01 (t,J=8 Hz, 1H), 5.29 (ddt,J=8, 10, 1 Hz, 1H), 5.57 (dt,J=10, 8 Hz, 1H); mass spectrum, m/e (M+H)$^+$ 212, (M+H-H$_2$O)$^+$ 194.

EXAMPLE 195

Ethoxycarbonyl-Phe-Leu amide of (2S,3S,Z)-2-Amino-1-cyclohexyl-3-(hydroxy)hept-4-ene Using the coupling procedure of Example 164 with the resultant amine from Example 194 gave, after chromatography on silica gel with 33% ethyl acetate in hexane, the desired product (95%) as a white solid: [α]$_D^{24}$=−30.5° (c=1.1, CHCl$_3$); $^1$H NMR (CDCl$_3$) 0.8–0.95 (m, 2H), 0.91 (d,J=7 Hz, 6H), 0.98 (t,J=7 Hz, 3H), 1.1–1.3 (m, 3H), 1.22 (t,J=7 Hz, 3H), 1.35–1.85 (m, 11 Hz), 2.0–2.2 (m, 2H), 2.50 (br s, 1H), 3.0–3.2 (m, 2H); 3.85–3.95 (m, 1H), 4.10 (q,J=7 Hz, 2H), 4.3–4.45 (m, 3H), 5.06 (d,J=6 Hz,1H), 5.35 (tt,J=1, 9 Hz, 1H), 5.55 (dt,J=8, 12 Hz, 1H), 6.25–6.4 (m, 2H), 7.2–7.4 (m,5H); mass spectrum, m/e (M+NH$_4$)$^+$ 561, (M+H)$^+$ 544; IR (CDCl$_3$) 3420, 1710, 1665 cm$^1$. Anal. Calcd for C$_{31}$H$_{49}$N$_3$O$_5$: C, 68.48; H, 9.08; N, 7.73. Found: C, 68.46; H, 9.24; N, 7.71.

EXAMPLE 196

Ethoxycarbonyl-Phe-Leu Amide of (2S,3S,4R,5R)-2-Amino-1-cyclohexyl-4,5-epoxy-3-(hydroxy)heptane To a solution of the resultant compound from Example 195 (26.9 mg, 49 mmol) in methylene chloride (0.5 mL) at 0° C. was added anhydrous sodium bicarbonate (15.8 mg, 188 mmol) and m-chloroperoxybenzoic acid (13 mg, 60 mmol). After 5.75 h at 0° C. the excess oxidant was quenched by methyl sulfide (5 drops) and the reaction was warmed to ambient temperature. Following a standard methylene chloride/saturated NaHCO$_3$ solution work up the material was purified by flash silica gel chromatography (5 g silica, 33% ethyl acetate in hexane) to yield 24.8 mg (90%) of a white solid: $^1$H NMR (CDCl$_3$) δ 0.8–1.0 (m, 3H), 0.90 (d,J=7 Hz, 3H), 0.91 (d,J=7 Hz, 3H), 1.09 (t,J=7 Hz, 3H), 1.1–1.3 (m, 6H), 1.25 (t,J=7 Hz, 3H), 1.4–1.85 (m, 9H), 2.60 (br s, 1H), 2.9–3.0 (m, 2H), 3.05–3.15 (m, 2H), 3.45–3.52 (m, 1H), 4.1–4.2 (m, 1H), 4.11 (q,J=7 Hz, 2H), 4.3–4.4 (m, 2H), 5.10 (br s, 1H), 6.23 (d,J=8 Hz, 1H), 6.48 (br s, 1H), 7.2–7.4 (m, 5H); mass spectrum, m/e (M+NH$_4$)+ 577, (M+H)+ 560; exact mass, calcd for C$_{31}$H$_{50}$N$_3$O$_6$= 560.3700; found 560.3687; IR (CDCl$_3$) 3415, 3360, 1705, 1665 cm$^{-1}$ Anal Calcd for C$_{31}$H$_{49}$N$_3$O$_6$:C, 66.52; H, 8.82; N, 7.51. Found: C, 66.56; H, 9.08; N, 8.81.

EXAMPLE 197

(4S,5S,E)-3-(tert-butyloxycarbonyl)-4-(cyclohexylmethyl)-2,2-(dimethyl)oxazolidine-5-but-1-ene To the resultant compound from Example 193 (304 mg, 0.86 mmol) as a solution in thiophenol (0.3 mL) at 120° C. (bath temperature), was added AIBN (60 mg total) in 15 mg portions every hour for 4 h. After cooling and diluting with ethyl acetate, the organic layer was washed twice with 2M NaOH and once with brine, then dried over Na$_2$SO$_4$, filtered, and evaporated giving 471 mg of a yellow oil. Chromatography of the crude residue on silica gel, eluting with 3% ether in hexane followed by 5% ether in hexane, afforded 174 mg (57%) of the desired product as a pale-yellow oil which contained a trace of the corresponding Z-isomer: TLC (5% ether/95% hexane) Rf=0.14; $^1$H NMR (CDCl$_3$) 5.88–5.76 (m, 1H), 5.60–5.48 (m, 1H), 4.22 (dd, 1H), 3.80–3.65 (br, 1H), 2.14–2.01 (m, 2H), 1.60 (s, 3H), 1.48 (s, 9H), 1.01 (t, 3H); mass spectrum (M+H)+ m/z=352.

Anal. (C$_{21}$H$_{37}$NO$_3$) calcd: C, 71.75; H, 10.61; N, 3.98 found: C, 71.63; H, 10.33; N, 3.70.

EXAMPLE 198

(2S,3S,E)-2-(tert-Butyloxycarbonyl)amino-1-cyclohexyl-3-(hydroxy)hept-4-ene

The resultant compound from Example 198 (157 mg, 0.45 mmol), which contained a trace of the corresponding Z-isomer, was treated with 3:1:1 (v/v/v), acetic acid: tetrahydrofuran: water at 45°–50° C. (bath temperature) for 6 h. The solvent was then removed in vacuo with toluene chasers to give 145 mg of a pale yellow oil which was subsequently chromatographed on silica gel, eluting with 15% ether in hexane, affording 104 mg (74%) of the desired product as a colorless oil which was free of the corresponding Z-isomer: TLC (50% ether/50% hexane) Rf=0.31; $^1$H NMR (CDCl$_3$) 5.82–5.68 (m, 1H), 5.54–5.42 (m, 1H), 4.59–4.47 (br, 1H), 3.98 (dd, 1H), 3.72–3.58 (m, 1H), 2.13–2.00 (m, 2H), 1.91–1.79 (m, 2H), 1.45 (s, 9H), 0.99 (t, 3H); mass spectrum ((M+H)+ m/z=312.

EXAMPLE 199

Ethoxycarbonyl-Phe-Leu Amide of (2S,3S,E)-2-Amino-1-cyclohexyl-3-(hydroxy)hept-4-ene To a solution of the resultant mono-protected aminoalcohol from Example 198 (101 mg, 0.29 mmol) in methylene chloride (4 mL) at 0° C. (bath temperature), was added trifluoroacetic acid (4 mL), slowly, over 5 minutes. After stirring the mixture 2 h at 0° C., the solvent was removed, leaving an oily residue, which was diluted with water. After adjusting to pH 11 by careful addition of potassium carbonate, the aqueous layer was extracted several times with methylene chloride. The combined extracts were then dried over Na$_2$SO$_4$, filtered, and evaporated to afford 69 mg (>100%) of the desired aminoalcohol which was coupled to Etoc-PHE-LEU-OH using the coupling procedure from example 50, affording, after chromatography on silica gel with 30% ethyl acetate in hexane, 101 mg of a white foam: TLC (100% ethyl acetate) Rf=0.58; $^1$H NMR (CDCl$_3$) 7.40–7.15 (m, 5H), 6.38–6.17 (br, 1H), 6.22 (d, 1H), 5.81–5.65 (m, 1H), 5.43 (dd, 1H), 5.10–4.96 (br, 1H), 4.45–4.30 (m, 2H), 4.10 (q, 2H), 4.07–3.89 (m, 2H), 3.19–3.00 (m, 2H), 2.13–1.97 (m, 2H), 1.23 (t, 3H), 1.00 (t, 3H), 0.91 (d, 6H); mass spectrum (M+H)+ m/z=544.

Anal. (C$_{21}$H$_{37}$NO$_3$(H$_2$O)$_{0.4}$) calcd: C, 67.58; H, 9.11; N, 7.63 found: C, 67.92; H, 8.99; N, 7.30.

EXAMPLE 200

Ethoxycarbonyl-Phe-Leu Amide of (2S,3S,4R,5S)-2-Amido-1-cyclohexyl-4,5-epoxy-3-(hydroxy)heptane (A) and Ethoxycarbonyl-Phe-Leu Amide of (2S,3S,4S,5R)-2-Amino-1cyclohexyl-4,5-epoxy-3-(hydroxy)heptane (B)

To the resultant allylic alcohol from example 199 (50 mg, 0.092 mmol) and sodium bicarbonate (65 mg, 0.77 mmol) in methylene chloride (2 mL) at 0° C. (bath temperature), was added 50% m-chloroperoxybenzoic acid (34 mg, 0.10 mmol). After stirring 6 h at 0° C., followed by 1 h at room temperature, the solvent was removed and the residue was diluted with ethyl acetate. The organic layer was extracted 3× with 0.5M NaOH and once with brine, then dried over Na$_2$SO$_4$, filtered, and evaporated to give 55 mg of a diastereomeric mixture of epoxides as a white solid. Chromatographic separation on silica, eluting with 30–60% ethyl acetate in hexane afforded two products:

A: 45 mg (87%, white solid): TLC (50% ethyl acetate/50% hexane) Rf=0.21; $^1$H NMR (CDCl$_3$) 7.40–7.16 (m, 5H), 6.53–6.33 (br, 1H), 6.20 (d, 1H), 5.12–4.96 (br, 1H), 4.48–4.29 (m, 2H), 4.20–4.03 (m, 1H), 4.11 (q, 2H), 3.18–3.03 (m, 2H), 2.89–2.77 (m, 2H), 1.23 (t, 3H), 0.99 (t, 3H), 0.91 (dd, 6H); mass spectrum (M+H)+ m/z=560.

B: 5 mg (10%, white solid): TLC (50% ethyl acetate/50% hexane) Rf=0.09; $^1$H NMR (CDCl$_3$) 7.40–7.15 (m, 5H), 6.47–6.28 (br, 1H), 6.13 (br d, 1H), 5.08–4.97 (br, 1H), 4.42–4.28 (m, 2H), 4.11 (q, 2H), 3.20–3.00 (m, 2H), 2.96–2.76 (m, 2H), 1.23 (t, 3H), 0.91 (dd, 6H); mass spectrum ((M+H)+ m/z=560.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, phosphate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid, methanesulfonic acid and citric acid. Other salts include salts with alkali metals or alkaline earth metals, such as sodium, potassium, calcium or magnesium or with organic bases.

The compounds of the present invention can also be used in the form of prodrugs which include esters. Examples of such esters are a hydroxyl-substituted compound of formula (I), (II) or (III) which has been acylated with a blocked or unblocked amino acid residue, a phosphate function, or a hemisuccinate residue. The amino acid esters of particular interest are glycine and lysine; however, other amino acid residues can also be used. These esters serve as prodrugs of the compounds of the present invention and serve to increase the solubility of these substances in the gastrointestinal tract. The prodrugs are metabolically converted in vivo to the parent compound of formula (I), (II) or (III). The preparation of the pro-drug esters is carried out by reacting a hydroxyl-substituted compound of formula (I), (II) or (III) with an activated amino acyl, phosphoryl or hemisuccinyl derivative. The resulting product is then deprotected to provide the desired prodrug ester. Other prodrugs are a hydroxyl-substituted compound of formula (I), (II) or (III) wherein the hydroxyl group is functionalized with a substituent of the formula —CH($R_{71}$)OC(O)$R_{72}$ or —CH($R_{71}$)OC(S)$R_{72}$ wherein $R_{71}$ is loweralkyl, haloalkyl, alkoxy, thioalkoxy or haloalkoxy and $R_{72}$ is hydrogen, loweralkyl, haloalkyl, alkoxycarbonyl, aminocarbonyl, alkylaminocarbonyl or dialkylaminocarbonyl. These prodrugs can be prepared by condensation of the hydroxyl group with an activated aldehyde followed by acylation of the intermediate hemiacetal.

The novel compounds of the present invention possess an excellent degree of activity and specificity in treating hypertension in a human or other mammal. The novel compounds of the present invention are also useful for treating congestive heart failure in a human or other mammal. The present invention also relates to the use of the novel compounds of the invention for treating vascular abnormalities in a human or other mammal, especially those vascular diseases associated with diabetes, such as diabetic nephropathy, diabetic neuropathy and diabetic retinopathy. The compounds of the invention are also useful for the treatment of renal diseases in a human or other mammal, in particular acute and chronic renal failure. The compounds of the invention are also useful for the treatment of psoriasis in a human or other mammal.

The ability of the compounds of the invention to inhibit human renal renin can be demonstrated in vitro by reacting a selected compound at varied concentrations with human renal renin, free from acid proteolytic activity, and with renin substrate (human angiotensinogen) at 37° C. and pH of 6.0. At the end of the incubation, the amount of angiotensin I formed is measured by radioimmunoassay and the molar concentration required to cause 50% inhibition, expressed as the $IC_{50}$ is calculated. When tested in accordance with the foregoing procedure, the compounds of the invention were found to inhibit renin with $IC_{50}$'s as shown in Table I.

TABLE I

| Example | $IC_{50}$ (nM) |
|---|---|
| 40 | 0.47 |
| 41 | 0.61 |
| 43 | 0.38 |
| 44 | 1.1 |
| 45 | 1.2 |
| 46 | 0.51 |
| 47 | 1.2 |
| 48 | 1.0 |
| 68 | .19 |
| 69 | .25 |
| 70 | .20 |
| 71 | .27 |
| 72 | .80 |
| 76 | .28 |
| 154 | .70 |
| 155 | .37 |
| 163 | .51 |
| 164 | .46 |
| 171 | .50 |
| 178 | .38 |
| 181 | 3.7 |
| 182 | .65 |
| 183 | 1.2 |
| 186 | 3.3 |
| 188 | .68 |
| 189 | .46 |
| 191 | .58 |
| 192 | 3.4 |

The results indicate that the compounds of the invention are inhibitors of renin.

Total daily dose of a compound of the invention administered to a human or other mammal in single or divided doses may be in amounts, for example, from 0.001 to 10 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

A typical tablet dosage form comprises the active ingredient (no more than 35% by weight of the tablet, citric acid (5-15% by weight of the tablet), a filler such as microcrystalline cellulose (for example, Avicel® PH101), a disintegrant (8-12% by weight of the tablet, for example, crospovidone) and a lubricant (0.5-1.5% by weight of the tablet, for example, magnesium stearate). A tablet can also comprise one or more surfactants (for example, Tween 80, Brij® 35, Emulphor 719 and the like), with the total amount of surfactants being 2-3% by weight of the tablet.

The tablet dosage form is prepared by blending the active ingredient, 50% of the citric acid and the Avicel®. Ethanol (200 proof) is added and the mixture is granulated. If surfactants are included, they are added as a solution in the ethanol during the granulation step. The granules are dried overnight and screened through a 14 mesh screen. The remaining 50% of the citric acid, the crospovidone and the magnesium stearate are blended with the granules and then compressed into tablets.

A typical capsule dosage form comprises a soft elastic gelatin capsule filled with a solution comprising the active ingredient dissolved in a solvent comprising a mixture of PEG 400 (98% volume/volume) and glycerin (2% volume/volume).

A typical soft elastic gelatin capsule has a composition comprising gelatin NF (38.3% by weight), glycerin (96% active; 29% by weight) and water (32.7%).

The capsule dosage form is prepared by mixing appropriate volumes of PEG 400 and glycerin to give a mixture which is 98% by volume PEG 400 and 2% by volume glycerin. Nitrogen is bubbled through the mixture for several hours. While maintaining the mixture under a nitrogen atmosphere, the mixture is heated to about 40° C. and then the desired amount of the active ingredient is dissolved. The solution of active ingredient is then filled into soft elastic gelatin capsules. The filling operation is conducted under a nitrogen atmosphere.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The present invention also relates to the use of novel compounds, pharmaceutical compositions containing the novel compounds and the use of the compounds and compositions to inhibit renin for treating glaucoma or reducing and/or controlling intraocular pressure. The present invention also relates to the use of novel compounds and pharmaceutical compositions which inhibit renin in combination with a beta-adrenergic antagonist agent or an angiotensin converting enzyme inhibiting compound for treating glaucoma or reducing and/or controlling intraocular pressure.

The present invention also relates to pharmaceutical compositions for treating the increase in intraocular pressure associated with the administration of steroidal antiinflammatory agents comprising novel renin inhibiting compounds in combination with a steroidal antiinflammatory compound in a pharmaceutically acceptable vehicle.

The present invention also relates to a kit comprising in individual containers in a single package a novel renin inhibiting compound in a suitable pharmaceutical vehicle and a steroidal antiinflammatory compound in a suitable pharmaceutical vehicle and/or a beta-adrenergic antagonist agent in a suitable pharmaceutical vehicle or an angiotensin converting enzyme inhibiting compound in a suitable pharmaceutical vehicle.

The compositions of the invention are administered as topical or systemic pharmaceutical compositions when used for treating or reducing and/or controlling intraocular pressure.

These compositions are preferably administered as topical pharmaceutical compositions suitable for ophthalmic administration, in a pharmaceutically acceptable vehicle such as pharmaceutically acceptable sterile aqueous or nonaqueous solutions, suspensions, emulsions, ointments and solid inserts.

Examples of suitable pharmaceutically acceptable vehicles for ophthalmic administration are water, propylene glycol and other pharmaceutically acceptable alcohols, sesame or peanut oil and other pharmaceutically acceptable vegetable oils, petroleum jelly, water soluble ophthalmologically acceptable non-toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar, acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xantham gum; and mixtures of these polymers. Such compositions may also contain adjuvants such as buffering, preserving, wetting, emulsifying, and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from 0.00001 to 1.0 (w/v) percent concentration. More preferably the active compound will be administered as an isotonic aqueous solution of from 0.00001 to 0.1 (w/v) percent concentration.

The term "controlling intraocular pressure" as used herein means the regulation, attenuation and modulation of increased intraocular tension. The term also means that the decrease, in the otherwise elevated intraocular pressure, obtained by the methods and compositions of the invention is maintained for a significant period of time as, for example, between consecutive doses of the composition of the invention.

The novel renin inhibiting compounds of the invention may be the only active ingredient for controlling intraocular pressure in the methods and compositions of the invention or may be used in combination with other ingredients which control intraocular pressure such as beta-adrenergic antagonist compounds.

The term "beta-adrenergic antagonist" as used herein means a compound which by binding to beta-adrenergic plasma membrane receptors reduces or eliminates sympathetic activity or blocks the effects of exogenously adminstered catecholamines or adrenergic drugs. Examples of beta-adrenergic antagonists are atenolol, metopropol, nadolol, propranolol, timolol, labetalol, betaxolol, carteolol and dilevalol and pharmaceutically acceptable salts thereof. Most preferably the beta-adrenergic antagonist is timolol.

Timolol is currently used for treating glaucoma or reducing and/or controlling intraocular pressure, but it has a number of adverse side effects. Accordingly, administration of a composition comprising a combination of a beta-adrenergic antagonist and a novel renin inhibiting compound of the invention could produce a reduction in intraocular pressure equivalent to that produced by a beta-adrenergic antagonist alone, but at a reduced dose level of the beta-adrenergic antagonist. This will result in a reduced level of the beta-adrenergic antagonist related adverse side effects.

The combination composition is administered as a single dosage form containing both the novel renin inhibitor and the beta-adrenergic antagonist. The beta adrenergic antagonist may comprise from 5 mg to about 125 mg of the composition of the invention. The preferred ranges of the components in the composition of the invention in unit dosage form are:
Renin inhibitor: 1 ng to 0.1 mg
Beta-adrenergic antagonist: 5 ug to 125 ug When the beta-adrenergic antagonist and the novel renin inhibitor are administered as separate compositions the present invention relates to a kit comprising in two separate containers a pharmaceutically acceptable beta-adrenergic antagonist composition and a pharmaceutically acceptable novel renin inhibitor composition, in a single package. A preferred kit comprises a beta-adrenergic antagonist composition and a topical novel renin inhibitor composition. A most preferred kit comprises a topical ophthalmological beta-adrenergic antagonist composition and a topical ophthalmological novel renin inhibitor composition.

The novel renin inhibiting compounds of the invention may also be administered in combination with an angiotensin converting enzyme (ACE) inhibiting compound. Examples of angiotensin converting enzyme inhibiting compounds are captopril and enalapril. As was previously mentioned, ACE inhibitors have some undesirable side effects. Accordingly, administration of an ACE inhibitor in combination with a renin inhibitor could produce a reduction in intraocular pressure greater than or equivalent to that of an ACE inhibitor alone, but at a reduced dose level of the ACE inhibitor. This will result in a reduced level of the ACE inhibitor related adverse side effects.

The combination composition is administered as a single dose form containing both the novel renin inhibitor and the angiotensin converting enzyme inhibitor. The ACE inhibitor may comprise from 5 ng to about 50 ug of the compositon of the invention. The preferred ranges of the components in the composition of the invention in unit dosage form are:
Renin inhibitor: 1 ng to 0.1 mg
ACE inhibitor: 5 ng to 50 ug When the ACE inhibitor and the novel renin inhibitor are administered as separate compositions the present invention relates to a kit comprising in two separate containers a pharmaceutically acceptable ACE inhibitor composition and a pharmaceutically acceptable novel renin inhibitor composition, in a single package. A preferred kit comprises an ACE inhibitor composition and a topical novel renin inhibitor composition. A most preferred kit comprises a topical ophthalmological ACE inhibitor composition and a topical novel renin inhibitor composition.

Dosage levels of the active compounds in the compositions of the invention may be varied so as to obtain a desired therapeutic response depending on the route of administration, severity of the disease and the response of the patient.

Topical, ophthalmic and systemic administration of steroidal antiinflammatory agents can cause an increase in intraocular pressure. The increase in intraocular pressure can be reduced by the administration of a novel renin inhibiting compound of the invention. Steroidal antiinflammatory agents include hydrocortisone, cortisone, prednisone, prednisolone, dexamethasone, methylprednisolone, triamcinolone, betamethasone, alclometasone, flunisolide, beclomethasone, clorocortolone, diflorasone, halcinonide, fluocinonide, fluocinolone, desoximetasone, medrysone, paramethasone, and fluorometholone, and their pharmaceutically acceptable salts and esters. Preferred steroidal antiinflammatory agents are hydrocortisone, prednisolone, dexamethasone, medrysone and fluorometholone and their pharmaceutically acceptable salts and esters. The novel renin inhibitor is administered after use of a steroidal antiinflammatory agent or at the same time, causing reduction and/or control of intraocular pressure.

Various combinations of a topical or oral or injectible dosage form of a steroidal antiinflammatory agent and a topical or oral dosage form of the novel renin inhibitor may be used. A preferred combination comprises a topical steroidal antiinflammatory and a topical novel renin inhibitor. More preferred is a topical ophthalmic dosage form comprising both a steroidal antiinflammatory and a novel renin inhibitor.

When the steroidal antiinflammatory agent and the novel renin inhibitor are administered as separate compositions the present invention relates to a kit comprising in two separate containers a pharmaceutically acceptable steroidal antiinflammatory agent composition and a pharmaceutically acceptable novel renin inhibitor composition, in a single package. A preferred kit comprises a steroidal antiinflammatory composition and a topical novel renin inhibitor composition. A most preferred kit comprises a topical ophthamological steroidal antiinflammatory composition and a topical ophthamological novel renin inhibitor composition.

The combination composition of the invention may contain from about 0.00001 to 1.0 (w/v) percent of the novel renin inhibitor for combined or separate topical administration. More preferably the amount of the novel renin inhibitor is about 0.00001 to 0.1 (w/v) percent of the composition. The amount of the novel renin inhibitor in a unit dosage form for topical administration to the eye is from about 5 ng to about 0.5 mg, preferably from about 5 ng to about 25 ng. The dose required will depend on the potency of the particular novel renin inhibitor, the severity of the intraocular pressure increase and the response of the individual patient.

The combination composition of the invention may contain from about 0.05 to 1.5 (w/v) percent of the steroidal antiinflammatory for combined or separate topical administration. The amount of the steroidal antiinflammatory in a unit dosage form for topical administration to the eye is from about 20 ug to about 600 ug. The dose required will depend on the potency of the particular steroidal antiinflammatory, the severity of the disease and the response of the individual patient.

When the steroidal antiinflammatory agent of the combination therapeutic method of the invention is administered other than ophthalmically, appropriate doses are well known in the art.

The compositions of the invention may include other therapeutic agents in addition to the novel renin inhibitor, and other agents which reduce and/or control intraocular pressure.

The effect on intraocular pressure of the novel compounds of the invention can be determined in rabbits by using the following method.

Effects of Topically Administered Renin Inhibiting Compounds on Intraocular Pressure of Rabbits a. Method The antiglaucoma activity of the compound was tested by measuring the effect on intraocular pressure in rabbits as described by Tinjum, A. M., Acta Ophthalmologica, 50, 677 (1972). Male albino, New Zealand rabbits were placed in restraining devices and the intraocular pressure was measured with an applamatic tonometer. Exactly 0.1 ml of an isotonic saline solution containing a test compound was instilled into the conjuctival sac and the intraocular pressure was measured at 5, 15, 30, 60, 90, 120 and 180 minutes afterwards.

The ability of a compound of the invention to treat vascular diseases, especially those associated with diabetes, can be demonstrated by comparing urinary protein excretion in control diabetic Wistar rats with urinary protein excretion in diabetic Wistar rats treated with a compound of the invention. Wistar rats are made diabetic by streptozocin treatment.

The ability of a compound of the invention to treat psoriasis can be demonstrated using the methods outlined in Hofbauer, et al., Br. J. Dermatol. 118 85 (1988); Lowe, et al., Arch. Dermatol. 117 394 (1981); and Du Vivier, et al., J. Invest. Dermatol. 65 235 (1975).

The effect of a compound of the invention on renal failure can be demonstrated by observing the effects on renal henodynamics that ultimately can alter glomerular filtration rate (GFR) when a compound of the invention is administered to an animal in which acute renal failure has been modeled. Acute renal failure can be modeled by ischemia, ureteral obstruction or nephrotoxic agents such as gentamicin, cis-platin and the like. In addition, the effect of a compound of the invention on chronic renal failure can be demonstrated by observing the effects on proteinuria, hitopathologic improvement and long term stabilization of GFR when a compound of the invention has been administered to an animal in which chronic renal failure has been modeled. Chronic renal failure can be modeled by reduced renal mass, puromycin-induced nephrosis or diabetic nephropathy.

The present invention is also directed to the use of a compound of the formula (I), (II) or (III) in combination with one or more cardiovascular agents independently selected from diuretics, adrenergic blocking agents, vasodilators, calcium channel blockers, angiotensin converting enzyme (ACE) inhibitors, potassium channel activators, antiserotoninergic agents, thromboxane synthetase inhibitors, angiotensin II (AII) antagonists and other agents useful for treating (in a human or other mammal) hypertension, congestive heart failure, vascular diseases related to diabetes or for treating renal diseases such as acute or chronic renal failure.

Representative diuretics include hydrochlorothiazide, chlorothiazide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, nadolol, propranolol, timolol, carteolol and the like or a pharmaceutically acceptable salt thereof.

Representative vasodilators include hydralazine, minoxidil, diazoxide, nitroprusside, flosequinan and the like or a pharmaceutically acceptable salt thereof.

Representative calcium channel blockers include amrinone, bencyclane, diltiazem, fendiline, flunarizine, nicardipine, nimodipine, perhexilene, verapamil, gallopamil, nifedipine and the like or a pharmaceutically acceptable salt thereof.

Representative ACE inhibitors include captopril, enalapril, lisinopril and the like or a pharmaceutically acceptable salt thereof.

Representative potassium channel activators include pinacidil and the like or a pharmaceutically acceptable salt thereof.

Representative antiserotoninergic agents include ketanserin and the like or a pharmaceutically acceptable salt thereof.

Representative angiotensin II antagonists include DUP527 and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

The compound of formula (I), (II) or (III) and the cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

In addition, the present invention is directed to the use of a compound of formula (I), (II) or (III) to inhibit retroviral proteases and in particular to inhibit HIV-1 protease and HIV-2 protease. Compounds of formula (I), (II) or (III) are useful for treatment or prophylaxis (in a human or other mammal) of diseases caused by retroviruses, especially acquired immune deficiency syndrome or an HIV infection.

The inhibitory potency of the compound of the invention against HIV protease can be determined by the following method.

Fluorogenic Assay for Screening Inhibitors of HIV Protease

A compound of the invention is dissolved in DMSO and a small aliquot further diluted with DMSO to 100 times the final concentration desired for testing. The reaction is carried out in a 6×50 mm tube in a total volume of 300 microliters. The final concentrations of the components in the reaction buffer are: 125 mM sodium acetate, 1M sodium chloride, 5 mM dithiothreitol, 0.5 mg/ml bovine serum albumin, 1.3 uM fluorogenic substrate, 2% (v/v) dimethylsulfoxide, pH 4.5. After addition of inhibitor, the reaction mixture is placed in the fluorometer cell holder and incubated at 30° C. for several minutes. The reaction is initiated by the addition of a small aliquot of cold HIV protease. The fluorescence intensity (excitation 340 nM, emmission 490 nM) is recorded as a function of time. The reaction rate is determined for the first six to eight minutes. The observed rate is directly proportional to the moles of substrate cleaved per unit time. The percent inhibition is 100×(1−(rate in presence of inhibitor)/(rate in absence of inhibitor)).

Fluorogenic substrate: Dabcyl-Ser-Gln-Asp-Tyr-Pro-Ile-Val-Gln-EDANS wherein DABCYL =4-(4-dimethylaminophenyl)azobenzoic acid and EDANS=5-((2-aminoethyl)amino)-naphthalene-1-sulfonic acid.

The antiviral activity of compound of the invention can be demonstrated using the following method.

A mixture of 0.1 ml (4×10$^6$ cells/ml) of H9 cells and 0.1 ml (100 infectious units) of HIV-1$_{3B}$ is incubated on a shaker for 2 h. The resulting culture is washed three times, resuspended into 2 ml of medium, and treated with 10 μl of the compound of the invention (5 mM in dimethylsulfoxide). The control culture is treated in an identical manner except the last step was omitted. After incubation of the culture for eight days without change of medium, an aliquot (0.1 ml) of the supernatent is withdrawn and incubated with fresh H9 cells on a shaker for 2 h. The resulting culture is washed three times, resuspended into 2 ml of medium, and incubated. Virus infectivity is determined using the Abbott HTLV-III antigen E.I.A. method (Paul, et al., J. Med. Virol., 22 357 (1987)).

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

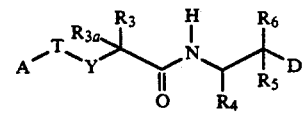

wherein A is
 (1) hydrogen,
 (2) loweralkyl,
 (3) aryl,
 (4) arylalkyl,
 (5) heterocyclic,
 (6) (heterocyclic)alkyl,
 (7) —OR$_{10}$ or —SR$_{10}$ wherein R$_{10}$ is hydrogen, loweralkyl or aminoalkyl,
 (8) —NR$_{11}$R$_{12}$ wherein R$_{11}$ and R$_{12}$ are independently selected from hydrogen, loweralkyl, aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkylamino)alkoxycarbonylalkyl, ((N-protected)alkylamino)alkoxycarbonylalkyl and (dialkylamino)alkoxycarbonylalkyl,
 (9) (alkoxy)(alkyl)aminoalkyl,
 (10) (alkoxy)aminoalkyl,
 (11) (alkoxyalkoxy)aminoalkyl,
 (12) (alkoxyalkoxy)(alkyl)aminoalkyl or
 (13) R$_{13}$—Q—B— wherein
  B is
   (i) —N(R$_{19}$)— wherein R$_{19}$ is hydrogen or loweralkyl,
   (ii) —NHCH$_2$—,
   (iii) —S—,
   (iv) —O—,
   (v) —(CH$_2$)$_b$— wherein b is 0–4 or
   (vi) —CH(OR$_{20}$)— wherein R$_{20}$ is hydrogen, loweralkyl or —C(O)R$_{21}$ wherein R$_{21}$ is loweralkyl or haloalkyl,
  Q is
   (i) —C(O)—,
   (ii) —S(O)—, (iii) —S(O)$_2$—OR,
(iv) —CH(OR$_{14}$)— wherein R$_{14}$ is hydrogen, loweralkyl or —C(O)R$_{15}$ wherein R$_{15}$ is loweralkyl or haloalkyl and R$_{13}$ is
(i) loweralkyl,
(ii) cycloalkyl,
(iii) cycloalkylalkyl,
(iv) cycloalkenyl,
(v) cycloalkenyalkyl,
(vi) amino,
(vii) di-(alkoxyalkyl)amino,
(viii) di-(alkoxyalkoxyalkyl)amino,
(ix) di-(hydroxyalkyl)amino,
(x) aminoalkyl,
(xi) (N-protected)aminoalkyl,
(xii) (N-protected)(alkyl)aminoalkyl,
(xiii) aryl,
(xiv) arylalkyl,
(xv) heterocyclic,
(xvi) (heterocyclic)alkyl,
(xvii) carboxyalkyl,
(xviii) (amino)carboxyalkyl,
(xix) ((N-protected)amino)carboxyalkyl,
(xx) (alkylamino)carboxyalkyl,
(xxi) ((N-protected)(alkyl)amino)carboxyalkyl,
(xxii) (dialkylamino)carboxyalkyl,
(xxiii) alkoxycarbonylalkyl,
(xxiv) (amino)alkoxycarbonylalkyl,
(xxv) ((N-protected)amino)alkoxycarbonylalkyl,
(xxvi) (alkylamino)alkoxycarbonylalkyl,
(xxvii) (((N-protected)(alkyl)amino)alkoxycarbonylalkyl,
(xxviii) (dialkylamino)alkoxycarbonylalkyl,
(xxix) —N=C(NR$_a$R$_b$)$_2$ wherein at each occurrence R$_a$ and R$_b$ are independently selected from loweralkyl or
(xxx) R$_{16}$—G—R$_{17}$— wherein R$_{16}$ is
  (a) loweralkyl,
  (b) loweralkenyl,
  (c) cycloalkyl
  (d) cycloalkenyl,
  (e) cycloalkylalkyl,
  (f) cycloalkenyalkyl,
  (g) hydroxyalkyl,
  (h) dihydroxyalkyl,
  (i) alkoxyalkyl,
  (j) alkoxyalkoxyalkyl,
  (k) polyalkoxyalkyl,
  (l) aryl,
  (m) arylalkyl,
  (n) heterocyclic,
  (o) (heterocyclic)alkyl,
  (p) carboxyalkyl,
  (q) (amino)carboxyalkyl,
  (r) ((N-protected)amino)carboxyalkyl,
  (s) (alkylamino)carboxyalkyl,
  (t) ((N-protected)alkylamino)carboxyalkyl,
  (u) (dialkylamino)carboxyalkyl,
  (v) alkoxycarbonylalkyl
  (w) (amino)alkoxycarbonylalkyl,
  (x) ((N-protected)amino)alkoxycarbonylalkyl,
  (y) (alkylamino)alkoxycarbonylalkyl,
  (z) ((N-protected)alkylamino)alkoxycarbonylalkyl,
  (aa) (dialkylamino)alkoxycarbonylalkyl,
  (bb) alkylsulfonyl,
  (cc) alkylsulfonylalkyl,
  (dd) arylsulfonyl,
  (ee) arylsulfonylalkyl,
  (ff) (heterocyclic)sulfonyl,
  (gg) (heterocyclic)sulfonylalkyl,
  (hh) aminoalkyl,
  (ii) (N-protected)aminoalkyl,
  (jj) alkylaminoalkyl,
  (kk) (N-protected)(alkyl)aminoalkyl or
  (ll) dialkylaminoalkyl,
R$_{17}$ is absent or alkylene and
G is —S—, —S(O)—, —S(O)$_2$—, —O— or —N(R$_{22}$)— wherein
R$_{22}$ is hydrogen or loweralkyl;

T is —CH(R$_1$)— or —C(=CHR$_{1a}$)— wherein
R$_1$ is
  (1) loweralkyl,
  (2) loweralkenyl,
  (3) cycloalkylalkyl,
  (4) cycloalkenylalkyl,
  (5) alkoxyalkyl,
  (6) thioalkoxyalkyl,
  (7) arylalkyl,
  (8) (heterocyclic)alkyl,
  (9) aryloxyalkyl,
  (10) thioaryloxyalkyl,
  (11) arylaminoalkyl,
  (12) aryloxy,
  (13) thioaryloxy,
  (14) arylalkoxyalkyl,
  (15) arylthioalkoxyalkyl or
  (16) arylamino; and
R$_{1a}$ is aryl or arylalkyl;

Y is
  (1) —CH$_2$—,
  (2) —CH(OH)—,
  (3) —C(O)—,
  (4) —NH—,
  (5) —O—,
  (6) —S—,
  (7) —S(O)—,
  (8) —S(O)$_2$—,
  (9) —N(O)—,
  (10) —P(O)O— or
  (11) —W—U— wherein
    W is —C(O)— or —CH(OH)— and
    U is —CH$_2$— or —N(R$_2$)— wherein R$_2$ is hydrogen or loweralkyl, with the proviso that W is —C(O)— when U is —N(R$_2$)—;

R$_3$ is
  (1) loweralkyl,
  (2) loweralkenyl,
  (3) alkynyl,
  (4) haloalkyl,
  (5) cycloalkylalkyl,
  (6) cycloalkenylalkyl,
  (7) alkoxyalkyl,
  (8) thioalkoxyalkyl,
  (9) ((alkoxy)alkoxy)alkyl,
  (10) hydroxyalkyl,
  (11) —(CH$_2$)$_d$NHR$_{18}$ wherein d is 1 to 3 and R$_{18}$ is hydrogen, loweralkyl or an N-protecting group,
  (12) arylalkyl or
  (13) (heterocyclic)alkyl;
R$_{3a}$ is hydrogen or fluoro;
R$_4$ is loweralkyl, cycloalkylalkyl or arylalkyl;
R$_5$ is hydrogen, loweralkyl, hydroxyalkyl, loweralkenyl or formyl;

$R_6$ is —OH or —NH$_2$; and
D is

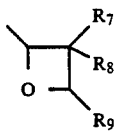

wherein $R_7$ is hydrogen or loweralkyl and $R_8$ is hydrogen, loweralkyl, hydroxyalkyl, alkoxyalkyl, thioalkoxyalkyl, haloalkyl, aminoalkyl, alkylaminoalkyl, dialkylaminoalkyl, cycloalkyl, cycloalkylalkyl, loweralkenyl, alkynyl, aryl, arylalkyl, heterocyclic or heterocyclicalkyl; or $R_7$ and $R_8$ together are —(CH$_2$)$_n$— wherein n is 3-6; and $R_9$ is hydrogen or loweralkyl;
or a pharmaceutically acceptable salt, ester or prodrug thereof.

2. A compound of the formula:

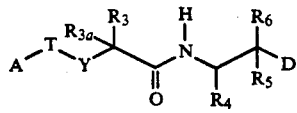

wherein A is
(1) hydrogen
(2) loweralkyl,
(3) aryl,
(4) arylalkyl,
(5) heterocyclic,
(6) (heterocyclic)alkyl,
(7) —OR$_{10}$ or —SR$_{10}$ wherein R$_{10}$ is hydrogen, loweralkyl or aminoalkyl,
(8) —NR$_{11}$R$_{12}$ wherein R$_{11}$ and R$_{12}$ are independently selected from hydrogen, loweralkyl aminoalkyl, cyanoalkyl, hydroxyalkyl, carboxyalkyl, alkoxycarbonylalkyl, (amino)carboxyalkyl, ((N-protected)amino)carboxyalkyl, (alkylamino)carboxyalkyl, ((N-protected)alkylamino)carboxyalkyl, (dialkylamino)carboxyalkyl, (amino)alkoxycarbonylalkyl, ((N-protected)amino)alkoxycarbonylalkyl, (alkylamino)alkoxycarbonylalkyl, ((N-protected)alkylamino)alkoxycarbonylalkyl and (dialkylamino)alkoxycarbonylalkyl,
(9) (alkoxy)(alkyl)aminoalkyl,
(10) (alkoxy)aminoalkyl,
(11) (alkoxyalkoxy)aminoalkyl,
(12) (alkoxyalkoxy)(alkyl)aminoalkyl or
(13) R$_{13}$—Q—B— wherein
B is
(i) —N(R$_{19}$)— wherein R$_{19}$ is hydrogen or loweralkyl,
(ii) —NHCH$_2$—
(iii) —S—,
(iv) —O—,
(v) —(CH$_2$)$_b$— wherein b is 0-4 or
(vi) —CH(OR$_{20}$)— wherein R$_{20}$ is hydrogen, loweralkyl or —C(O)R$_{21}$ wherein R$_{21}$ is loweralkyl or haloalkyl,
Q is
(i) —C(O)—,
(ii) —S(O)—,
(iii) —S(O)$_2$— or
(iv) —CH(OR$_{14}$)— wherein R$_{14}$ is hydrogen, loweralkyl or —C(O)R$_{15}$ wherein R$_{15}$ is loweralkyl or haloalkyl and
R$_{13}$ is
(i) loweralkyl,
(ii) cycloalkyl,
(iii) cycloalkylalkyl,
(iv) cycloalkenyl,
(v) cycloalkenylalkyl,
(vi) amino,
(vii) di-(alkoxyalkyl)amino,
(viii) di-(alkoxyalkoxyalkyl)amino,
(ix) di-(hydroxyalkyl)amino,
(x) aminoalkyl,
(xi) (N-protected)aminoalkyl,
(xii) (N-protected)(alkyl)aminoalkyl,
(xii) aryl,
(xiv) arylalkyl,
(xv) heterocyclic,
(xvi) (heterocyclic)alkyl,
(xvii) carboxyalkyl,
(xviii) (amino)carboxyalkyl,
(xix) ((N-protected)amino)carboxyalkyl,
(xx) (alkylamino)carboxyalkyl,
(xxi) ((N-protected)(alkyl)amino)carboxyalkyl,
(xxii) (dialkylamino)carboxyalkyl,
(xxiii) alkoxycarbonylalkyl,
(xxiv) (amino)alkoxycarbonylalkyl,
(xxv) ((N-protected)amino)alkoxycarbonylalkyl,
(xxvi) (alkylamino)alkoxycarbonylalkyl,
(xxvii) (((N-protected)(alkyl)amino)alkoxycarbonylalkyl,
(xxviii) (dialkylamino)alkoxycarbonylalkyl,
(xxix) —N=C(NR$_a$R$_b$)$_2$ wherein at each occurrence R$_a$ and Rb are independently selected from loweralkyl or
(xxx) R$_{16}$—G—R$_{17}$— wherein R$_{16}$ is
(a) loweralkyl,
(b) loweralkenyl,
(c) cycloalkyl,
(d) cycloalkenyl,
(e) cycloalkylalkyl,
(f) cycloalkenylalkyl,
(g) hydroxyalkyl,
(h) dihydroxyalkyl,
(i) alkoxyalkyl,
(j) alkoxyalkoxyalkyl,
(k) polyalkoxyalkyl,
(l) aryl,
(m) arylalkyl,
(n) heterocyclic,
(o) (heterocyclic)alkyl,
(p) carboxyalkyl,
(q) (amino)carboxyalkyl,
(r) ((N-protected)amino)carboxyalkyl,
(s) (alkylamino)carboxyalkyl,
(t) ((N-protected)alkylamino)carboxyalkyl,
(u) (dialkylamino)carboxyalkyl,
(v) alkoxycarbonylalkyl,
(w) (amino)alkoxycarbonylalkyl,
(x) ((N-protected)amino)alkoxycarbonylalkyl,
(y) (alkylamino)alkoxycarbonylalkyl,
(z) ((N-protected)alkylamino)alkoxycarbonylalkyl,
(aa) (dialkylamino)alkoxycarbonylalkyl,
(bb) alkylsulfonyl,
(cc) alkylsulfonylalkyl,
(dd) arylsulfonyl, (ee) arylsulfonylalkyl,
(ff) (heterocyclic)sulfonyl,
(gg) (heterocyclic)sulfonylalkyl,
(hh) aminoalkyl,
(ii) (N-protected)aminoalkyl,
(jj) alkylaminoalkyl,
(kk) (N-protected)(alkyl)aminoalkyl or
(ll) dialkylaminoalkyl, $R_{17}$ is absent or alkylene and
G is —S—, —S(O)—, —S(O)$_2$—, —O— or —N(R$_{22}$)— wherein
$R_{22}$ is hydrogen or loweralkyl;
T is —CH(R$_1$)— or —C(=CHR$_{1a}$)— wherein $R_1$ is
(1) loweralkyl,
(2) loweralkenyl,
(3) cycloalkylalkyl,
(4) cycloalkenylalkyl,
(5) alkoxyalkyl,
(6) thioalkoxyalkyl,
(7) arylalkyl,
(8) (heterocyclic)alkyl,
(9) aryloxyalkyl,
(10) thioaryloxyalkyl,
(11) arylaminoalkyl,
(12) aryloxy,
(13) thioaryloxy,
(14) arylalkoxyalkyl,
(15) arylthioalkoxyalkyl or
(16) arylamino; and
$R_{1a}$ is aryl or arylalkyl;
Y is
(1) —CH$_2$—,
(2) —CH(OH)—,
(3) —C(O)—,
(4) —NH—,
(5) —O—,
(6) —S—,
(7) —S(O)—,
(8) —S(O)$_2$—,
(9) —N(O)—,
(10) —P(O)O— or
(11) —W—U— wherein
W is —C(O)— or —CH(OH)— and
U is —CH$_2$— or —N(R$_2$)— wherein R$_2$ is hydrogen or loweralkyl, with the proviso that W is —C(O)— when U is —N(R$_2$)—;
$R_3$ is
(1) loweralkyl,
(2) loweralkenyl,
(3) alkynyl,
(4) haloalkyl,
(5) cycloalkylalkyl,
(6) cycloalkenylalkyl,
(7) alkoxyalkyl,
(8) thioalkoxyalkyl,
(9) ((alkoxy)alkoxy)alkyl,
(10) hydroxyalkyl,
(11) —CH$_2$)$_d$NHR$_{18}$ wherein d is 1 and R$_{18}$ is hydrogen, loweralkyl or an N-protecting group,
(12) arylalkyl or
(13) (heterocyclic)alkyl;
$R_{3a}$ is hydrogen of fluoro;
$R_4$ is loweralkyl, cycloalkylalkyl or arylalkyl;
$R_5$ hydrogen, loweralkyl, hydroxyalkyl, loweralkenyl or formyl;
$R_6$ is —OH or —NH$_2$; and
D is

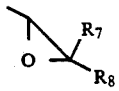

wherein R$_7$ is hydrogen or loweralkyl and R$_8$ is hydrogen, loweralkyl, hydroxyalkyl, alkoxyalkyl, thioalkoxyalkyl, haloalkyl, aminoalkyl, alkylaminoalkyl, dialkylaminoalkyl, cycloalkyl, cycloalkylalkyl, loweralkenyl, alkynyl, aryl, arylalkyl, heterocyclic or heterocyclicalkyl; or R$_7$ and R$_8$ taken together are —(CH$_2$)$_n$— wherein n is 3-6; with the proviso that when T is —CH(R$_1$)— wherein R$_1$ is loweralkyl and Y is —C(O)—NH— and R$_3$ is loweralkyl and R$_{3a}$ is hydrogen and R$_4$ is cycloalkylalkyl and R$_5$ is hydrogen and R$_6$ is OH and R$_7$ and R$_8$ are hydrogen, then A is other than R$_{13}$—Q—B— wherein B is —NH— and Q is —C(O)— and R$_{13}$ is loweralkyl—O—;

or a pharmaceutically acceptable salt, ester or prodrug thereof.

3. The compound of claim 1 wherein
A is (heterocyclic)alkyl or R$_{13}$—Q—CH$_2$— wherein Q is —C(O)— or —S(O)$_2$— and R$_{13}$ is heterocyclic or R$_{16}$—G— wherein G is —N(R$_{22}$) — wherein R$_{22}$ is hydrogen or loweralkyl and R$_{16}$ is (heterocyclic)alkyl;
T is —CH(R$_1$)— wherein R$_1$ is arylalkyl;
Y is —W—U— wherein W is —C(O)— and U is —NH—;
$R_{3a}$ is hydrogen;
$R_3$ is (heterocyclic)alkyl;
$R_4$ is cycloalkylalkyl;
$R_5$ is hydrogen;
$R_6$ is —OH—; and D is

wherein R$_8$ is loweralkyl.

4. A compound selected from the group consisting of
(2S) 2-Benzyl-3-(1-methyl-piperazin-4-ylsulfonyl)-propionyl-(4-thiazolyl)alanine Amide of (1R,2S,2'S,3'S)-2-Amino-3-cyclohexyl-1-(3'-(ethyl)oxetan-2'-yl)-1-(hydroxy)propane;

(2R)-2-Benzyl-3-((4-methylpiperazin-1-yl)carbonyl-propionyl-(4-thiazolyl)alanine Amide of (1R,2S,2'S,3'S)-2-Amino-3-cyclohexyl-1-(3'-(ethyl)oxetan-2'-yl)-1-(hydroxy)propane;

(2R)-2-Benzyl-3-((2-pyridin-2-ylethyl)methylaminocarbonyl)propionyl-(4-thiazolyl)alanine Amide of (1R,2S,2'S,3'S)-2-Amino-3-cyclohexyl-1-(3'-(ethyl)oxetan-2'-yl)-1-(hydroxy)propane;

(2R)-2-Benzyl-3-(imidazol-1-yl)propionyl-(4-thiazolyl)alanine Amide of (1R,2S,2'S,3'S)-2-Amino-3-cyclohexyl-1-(3'-(ethyl)oxetan-2'-yl)-1-(hydroxy)propane;

(2S)-2-Benzyl-3-(1-methylazetidin-3-ylsulfonyl)propionyl-(4-thiazolyl)alanine Amide of (1R,2S,2'S,3'S)-2-Amino-3-cyclohexyl-1-(3'-(ethyl)oxetan-2'-yl)-1-(hydroxy)propane;

(2R)-2-Benzyl-3-(4-methylpiperazin-1-ylcarbonyl)-propionyl-(1-imidazolyl)alanine Amide of (1R,2S,2'S,3'S)-2-Amino-3-cyclohexyl-1-(3'-(ethyl)oxetan-2'-yl)-1-(hydroxy)propane;

(2R)-2-Benzyl-3-(4-methylpiperazin-1-ylcarbonyl)-propionyl-leucine Amide of (1R,2S,2'S,3'S)-2-Amino-3-cyclohexyl-1-(3'-(ethyl)oxetan-2'-yl)-1-(hydroxy)propane;

(2R)-2-Benzyl-3-(imidazol-1-yl)propionyl-Leucine Amide of (1R,2S,2'S,3'S))-2-Amino-3-cyclohexyl-1-(3'-(ethyl)oxetan-2'-yl)-1-(hydroxy)propane; and (2R)-2-Benzyl-3-(imidazol-1-yl)propionyl-(nor)Leucine Amide of (1R,2S,2'S,3'S)-2-Amino-3-cyclohexyl-1-(3'-(ethyl)oxetan-2'-yl)-1-(hydroxy)propane; or a pharmaceutically acceptable salt, ester or prodrug thereof.

5. A compound of the formula

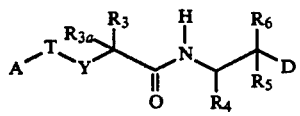

wherein

A is (heterocyclic)alkyl or $R_{13}Q$—$CH_2$— wherein —C(O)— or —S(O)$_2$— and $R_{13}$ is heterocyclic or $R_{16}$—G— wherein G is —N($R_{22}$)— wherein $R_{22}$ is hydrogen or loweralkyl and $R_{16}$ is (heterocyclic)alkyl;

T is —CH($R_1$)— wherein $R_1$ is arylalkyl;

Y is —W—U— wherein W is —C(O)— and U is —NH;

$R_{3a}$ is hydrogen;

$R_3$ is (heterocyclic)alkyl or loweralkyl;

$R_4$ is cycloalkylalkyl;

$R_5$ is hydrogen;

$R_6$ is —OH—; and D is

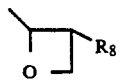

wherein $R_8$ is loweralkyl:
or a pharmaceutically acceptable salt, ester or prodrug thereof.

6. A compound of the formula;

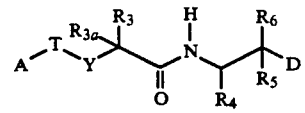

wherein

A is (heterocyclic)alkyl or $R_{13}$—Q—$CH_2$— wherein Q is —C(O)— or —S(O)$_2$— and $R_{13}$ is heterocyclic or $R_{16}$—G— wherein G is —N($R_{22}$)— wherein $R_{22}$ is hydrogen or loweralkyl and $R_{16}$ is (heterocyclic)alkyl;

T is —CH($R_1$)— wherein $R_1$ is arylalkyl;

Y is —W—U— wherein W is —C(O)— and U is —NH—;

$R_{3a}$ is hydrogen;

$R_3$ is (heterocyclic)alkyl or loweralkyl;

$R_4$ is cycloalkylalkyl;

$R_5$ is hydrogen;

$R_6$ is —OH—; and D is

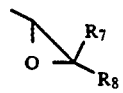

wherein $R^7$ is hydrogen and $R_8$ is loweralkyl:
or a pharmaceutically acceptable salt, ester or prodrug thereof.

7. A method for inhibiting renin comprising administering to a mammal in need of such treatment a therapeutically effective amount of a compound of claim 1.

8. A pharmaceutical composition for inhibiting renin comprising a pharmaceutical carrier and a therapeutically effective amount of a compound of claim 1.

9. A method for treating hypertension or congestive heart failure comprising administering to a mammal in need a therapeutically effective amount of a compound of claim 1.

10. A method for treating hypertension or congestive heart failure comprising administering to a mammal in need a therapeutically effective amount of a compound of claim 1 in combination with another cardiovascular agent.

11. A method for inhibiting renin comprising administering to a mammal in need a therapeutically effective amount of a compound of claim 4.

12. A pharmaceutical composition for inhibiting renin comprising a pharmaceutical carrier and a therapeutically effective amount of a compound of claim 4.

13. A method for treating hypertension or congestive heart failure comprising administering to a mammal in need a therapeutically effective amount of a compound of claim 4.

14. A Method for treating hypertension or congestive heart failure comprising administering to a mammal in need a therapeutically effective amount of a compound of claim 4 in combination with another cardiovascular agent.

15. A method for inhibiting renin comprising administering to a mammal in need a therapeutically effective amount of a compound of claim 2.

16. A pharmaceutical composition for inhibiting renin comprising a pharmaceutical carrier and a therapeutically effective amount of a compound of claim 2.

17. A method for treating hypertension or congestive heart failure comprising administering to a mammal in need a therapeutically effective amount of a compound of claim 2.

18. A method for treating hypertension or congestive heart failure comprising administering to a mammal in need a therapeutically effective amount of a compound of claim 2 in combination with another cardiovascular agent.

19. A method for inhibiting renin comprising administering to a mammal in need a therapeutically effective amount of a compound of claim 5.

20. A pharmaceutical composition for inhibiting renin comprising a pharmaceutical carrier and a therapeutically effective amount of a compound of claim 5.

21. A method for treating hypertension or congestive heart failure comprising administering to a mammal in need a therapeutically effective amount of a compound of claim 5.

22. A method for treating hypertension or congestive heart failure comprising administering to a mammal in need a therapeutically effective amount of a compound of claim 5 in combination with another cardiovascular agent.

23. A method for inhibiting renin comprising administering to a mammal in need a therapeutically effective amount of a compound of claim 6.

24. A method for inhibiting renin comprising a pharmaceutical carrier and a therapeutically effective amount of a compound of claim 6.

25. A method for treating hypertension or congestive heart failure comprising administering to a mammal in need a therapeutically effective amount of claim 6.

26. A method for treating hypertension or congestive heart failure comprising administering to a mammal in need a therapeutically effective amount of a compound of claim 6 in combination with another cardiovascular agent.

* * * * *

UNITED STATES PATENT AND TRADEMARK OFFICE
CERTIFICATE OF CORRECTION

PATENT NO.: 5,258,362
DATED: November 2, 1993
INVENTOR(S): Saul H. Rosenberg

It is certified that error appears in the above-indentified patent and that said Letters Patent is hereby corrected as shown below:

COLUMN 81, LINE 59: Delete "--$CH_2)_dNHR_{18}$ wherein d is 1" and Insert -- --$CH_2)_dNHR_{18}$ wherein d is 1 to 3-- , COLUMN 81, LINE 63: Delete "of" and Insert --or--

COLUMN 81, LINE 65: Delete "$R_5$ hydrogen" and Insert --$R_5$ is hydrogen--

COLUMN 82, LINE 49: Delete "carbonyl-" and Insert --carbonyl)- --

COLUMN 83, LINE 23: After "wherein" Insert --Q is --

Signed and Sealed this

Fourteenth Day of June, 1994

BRUCE LEHMAN

Attest:

Attesting Officer    Commissioner of Patents and Trademarks